United States Patent
Venturelli et al.

(10) Patent No.: US 11,608,524 B1
(45) Date of Patent: Mar. 21, 2023

(54) METHODS OF ANALYZING CELLS

(71) Applicant: WISCONSIN ALUMNI RESEARCH FOUNDATION, Madison, WI (US)

(72) Inventors: Ophelia S. Venturelli, Madison, WI (US); Philip A. Romero, Madison, WI (US); Ryan Hon Hean Hsu, Madison, WI (US); Jin Wen Tan, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 117 days.

(21) Appl. No.: 16/664,489

(22) Filed: Oct. 25, 2019

Related U.S. Application Data

(60) Provisional application No. 62/750,496, filed on Oct. 25, 2018.

(51) Int. Cl.
| | |
|---|---|
| *C12Q 1/686* | (2018.01) |
| *C12Q 1/6869* | (2018.01) |
| *C12Q 1/6809* | (2018.01) |
| *C12Q 1/6806* | (2018.01) |
| *G16B 40/10* | (2019.01) |
| *G16B 30/00* | (2019.01) |
| *C40B 70/00* | (2006.01) |
| *C40B 40/06* | (2006.01) |

(52) U.S. Cl.
CPC ......... *C12Q 1/6869* (2013.01); *C12Q 1/6806* (2013.01); *C12Q 1/6809* (2013.01); *G16B 30/00* (2019.02); *G16B 40/10* (2019.02); *C12Q 2535/122* (2013.01); *C12Q 2539/00* (2013.01); *C40B 40/06* (2013.01); *C40B 70/00* (2013.01)

(58) Field of Classification Search
CPC ................ C12Q 1/6869; C12Q 1/6806; C12Q 2539/00; C12Q 2535/122; C40B 70/00; C40B 40/06
See application file for complete search history.

(56) References Cited

U.S. PATENT DOCUMENTS

| | | | |
|---|---|---|---|
| 2015/0056620 A1* | 2/2015 | Ecker | G01N 21/64 506/8 |
| 2015/0376609 A1* | 12/2015 | Hindson | C40B 20/04 506/4 |
| 2016/0180018 A1* | 6/2016 | Millar | G16B 30/00 702/20 |
| 2016/0253584 A1* | 9/2016 | Fodor | C12Q 1/6813 235/494 |
| 2017/0307606 A1* | 10/2017 | Hallock | C12Q 1/6816 |

FOREIGN PATENT DOCUMENTS

| | | | | |
|---|---|---|---|---|
| WO | WO-2015100427 A1 * | 7/2015 | ........... | C12Q 1/6886 |
| WO | WO-2016040476 A1 * | 3/2016 | ............ | G06K 19/06 |
| WO | WO-2016126871 A2 * | 8/2016 | ......... | C12N 15/1096 |

OTHER PUBLICATIONS

Sun et al.("Rapid, species-specific detection of uropathogen 16S rDNA and rRNA at ambient temperature by dot-blot hybridization and an electrochemical sensor array." Molecular genetics and metabolism 84.1 (2005): 90-99.) (Year: 2005).*

Maughan et al. ("Analysis of the cystic fibrosis lung microbiota via serial Illumina sequencing of bacterial 16S rRNA hypervariable regions." (2012): e45791; 15 pages). (Year: 2012).*

Alain K, Querellou J (2009) Cultivating the uncultured: limits, advances and future challenges. Extremophiles 13: 583-594.

Bairey, E., Kelsic, E. D., and Kishony, R. "High-Order Species Interactions Shape Ecosystem Diversity" Nature Publishing Group 7, (2016): 1-7. doi:10.1038/ncomms12285.

Baret JC, Miller OJ, Taly V, Ryckelynck M, El-Harrak A, et al. (2009) Fluorescence-activated droplet sorting (FADS): efficient microfluidic cell sorting based on enzymatic activity. Lab on a Chip 9: 1850-1858.

Bartram AK, Lynch MD, Stearns JC, Moreno-Hagelsieb G, Neufeld JD (Jun. 2011). "Generation of multimillion-sequence 16S rRNA gene libraries from complex microbial communities by assembling paired-end illumina reads". Applied and Environmental Microbiology. 77 (11): 3846-52.

Boedicker JQ, Vincent ME, Ismagilov RF (2009) Microfluidic Confinement of Single Cells of Bacteria in Small Volumes Initiates High-Density Behavior of Quorum Sensing and Growth and Reveals Its Variability.

Burke CM, Darling AE (Sep. 20, 2016). "A method for high precision sequencing of near full-length 16S rRNA genes on an Illumina MiSeq". PeerJ. 4: e2492.

Chakravorty S, Helb D, Burday M, Connell N, Alland D (May 2007). "A detailed analysis of 16S ribosomal RNA gene segments for the diagnosis of pathogenic bacteria". Journal of Microbiological Methods. 69 (2): 330-9.

Clausell-Tormos J, Lieber D, Baret JC, El-Harrak A, Miller OJ, et al. (2008) Droplet-based microfluidic platforms for the encapsulation and screening of mammalian cells and multicellular organisms. Chemistry & Biology 15:427-437.

(Continued)

*Primary Examiner* — Sahana S Kaup

(74) *Attorney, Agent, or Firm* — Daniel A. Blasiole; DeWitt LLP

(57) ABSTRACT

Methods of analyzing cells, including interactions among different populations of cells. Methods include cell-containing liquid droplets with oligonucleotide-containing liquid droplets, hybridizing oligonucleotides to target nucleic acids from cells, extending the hybridized oligonucleotides on the target nucleic acids into cell identifier sequences on the target nucleic acids, and thereby identifying the type of cells initially present. The methods can be implemented in a high-throughput manner in a microfluidic system.

17 Claims, 32 Drawing Sheets
(29 of 32 Drawing Sheet(s) Filed in Color)
Specification includes a Sequence Listing.

(56) References Cited

OTHER PUBLICATIONS

Clauset, A., Newman, M. E. J., and Moore, C. "Finding Community Structure in Very Large Networks" Physical Review 70, No. 6 (2004): 66111.

Coenye T, Vandamme P (Nov. 2003). "Intragenomic heterogeneity between multiple 16S ribosomal RNA operons in sequenced bacterial genomes". FEMS Microbiology Letters. 228 (1): 45-9.

Coyte, K. Z., Schluter, J., and Foster, K. R. "The Ecology of the Microbiome: Networks, Competition, and Stability" Science 350, No. 6261 (2015): 663-666.

Faith, J. J., Ahern, P. P., Ridaura, V. K., Cheng, J., and Gordon, J. I. "Identifying Gut Microbe-Host Phenotype Relationships Using Combinatorial Communities in Gnotobiotic Mice." Science translational medicine 6, No. 220 (2014): 220ra11. doi:10.1126/scitranslmed.3008051.

Faith, J. J., McNulty, N. P., Rey, F. E., and Gordon, J. I. "Predicting a Human Gut Microbiota's Response to Diet in Gnotobiotic Mice." Science 333, No. 6038 (2011): 101-4. doi:10.1126/science.1206025.

Faust, K. and Raes, J. "Microbial Interactions: From Networks to Models." Nature reviews. Microbiology 10, No. 8 (2012): 538-50. doi:10.1038/nrmicro2832.

Ferrari BC, Binnerup SJ, Gillings M (2005) Microcolony cultivation on a soil substrate membrane system selects for previously uncultured soil bacteria. Applied and Environmental Microbiology 71: 8714-8720.

Ferrari BC, Winsley T, Gillings M, Binnerup S (2008) Cultivating previously uncultured soil bacteria using a soil substrate membrane system. Nature Protocols 3: 1261-1269.

Foster, K.R., Bell, T., 2012. Competition, not cooperation, dominates interactions among culturable microbial species. Curr. Biol. 22, 1845-1850. https://doi.org/10.1016/j.cub.2012.08.005.

Friedman, J. and Alm, E. J. "Inferring Correlation Networks from Genomic Survey Data." PLoS computational biology 8, No. 9 (2012): e1002687. doi:10.1371/journal.pcbi.1002687.

Fuchs, M., Wallner, G., Beisker, W., Schwippl, I., Ludwig, W., and Amann, R. (1998). Flow Cytometric Analysis of the in Situ Accessibility of Escherichia coli 16S rRNA for Fluorescently Labeled Oligonucleotide Probes. Appl. Environ. Microbiol. 64 (12), 4973-4982.

Fujimoto, T., Imaeda, H., Takahashi, K., Kasumi, E., Bamba, S., Fujiyama, Y., and Andoh, A. "Decreased Abundance of Faecalibacterium Prausnitzii in the Gut Microbiota of Crohn's Disease." Journal of gastroenterology and hepatology 28, No. 4 (2013): 613-9. doi:10.1111/jgh.12073.

Geris, L. and Gomez-Cabrero, D. "Uncertainty in Biology: A Computational Modeling Approach" 17, (2016): doi: 10.1007/978-3-319-21296-8.

Gray MW, Sankoff D, Cedergren RJ (1984). "On the evolutionary descent of organisms and organelles: a global phylogeny based on a highly conserved structural core in small subunit ribosomal RNA". Nucleic Acids. Research. 12 (14): 5837-52.

Guo, M. T., Rotem, A., Heyman, J. A., and D. A. Weitz. "Droplet Microfluidics for High-Throughput Biological Assays." Lab on a Chip 12, No. 12 (2012): 2146-55. doi:10.1039/c21c21147e.

Grodrian A, Metze J, Henkel T, Martin K, Roth M, et al. (2004) Segmented flow generation by chip reactors for highly parallelized cell cultivation. Biosensors & Bioelectronics 19: 1421-1428.

Hammarlund, S.P., Chacón, J.M., Harcombe, W.R., 2018. A shared limiting resource leads to competitive exclusion in a cross-feeding system 1-20.

Hatori MN, Kim SC, Abate AR. Particle-Templated Emulsification for Microfluidics-Free Digital Biology. Anal Chem. Aug. 21, 2018;90(16):9813-9820.

Holtze, C., Rowat, A.C., Agresti, J.J., Hutchison, J.B., Angilè, F.E., Schmitz, C.H.J., Köster, S., Duan, H., Humphry, K.J., Scanga, R.A., Johnson, J.S., Pisignano, D., Weitz, D.A., 2008. Biocompatible surfactants for water-in-fluorocarbon emulsions. Lab Chip 8, 1632. https://doi.org/10.1039/b806706f.

Ingham CJ, Sprenkels A, Bomer J, Molenaar D, Van Den Berg A, et al. (2007) The micro-Petri dish, a million-well growth chip for the culture and highthroughput screening of microorganisms. Proceedings of the National Academy of Sciences of the United States of America 104: 18217-18222.

Inoue I, Wakamoto Y, Moriguchi H, Okano K, Yasuda K (2001) On-chip culture system for observation of isolated individual cells. Lab on a Chip 1: 50-55.

Jia, G., Stephanopoulos, G., and Gunawan, R. "Ensemble Kinetic Modeling of Metabolic Networks from Dynamic Metabolic Profiles" Metabolites 2, (2012): 891-912. doi:10.3390/metabo2040891.

Jovel J, Patterson J, Wang W, Hotte N, O'Keefe S, Mitchel T, Perry T, Kao D, Mason AL, Madsen KL, Wong GK (Jan. 1, 2016). "Characterization of the Gut Microbiome Using 16S or Shotgun Metagenomics". Frontiers in Microbiology. 7: 459.

Kaeberlein T, Lewis K, Epstein SS (2002) Isolating "uncultivable" microorganisms in pure culture in a simulated natural environment. Science 296:1127-1129.

Karbaschi, M., Shahi, P., Abate, A.R., 2017. Rapid, chemical-free breaking of microfluidic emulsions with a hand-held antistatic gun. Biomicrofluidics. https://doi.org/10.1063/1.4995479.

Klein, A. M., Mazutis, L., Akartuna, I., Tallapragada, N., Veres, A., Li, V., Peshkin, L., Weitz, D. A., and Kirschner, M. W. "Droplet Barcoding for Single-Cell Transcriptomics Applied to Embryonic Stem Cells" Cell 161, No. 5 (2015): 1187-1201. doi:10.1016/j.cell.2015.04.044.

Koster S, Angile FE, Duan H, Agresti JJ, Wintner A, et al. (2008) Drop-based microfluidic devices for encapsulation of single cells. Lab on a Chip 8:1110-1115.

Krautkramer KA, Kreznar JH, Romano KA, Vivas EI, Barrett-Wilt GA, Rabaglia ME, Keller MP, Attie AD, Rey FE, Denu JM. Diet-Microbiota Interactions Mediate Global Epigenetic Programming in Multiple Host Tissues. Mol Cell. Dec. 1, 2016;64(5):982-992. doi: 10.1016/j.molcel.2016.10.025.

Kuepfer, L., Peter, M., Sauer, U., and Stelling, J. "Ensemble Modeling for Analysis of Cell Signaling Dynamics" Nature biotechnology 25, No. 9 (2007): 1001-1006. doi:10.1038/nbt1330.

Liu WS, Kim HJ, Lucchetta EM, Du WB, Ismagilov RF (2009) Isolation, incubation, and parallel functional testing and identification by FISH of rare microbial single-copy cells from multi-species mixtures using the combination of chemistrode and stochastic confinement. Lab on a Chip 9: 2153-2162.

Lovell, D., Pawlowsky-Glahn, V., Egozcue, J. J., and Marguerat, S. "Proportionality : a Valid Alternative to Correlation for Relative Data" PLOS Computational biology 11, No. 3 (2015): 1-12. doi:10.1371/journal.pcbi.1004075.

Macosko, E.Z., Basu, A., Satija, R., Nemesh, J., Shekhar, K., Goldman, M., Tirosh, I., Bialas, A.R., Kamitaki, N., Martersteck, E.M., Trombetta, J.J., Weitz, D.A., Sanes, J.R., Shalek, A.K., Regev, A., McCarroll, S.A., 2015. Highly parallel genome-wide expression profiling of individual cells using nanoliter droplets. Cell 161, 1202-1214. haps://doi.org/10.1016/j.cell.2015.05.002.

Martin K, Henkel T, Baier V, Grodrian A, Schon T, et al. (2003) Generation of larger numbers of separated microbial populations by cultivation in segmented-flow microdevices. Lab on a Chip 3: 202-207.

Maurice, C. F. and Turnbaugh, P. J. "Quantifying the Metabolic Activities of Human-Associated Microbial Communities across Multiple Ecological Scales" FEMS Microbiology Reviews 37, (2013): 830-848. doi:10.1111/1574-6976.12022.

Mounier, J., Monnet, C., Vallaeys, T., Arditi, R., Sarthou, A.-S., Hélias, A., and Irlinger, F. "Microbial Interactions within a Cheese Microbial Community." Applied and environmental microbiology 74, No. 1 (2008): 172-81. doi:10.1128/AEM.01338-07.

Park, J., Kerner, A., Burns, M. A., and Lin, X. N. "Microdroplet-Enabled Highly Parallel Co-Cultivation of Microbial Communities" PLoS One 6, No. 2 (2011): doi:10.1371/journal.pone.0017019.

Qin, J., Li, Y., Cai, Z., Li, S., Zhu, J., Zhang, F., Liang, S., Zhang, W., Hansen, T., Sanchez, G., Raes, J., Falony, G., Okuda, S., and Almeida, M. "A Metagenome-Wide Association Study of Gut Microbiota in Type 2 Diabetes" Nature 490, No. 7418 (2012): 55-60. doi:10.1038/nature11450.

(56) References Cited

OTHER PUBLICATIONS

Qin, J., Li, R., Raes, J., Arumugam, M., Burgdorf, K. S., Manichanh, C., Nielsen, T., Pons, N., Levenez, F., Yamada, T., Mende, D. R., Li, J., Xu, J., Li, S., Li, D., Cao, J., Wang, B., Liang, H., Zheng, H., Xie, Y., Tap, J., Lepage, P., Bertalan, M., Batto, J.-M., Hansen, T., Paslier, D. Le, Linneberg, A., Nielsen, H. B., Pelletier, E., Renault, P., Sicheritz-Ponten, T., Turner, K., Zhu, H., Yu, C., Li, S., Jian, M., Zhou, Y., Li, Y., Zhang, X., Li, S., Qin, N., Yang, H., Wang, J., Brunak, S., Doré, J., Guarner, F., Kristiansen, K., Pedersen, O., Parkhill, J., Weissenbach, J., Bork, P., Ehrlich, S. D., and Wang, J. "A Human Gut Microbial Gene Catalogue Established by Metagenomic Sequencing." Nature 464, No. 7285 (2010): 59-65. doi:10.1038/nature08821.
Romero, P. A. and Abate, A. R. "Flow Focusing Geometry Generates Droplets through a Plug and Squeeze Mechanism" Lab on a Chip 12, No. 24 (2012): 5130-5132. doi:10.1039/c2lc40938k.
Romero, P. A., Tran, T. M., and Abate, A. R. "Dissecting Enzyme Function with Microfluidic-Based Deep Mutational Scanning" Proceedings of the National Academy of Sciences 112, No. 23 (2015): 7159-7164. doi:10.1073/pnas.1422285112.
Rotem, A., Ram, O., Shoresh, N., Sperling, R. A., Schnall-Levin, M., Zhang, H., Basu, A., Bernstein, B. E., and Weitz, D. A. "High-Throughput Single-Cell Labeling (Hi-SCL) for RNA-Seq Using Drop-Based Microfluidics" PLoS One 10, No. 5 (2015): 1-14. doi:10.1371/journal.pone.0116328.
Scher, J. U., Sczesnak, A., Longman, R. S., Segata, N., Ubeda, C., Bielski, C., Rostron, T., Cerundolo, V., Pamer, E. G., Abramson, S. B., Huttenhower, C., and Littman, D. R. "Expansion of Intestinal Prevotella Copri Correlates with Enhanced Susceptibility to Arthritis." eLife 2, (2013): e01202. doi:10.7554/eLife.01202.
Smith, T., Heger, A., Sudbery, I., 2017. UMI-tools: modeling sequencing errors in Unique Molecular Identifiers to improve quantification accuracy. Genome Res. 27, 491-499. https://doi.org/10.1101/gr.209601.116.
Spencer, S. J., Tamminen, M. V, Preheim, S. P., Guo, M. T., Briggs, A. W., Brito, I. L., Weitz, D. A., Pitkänen, L. K., Vigneault, F., Virta, M. P. J., and Alm, E. J. "Massively Parallel Sequencing of Single Cells by epicPCR Links Functional Genes with Phylogenetic Markers" ISME 10, (2016): 427-436. doi:10.1038/ismej.2015.124.
Stein, R. R., Bucci, V., Toussaint, N. C., Buffie, C. G., Rätsch, G., Pamer, E. G., Sander, C., and Xavier, J. B. "Ecological Modeling from Time-Series Inference: Insight into Dynamics and Stability of Intestinal Microbiota." PLoS computational biology 9, No. 12 (2013): e1003388. doi:10.1371/journal.pcbi.1003388.
Thota, V. R., Dacha, S., and Natarajan, A. "Eggerthella Lenta Bacteremia in a Crohn's Disease Patient after Ileocecal Resection" Future Microbiology 6, (2011): 595-597.
Tsukuda, Miyuki; Kitahara, Kei; Miyazaki, Kentaro (Aug. 30, 2017). "Comparative RNA function analysis reveals high functional similarity between distantly related bacterial 16 S rRNAs". Scientific Reports. 7 (1).
Van De Peer Y, Chapelle S, De Wachter R (1996). "A quantitative map of nucleotide substitution rates in bacterial rRNA". Nucleic Acids Research. 24 (17): 3381-91.
Venturelli, O. S., El-Samad, H., and Murray, R. M. "Synergistic Dual Positive FeedbackLoops Established by Molecular Sequestration Generate Robust Bimodal Response" Proceedings of the National Academy of Sciences 109, No. 48 (2012): doi:10.1073/pnas.1211902109.
Venturelli OS, Carr AC, Fisher G, Hsu RH, Lau R, Bowen BP, Hromada S, Northen T, Arkin AP. Deciphering microbial interactions in synthetic human gut microbiome communities. Mol Syst Biol. Jun. 21, 2018;14(6):e8157.
Venturelli, O.S., Tei, M., Bauer, S., Chan, L.J.G., Petzold, C.J., Arkin, A.P., 2017. Programming mRNA decay to modulate synthetic circuit resource allocation. Nat. Commun. 8, 15128. https://doi.org/10.1038/ncomms15128.
Venturelli, O. S., Zuleta, I., Murray, R. M., and El-Samad, H. "Population Diversification in a Yeast Metabolic Program Promotes Anticipation of Environmental Shifts" PLoS Biology 109, No. 48 (2015): E3324-E3333. doi:10.1371/journal.pbio.1002042.
Větrovský T, Baldrian P (Feb. 27, 2013). "The variability of the 16S rRNA gene in bacterial genomes and its consequences for bacterial community analyses". PloS One. 8 (2): e57923.
Weisburg WG, Barns SM, Pelletier DA, Lane DJ (Jan. 1991). "16S ribosomal DNA amplification for phylogenetic study". Journal of Bacteriology. 173 (2): 697-703.
Woese CR, Fox GE (Nov. 1977). "Phylogenetic structure of the prokaryotic domain: the primary kingdoms". Proceedings of the National Academy of Sciences of the United States of America. 74 (11): 5088-90.
Yang B, Wang Y, Qian PY (Mar. 2016). "Sensitivity and correlation of hypervariable regions in 16S rRNA genes in phylogenetic analysis". BMC Bioinformatics. 17 (1): 135.
Zeitoun, R. I., Garst, A. D., Degen, G. D., Pines, G., Mansell, T. J., Glebes, T. Y., Boyle, N. R., and Gill, R. T. "Multiplexed Tracking of Combinatorial Genomic Mutations in Engineered Cell Populations." Nature Biotechnology 33, No. 6 (2015): 631-637.
Zengler K, Toledo G, Rappe M, Elkins J, Mathur EJ, et al. (2002) Cultivating the uncultured. Proceedings of the National Academy of Sciences of the United States of America 99: 15681-15686.

\* cited by examiner

A

B

METHODS OF ANALYZING CELLS

STATEMENT REGARDING FEDERALLY SPONSORED RESEARCH

This invention was made with government support under W911NF-17-1-0296 awarded by the ARMY/ARO. The government has certain rights in the invention.

BACKGROUND

In nature, most microbes live in synergistic communities as a way to adapt to and thrive in various environments, such as the ocean, soil, and higher organisms as hosts. These microbial communities play important roles in a wide spectrum of ecosystems and form diverse interactions among community members and with their surroundings. For example, the human body is a representative host for natural microbial communities: over 100 trillion bacteria are estimated to be present in the human gut, more than 600 microbial species are known to inhabit the human oral cavity, and over 100 different bacterial 16S rRNA are present on human skin. These microbes are believed to be closely related to human health. For instance, the gut microbiota is known to contribute to digestion of nutrients, stimulation of immunity and protection of the host from inflammatory diseases. Despite their ubiquitousness and apparent significance, our understanding of these microbial communities remains very limited, largely owing to their inherent complexity and the difficulty in laboratory cultivation of most of the microbes.

The majority of existing microbial species, estimated to be in the millions, have not been cultured in the laboratory, which severely limits the extent to which they can be characterized and further studied. One important reason behind this "unculturability" is that conventional laboratory cultivation is aimed at pure cultures of individual species, while in nature, the survival and growth of microorganisms are largely associated with their interactions with other members of the community in which they live. These interactions are mediated by various molecules such as secondary metabolites, quorum sensing molecules, and peptides. Accordingly, researchers have attempted to develop alternative cultivation techniques that allow interactions among microbes (Kaeberlein et al, 2001; Ferrari et al., 2005; Zengler et al., 2002; Ferrari et al., 2008; Alain et al., 2009). For example, Kaeberlein et al. successfully isolated and cultured previously uncultivated marine microorganisms by using a multi-chamber set-up which allowed the diffusion of small molecules through membranes (Kaeberlein et al, 2001).

Recent years have seen the increasing application of microfluidics, a powerful technological platform featuring small-scale and rapid operations, to cell cultivation and subsequent analysis. In particular, microfluidic compartmentalization has been widely utilized. For example, microwells have been used to confine and culture various microorganisms (Inoue et al., 2001; Ingham et al., 2007), including bacteria of which the growth was quorum-sensing dependent (Boedicker et al., 2009). Microfluidics-generated droplets represent another strategy for creating localized environments for diverse applications such as cell cultivation (Grodrian et al., 2004; Liu et al., 2009; Martin et al., 2003; Koster et al., 2008), screening (Clausell-Tormos et al., 2008) and sorting (Baret et al., 2009). It should be noted that microbial communities have started being examined using microfluidic approaches (Liu et al., 2009). Nevertheless, previous studies have focused exclusively on obtaining and analyzing pure cultures, which did not address the key question of how microbial interactions influence microbial community behaviors.

Strategies of investigating interactions among members of microbial communities and interactions among other types of cells are needed.

SUMMARY OF THE INVENTION

One aspect of the invention is directed to a method of using microfluidics and gene sequencing in a microfluidic system to study cellular interactions.

In the exemplary version shown in FIG. 1A, cells from a diverse cellular community (such as a microbial community) are encapsulated into millions of picoliter droplets that are dispersed in an oil phase. Each cell droplet can contain a random set of cells (e.g., 1-3 cells). The cell droplets are incubated to allow the microbes to interact, assemble into a community, and perform functional activities.

After the cell droplets are incubated to promote interactions, the cell droplets are individually merged with single droplets containing lysis buffer and a bead (preferably a single bead) comprising immobilized oligonucleotides linked thereto. Each oligonucleotide contains a barcode that uniquely identifies the oligonucleotide (unique molecule identifier, UMI), a barcode that uniquely identifies the bead (unique bead identifier (UBI)) (or if more than one bead, all the beads contained in the merged droplet), and a capture sequence for hybridizing to a target sequence of a nucleic acid in each of the cells. In some versions, the capture sequence is configured to hybridize to a conserved portion of 16S rRNA.

Upon the droplets merging, the cells lyse, and the target sequences bind to the capture sequences, and the target sequences, acting as primers, are extended along the nucleic acid to which each is hybridized into a cell identifier sequence identifying the type of cell harboring the nucleic acid. In some versions, the cell identifier sequence comprises a variable region of 16S rRNA.

After extending the oligonucleotides, the beads are collected and combined, and the extended oligonucleotides are amplified and then sequenced. Each cell identifier sequence represented in the extended oligonucleotide sequences can be associated with a particular UMI and UBI. These associations can be used to identify the type and quantity of each type of cell in each cell droplet, and thereby indicate how the types of cells in the cell droplets interact with each other. The presence or absence of specific cells in a droplet can be indicative of different types of cells preferentially interacting with other types of cells in the bulk culture or in the droplet and can be used to reconstruct the cells' ecological network or spatial distribution due to cell adherence.

Other aspects of the invention are described elsewhere herein.

The objects and advantages of the invention will appear more fully from the following detailed description of the preferred embodiment of the invention made in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 1A) Schematic of droplet-microfluidic workflow for large-scale mapping of microbial interactions in microbiomes. Droplet-microfluidics is used to encapsulate microbes into monodispersed water-in-oil emulsions. Microbial assemblages are incubated for a period of time and then reinjected. Each droplet containing a sub-community is merged with a droplet containing a uniquely barcoded bead resuspended in lysis buffer. cDNA synthesis, library preparation, and multiplexed next-generation sequencing is then performed. Network inference methods are used to infer microbial interactions based on species covariation. (FIG. 1B) Model-guided design of microbial community behaviors. Dynamic computational models use time-series measurements of simplified consortia.

FIG. 6A shows time-series measurements of relative abundance for each species in the full community compared to a consortium lacking EL. FIG. 6B shows quantitative metric of the total change in community structure for communities lacking each species.

(FIG. 15A) Schematic of a control experiment wherein E. coli MG1655 expressing RFP (EC) and S. typhimurium expressing YFP (ST) are encapsulated separately and then merged with RNA capture beads for subsequent RT-PCR and sequencing library preparation. (FIG. 15B) Number of EC and ST Unique Molecule Identifier (UMI) counts for each Unique Bead Identifier (UBI) in a first control experiment in which ExoI treatment was not applied. (FIG. 15C) Relationship between number of UBIs above a certain UMI Count threshold for varying bead number, when beads are used for RT-PCR of purified EC RNA with and without ExoI treatment after the RT reaction. The vertical line and numbered labels indicate the number of UBIs with at least 2 UMI counts. Gel images of the PCR products used to make these sequencing libraries are shown in FIG. 14. (FIG. 15D) Number of EC and ST UMI counts for each UBI in a second control experiment in which ExoI treatment was applied. (FIG. 15E) Number of EC and ST UMI counts for each UBI in a negative control experiment in which EC and ST were encapsulated together (ExoI treatment was applied).

FIG. 23A: EC RNA. FIG. 23B: SE RNA.

FIG. 24A: 1% agarose gel of PCR amplicons using EC and ST lysates. Lysates were obtained using the Lucigen QuickExtract RNA extraction kit supplemented with proteinase K and salt at different incubation temperatures. [1: Cell lysates containing total RNA from *E. coli* using lysis buffer comprising Lucigen QuickExtract lysis buffer and heated at 55° C. 2: Same as 1, but with 15 mM MgCl2, 0.5M NaCl and not heated, 3: Same as 1, but with 15 mM MgCl2 and 0.5M NaCl. 4: 2-log base pair ladder, 5: Same as 1, but from *S. typhimurium*, 6: Same as 2, but from *S. typhimurium*, 7: Same as 3, but from *S. typhimurium*] FIG. 24B: 1% agarose gel of PCR amplicons using EC or ST lysate. Cells were lysed using Bugbuster, SDS, and proteinase K at varying concentrations. [1: Cell lysates containing total RNA from *E. coli* using lysis buffer comprising 0.5% BugBuster, 0.3% SDS with 15 mM MgCl, 0.5M NaCl, and proteinase-K in TE buffer. 2: Same as 1, but with 0.2% SDS instead, 3: Same as 1, but with 0.3% BugBuster instead, 4: 2-log base pair ladder, 5: Same as 1, but from *S. typhimurium*, 6: Same as 2, but from *S. typhimurium*, 7: Same as 3, but from S. typhimurium]

FIG. 25A: Scatter plots of the UMI counts per UBI mapped to *E. coli* or *S. typhimurium*. FIG. 25B: Histogram showing the distribution of specificities.

DETAILED DESCRIPTION OF THE INVENTION

Figure 1A:
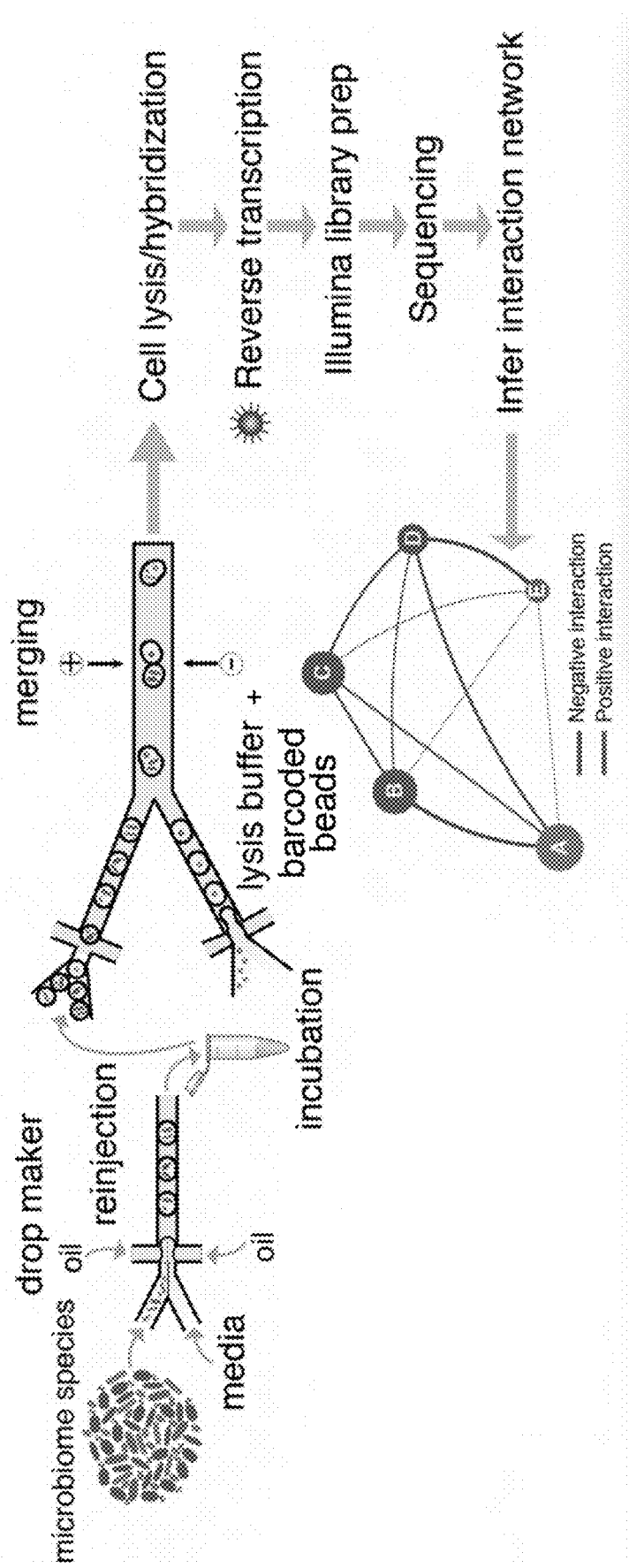
FIGS. 1A and 1B. Overview of an exemplary droplet-microfluidic platform for large-scale mapping of interactions in microbiomes.

One aspect of the invention comprises isolating one or more cells in a liquid droplet encapsulated by an immiscible medium.

The cells can comprise single-celled microorganisms or any cells from multi-cellular organisms. Exemplary microorganisms include bacteria, fungi (such as yeasts), protozoa, and algae. In some versions, the cells are fully dispersed. For example, cells originally present in biofilms or multi-cellular tissues may be dissociated into the individual cells. In some versions, the cells are only partially dispersed, such that subsets of cells adhering to each other can be isolated in a single droplet.

The isolated cells include a target nucleic acid comprising a target sequence and a cell identifier sequence. The target nucleic acid is any nucleic acid comprising a cell identifier sequence and can be DNA or RNA. Exemplary DNA includes genomic DNA, DNA on an extrachromosomal DNA construct (such as an extrachromosomal plasmid), viral DNA (from a virus contained within the cell), etc. Exemplary RNA includes messenger RNA (mRNA), ribosomal RNA (rRNA), viral RNA (from virus contained within the cell), etc.

The target sequence is a sequence in the target nucleic acid capable of hybridizing to a capture sequence under solution conditions of a merged droplet (the capture sequence and merged droplet are described in further detail below). Each target sequence among the isolated cells can be unique among those in each type of isolated cell, unique among those in a subset of the isolated cells, or substantially identical among those in the isolated cells. Versions of the invention employing unique target sequences can confer specificity in identifying cells at least in part by virtue of the specificity of a capture sequence binding to a particular, unique (within at least some set of cells) target sequence. However, versions of the invention preferred for high-throughput processing employ target sequences that are substantially identical among the isolated cells or even among any greater population of cells from which the isolated cells are isolated. "Substantially identical" as used herein with reference to sequences refers to a sequence identity of at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. "Identical" as used herein with reference to sequences refers to 100% sequence identity. In exemplary versions of the invention, the target sequences comprise conserved regions of 16S rRNA. The conserved regions of 16S rRNA are well known in the art and need not be described in detail herein. See, e.g., Větrovský et al., 2013; Weisburg et al, 1991; Coenye et al, 2003; Woese et al. 1977; Tsukuda et al., 2017; Gray et al., 1984; Yang et al., 2016; Bartram et al., 2011; Burke et al, 2016; Van de Peer et al., 1996; Chakravorty et al., 2007; and Jovel et al., 2016.

The cell identifier sequences are sequences in a region 5' to the target sequences on the target nucleic acids that permit distinguishing one type of cell from another based on a sequence difference in the regions of the cell types. In exemplary versions of the invention, the cell identifier sequences comprise variable regions of 16S rRNA. The variable regions of 16S rRNA are sometimes referred to as "hypervariable regions" and include the V1, V2, V3, V4, V5, V6, V7, V8, and V9 regions of 16S rRNA. The variable regions of 16S rRNA are well known in the art and need not be described in detail herein. See, e.g., Větrovský et al., 2013; Weisburg et al, 1991; Coenye et al, 2003; Woese et al. 1977; Tsukuda et al., 2017; Gray et al., 1984; Yang et al., 2016; Bartram et al., 2011; Burke et al, 2016; Van de Peer et al., 1996; Chakravorty et al., 2007; and Jovel et al., 2016.

The liquid droplet in which the cells are isolated is preferably an aqueous liquid droplet comprising water in an amount of at least about 5%, about 10%, about 20%, about 30%, about 40%, about 50%, about 60%, about 70%, about 80% or more by mass.

The immiscible medium is preferably a water-immiscible medium. The water-immiscible medium may comprise an oil. An exemplary oil is fluorinated oil, such as QX200™ Droplet Generation Oil for EvaGreen #1864005 (BioRad, Hercules, Calif.). Various surfactants present in the immiscible medium and or the liquid droplet may help to stabilize the liquid droplets within the immiscible medium.

The liquid droplets of the invention preferably have a volume of from about 1 pL to about 100 nL, such as a volume from about 10 pL to about 10 nL or from about 100 pL to about 1 nL. Amounts above and below these amounts are acceptable.

In some versions of the invention, no more than one cell is isolated in each liquid droplet. In other versions of the invention, more than one but no more than 2, 3, 4, 5, 6, 7, 8, 9, 10, 12, 13, 14, 15, 16, 17, 18, 10, 20, 25, or 30 cells are isolated in each liquid droplet. Accordingly, in various versions of the invention, each cell-containing droplet may comprise no more than 1, 2, 3, 4, 5, 6, 7, 8, 9, 10, 12, 13, 14, 15, 16, 17, 18, 10, 20, 25, or 30 cells at the time of isolation (i.e., prior to cell growth).

In some versions of the invention, cells from a diverse population of cells are isolated in sets in a number of liquid droplets such that the droplets contain different combinations of isolated types of cells. Accordingly, in some versions, the cell identifier sequence of at least one of the cells in at least one of the sets of cells is different from the cell identifier sequence of at least one other of the cells in at least one of the sets of cells. In some versions, the cell identifier sequence of the at least one of the cells in at least one of the sets of cells is not present among the cells in at least one other of the sets of cells.

Methods for isolating the one or more cells in the liquid droplet are described below in the examples.

Another aspect of the invention comprises incubating the liquid droplet containing the cells within the immiscible medium at a growth temperature for a period of time. "Growth temperature" refers to a temperature suitable for growth (i.e., division) of the isolated cells. Temperatures suitable for growth of various types of cells are well known in the art. For example, psychrophiles grow well between about −5° C. and about 20° C.; mesophiles grow well between about 20° C. and about 45° C.; and thermophiles grow well at temperatures above about 45° C. The period of time may comprise from 30 seconds to 48 hours or more. The liquid droplet containing the cells is preferably incubated until at least one cell contained therein grows beyond the amount originally isolated.

As outlined extensively in the examples, a given type of cell or combination of types of cells can have a particular effect on other types of cells or combination of types of cells. This effect can be inhibitory or stimulatory. Accordingly, in some versions of the invention, incubating the liquid droplet containing the cells can result in at least one of the cells in a given set affecting the growth of at least one other of the cells in the set.

Another aspect of the invention comprises merging cell-containing liquid droplets with one or more additional liquid droplets to thereby generate merged droplets. The merging can comprise merging in the context of a microfluidic system or can comprise combining in any other context. The additional liquid droplets can include oligonucleotides, a lysis reagent, or both. The merging occurs in such a manner that the merged droplets ultimately comprise the isolated cells, the oligonucleotides, and, optionally, the cell-lysis reagent. The merging can occur in a number of formats. In one format, the cell-containing liquid droplets are merged with liquid droplets comprising both the oligonucleotides and the cell-lysis reagent. In other formats, the cell-containing liquid droplets are sequentially or simultaneously merged with processing droplets comprising only the cell-lysis reagent and separate processing droplets comprising only the oligonucleotides. The format in which the cell droplets are merged with liquid droplets comprising both the cell-lysis reagent and oligonucleotides is preferred for processing efficiency. It is further preferred in this format that each cell-containing liquid droplet is merged with no more than one oligonucleotide-containing liquid droplet.

The lysis reagent merged with the cell may comprise a detergent. The detergent preferably comprises a non-denaturing detergent. The non-denaturing detergent preferably comprises a non-ionic detergent. Exemplary non-denaturing, non-ionic detergents include TRITON X-100 (Dow Chemical Company, Midland, Mich.) (4-(1,1,3,3-Tetramethylbutyl)phenyl-polyethylene glycol, t-octylphenoxypolyethoxyethanol, polyethylene glycol tert-octylphenyl ether), NP-40 (nonyl phenoxypolyethoxylethanol), NONIDET P-40 (Shell Chemical Co., The Hague, The Netherlands) (octyl phenoxypolyethoxylethanol), Tween 20, and others. The detergent is preferably present in the liquid droplet at a concentration of from about 0.5% v/v to about 5% v/v, such as a concentration of from about 1% v/v to about 5%. The lysis reagent may alternatively or additionally comprise a lytic enzyme. Exemplary lytic enzymes include lysozyme and phage lysins, among others. Suitable lysozyme concentrations of lysozyme include concentrations between about 1 kU/ml and 60 kU/ml, such as about 30 kU/ml. Concentrations above and below these amounts are also acceptable. Optimal concentrations of other particular lytic enzymes can be easily determined. A detergent should be sufficient to lyse most cells, particularly when heated. For cells with cell walls, such as certain types of bacteria, the lysis reagent preferably includes a detergent in addition to a lytic enzyme.

In some versions, oligonucleotide-containing liquid droplets may comprise the oligonucleotides and/or the lysis reagent within a salt-containing buffer. The salt containing buffer may comprise a salt. The salt in some versions is included in the salt-containing buffer in an amount from about 0.01 M, 0.025 M, about 0.05 M, about 0.075 M, about 0.1 M, about 0.25 M, about 0.5 M, about 0.75 M, or about 1 M to about 0.025 M, about 0.05 M, about 0.075 M, about 0.1 M, about 0.25 M, about 0.5 M, about 0.75 M, about 1 M, about 1.25 M, or about 1.5 M. The salt may comprise a metal salt. The metal salt may comprise a monovalent metal salt, a divalent metal salt, or a combination thereof. The monovalent metal salt in some versions is included in the salt-containing buffer in an amount from about 0.01 M, 0.025 M, about 0.05 M, about 0.075 M, about 0.1 M, about 0.25 M, about 0.5 M, about 0.75 M, or about 1 M to about 0.025 M, about 0.05 M, about 0.075 M, about 0.1 M, about 0.25 M, about 0.5 M, about 0.75 M, about 1 M, or about 1.25 M. The divalent metal salt in some versions is included in the salt-containing buffer in an amount from about 0.001 M, about 0.0025 M, about 0.005 M, about 0.0075 M, about 0.01 M, 0.025 M, about 0.05 M, about 0.075 M, about 0.1 M, about 0.25 M, about 0.5 M, about 0.75 M, or about 1 M to about 0.025 M, about 0.05 M, about 0.075 M, about 0.1 M, about 0.25 M, about 0.5 M, about 0.75 M, about 1 M, or about 1.25 M. Exemplary monovalent metal salts include sodium salts (e.g., NaCl), potassium salts (e.g., KCl), and lithium salts, among others. Exemplary divalent metal salts include magnesium salts (e.g., $MgCl_2$), calcium salts, and manganese salts, among others. The anion in the salt can be inorganic, such as chloride ($Cl^-$), or organic, such as acetate ($CH_3COO^{-2}$); and can be monatomic, such as fluoride ($F^-$), or polyatomic, such as sulfate ($SO_2^{-4}$ Exemplary anions include acetate ($CH^3COO^-$), carbonate ($CO_3^{2-}$), chloride ($Cl^-$), citrate ($HOC(COO^-)(CH_2COO^-)_2$), cyanide ($C\equiv N^-$), fluoride ($F^-$), nitrate ($NO_3^-$), nitrite ($NO_2^-$), oxide ($O^{2-}$), phosphate ($PO_4^{3-}$), and sulfate ($SO_4^{2-}$).

The oligonucleotides may include one or more of a priming sequence, a set identifier sequence, a molecule identifier sequence, and a capture sequence.

The priming sequences are sequences amenable to priming with a primer in a nucleic acid polymerization reaction and are preferably substantially identical among all the oligonucleotides. The priming sequence may comprise a sequence of an adapter or portions of an adapter suitable for use in next-generation sequencing, such as sequencing through use of the ILLUMINA (Illumina, Inc., San Diego, Calif.), ION TORRENT (ThermoFisher Scientific, Waltham, Mass.), or SOLID (Applied Biosystems, Foster City Calif.) platforms. The priming sequences preferably have the same length on each of the oligonucleotides.

The set identifier sequences are sequences that identify oligonucleotides present in a given set of oligonucleotides as distinct from those present in different sets of oligonucleotides. Each set of oligonucleotides are preferably those present in a single oligonucleotide-containing liquid droplet. The set identifier sequences among the oligonucleotides in each set of oligonucleotides are distinct from the set identifier sequences among the oligonucleotides in the other sets of oligonucleotides. The set identifier sequences among the oligonucleotides in each set of oligonucleotides are preferably substantially identical to each other. The set identifier sequences preferably have the same length on each of the oligonucleotides. Exemplary set identifier sequences are referred to in the following examples as "unique bead identifiers" (UBIs).

The molecule identifier sequences are sequences that identify a single oligonucleotide within the set of oligonucleotides in which the single oligonucleotide is comprised. Each molecule identifier sequence is preferably unique with respect to the other molecule identifier sequences in each given set of oligonucleotides (e.g., those having identical set identifier sequences), and, optionally, unique with respect to the molecule identifier sequences among all the oligonucleotides at large. The molecule identifier sequences preferably have the same length on each of the oligonucleotides. Exemplary molecule identifier sequences are referred to in the following examples as "unique molecule identifiers" (UMIs).

The capture sequences are sequences capable of hybridizing to a target sequence. In various versions, each capture sequence can be unique among the oligonucleotides, unique among a subset of the oligonucleotides, or substantially identical among the oligonucleotides. Versions of the invention employing substantially identical capture sequences are preferred for high-throughput processing. The capture sequence is preferably on the extreme 3' terminus of the oligonucleotides and, thus, 3' of the molecule identifier sequence and the set identifier sequence. This permits the capture sequence to serve as a primer that extends along a region of the target nucleic acid encompassing the cell identifier sequence. The capture sequences preferably have the same length on each of the oligonucleotides. In some versions, the capture sequence on each oligonucleotide is capable of hybridizing to the target sequence in the target nucleic acid of each of the isolated cells under the solution conditions of the merged droplets. In exemplary versions of the invention, the capture sequence is a sequence complementary, or at least hybrizable under solution conditions of the merged droplet, to a conserved region of 16S rRNA employed as a target sequence. As used herein, "complementary" means a sequence that is an exact reverse complement to a given sequence.

When any of a priming sequence, a set identifier sequence, a molecule identifier sequence, and a capture sequence are present on the oligonucleotides, such sequences are preferably arranged in the same order on each of the oligonucleotides.

The priming sequences, the set identifier sequences, the molecule identifier sequences, and the capture sequences may each independently have a length (i.e., number of bases) of from 2 to 50 bases or more. Accordingly, the priming sequences, the set identifier sequences, the molecule identifier sequences, and the capture sequences may each independently have a length greater than 2 bases, 3 bases, 4 bases, 5 bases, 6 bases, 7 bases, 8 bases, 9 bases, 10 bases, 11 bases, 12 bases, 13 bases, 14 bases, 15 bases, or more and up to 3 bases, 4 bases, 5 bases, 6 bases, 7 bases, 8 bases, 9 bases, 10 bases, 11 bases, 12 bases, 13 bases, 14 bases, 15 bases, 20 bases, 25, bases, 30 bases, 35 bases, 40 bases, 45 bases, 50 bases or more.

The oligonucleotides may be attached to solid substrates, such as beads. It is preferred that each oligonucleotide is attached to no more than one solid substrate. In some versions, the set identifier sequences of the oligonucleotides attached to each solid substrate in a given oligonucleotide-containing liquid droplet are substantially identical to each other and are different from the set identifier sequences of the oligonucleotides attached to solid substrates in other oligonucleotide-containing liquid droplets. In some versions, each oligonucleotide-containing liquid droplet contains no more than one solid substrate, wherein each solid substrate contains oligonucleotides with set identifier sequences that are identical to each other and are different from set identifier sequences on oligonucleotides attached to solid substrates in other oligonucleotide-containing liquid droplets. In this manner, merging the cell droplets with no more than one oligonucleotide-containing liquid droplet ensures that each of the oligonucleotides within a single merged droplet has the same set identifier sequence.

Another aspect of the invention comprises incubating the merged droplets within the immiscible medium. The incubating can comprise incubating at one or more constant temperatures for a given period of time. In some versions, lysis is performed by incubating the merged droplets at a temperature above 15° C., 20° C., 25° C., 30° C., 35° C., 40° C., 50° C., 60° C., 70° C., 80° C., 90° C., 100° C. or more for a period of about 5 seconds, about 1 minute, about 2 minutes, about 3, minutes, about 4 minutes, about 5 minutes, about 10 minutes, about 15 minutes, about 20 minutes, about 25 minutes, about 30 minutes or more or any ranges therebetween. In some versions, the hybridization is performed by incubating the merged droplets at a temperature less than about 70° C., 60° C., 50° C., 40° C., 30° C., 20° C., 15° C., 10° C., 9° C., 8° C., 7° C., 6° C., 5° C., 4° C., 3° C., 2° C., 1° C., 0° C., or less for a period of about 5 seconds, about 1 minute, about 2 minutes, about 3, minutes, about 4 minutes, about 5 minutes, about 10 minutes, about 15 minutes, about 20 minutes, about 25 minutes, about 30 minutes or more or any ranges therebetween. The incubating can to lyse the cells, hybridize the capture sequences to the target sequences to thereby generate a hybridized oligonucleotide, or lyse the cells and hybridize the capture sequences to the target sequences to thereby generate a hybridized oligonucleotide.

Another aspect of the invention comprises extending the hybridized oligonucleotides along the target nucleic acids serving as templates to thereby generate extended oligonucleotides. In the extending, the capture sequence may serve as a primer that extends along a region of the target nucleic acid encompassing the cell identifier sequence. Each extended oligonucleotide thereby comprises any of the sequences present in the original oligonucleotides, such as the priming sequence, set identifier sequence, molecule identifier sequence, and capture sequence, as well as a sequence complementary to the cell identifier sequence on the target nucleic acid, also referred to herein as a "cell identifier sequence." The extension can be accomplished by incubating the merged droplet with the hybridized oligonucleotides in the presence of polymerases. The polymerases can be present by virtue of being included in liquid droplets (such as the oligonucleotide-containing liquid droplets) merged with the cell-containing liquid droplets or merged with the merged droplets themselves. Depending on whether the target nucleic acid is an RNA or a DNA, the polymerase may be an RNA-dependent DNA polymerase, a DNA-dependent DNA polymerase, or a DNA- and RNA-dependent DNA polymerase. DNA-dependent DNA polymerases are enzymes that catalyze the replication of DNA from a DNA template. RNA-dependent DNA polymerases are enzymes that catalyze the production of DNA from a RNA template. RNA-dependent DNA polymerases are sometimes known as "reverse transcriptases." DNA- and RNA-dependent DNA polymerases are enzymes that have both DNA-dependent DNA polymerase activity and RNA-dependent DNA polymerase (reverse transcriptase) activity. The polymerase may be thermostable. The above-mentioned polymerases are well known in the art and are commercially available.

Once the extended oligonucleotides are generated, the extended oligonucleotides can be amplified. The amplification can be accomplished by combining all the extended oligonucleotides (preferably bound to a solid substrate) from all the merged droplets in a single processing solution and carrying out amplification with a DNA-dependent DNA polymerase. The amplification preferably amplifies at least the cell identifier sequence, the set identifier sequence, and the molecule identifier sequence. One of the primers in the amplification can anneal to the priming sequences on the extended oligonucleotides. Another of the primers in the amplification can anneal to a portion of the extended oligonucleotides 3' to the cell identifier sequence.

The amplified extended oligonucleotides can then be sequenced to thereby generate sequence reads of the extended oligonucleotides. Each sequence read preferably comprises each sequence read comprising a molecule identifier sequence read, a set identifier sequence read, and a cell identifier sequence read, wherein the molecule identifier sequence read is a sequence read of one of the molecule identifier sequences, the set identifier sequence read is a sequence read of one of the set identifier sequences, and the cell identifier sequence read is a sequence read of one of the cell identifier sequences. The sequencing can be performed by any method. Next-generation sequencing methods are preferred.

The sequence reads can then be analyzed to determine the identity, proportion, and/or absolute number of each type of cell present in the merged droplet either before or after incubation, if performed. This can provide information on any effects one or more types of cells might have on the growth of other types of cell. This can also provide information on the types of cells that associate or adhere to each other in various contexts (i.e., in biofilms, microbiomes, environments (blood, lymph, etc.), or other contexts).

In some versions, the analysis comprises associating a cell identifier sequence read with a molecule identifier sequence read to thereby identify the isolated cell by its cell identifier sequence. In some versions, the analysis comprises grouping the cell identifier reads into groups of statistically identical cell identifier reads and determining a number of unique molecule identifier sequence reads associated with each group of statistically identical cell identifier reads. In some versions, the analysis comprises grouping the sequence reads into groups of sequence reads comprising statistically identical set identifier sequence reads; grouping, within each group of sequence reads, the cell identifier reads into groups of statistically identical cell identifier reads; and determining, within each group of sequence reads, a number of unique molecule identifier sequence reads associated with each group of statistically identical cell identifier reads. As used herein, "statistically identical" as applied to two sequence reads refers to sequence reads that are deemed to arise from identical sequences by accounting for sequencing errors or other errors. Methods for determining sequence reads that arise from identical sequences by accounting for sequencing errors or other errors are well known in the art. See, e.g., Smith et al., 2017.

As used herein, the terms "target sequence," "cell identifier sequence," "set identifier sequence," "capture sequence," and "molecule identifier sequence" refers generally to a nucleic acid sequence and its reverse complement unless the context dictates otherwise.

As used herein, the term "among" encompasses the term "between" unless otherwise specified or clearly implied to the contrary by the specific context in which the term is employed.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

Examples

Overview of Droplet-Microfluidic Technologies for Large-Scale Mapping of Microbial Interactions Droplet microfluidics is a technology to perform ultra-high-throughput biological assays by encapsulation in water-in-oil microemulsions (Guo et al., 2012). Using this method, cells can be compartmentalized in picoliter (pL) monodispersed (less than 1% size variation) droplets, allowing for sampling of millions of microbial assemblages in parallel. Integrated microfluidic devices enable automated droplet formation, manipulation, analysis and sorting at kilohertz rate. This technology is functionally similar to robotic liquid handling and analysis tools, but provides an orders-of-magnitude increase in throughput. This powerful technology can be applied to interrogate microbial interactions in high-dimensional microbiomes. High-throughput microfluidic technologies enables scalable exploration of microbial interactions with significantly greater depth than was previously possible using microtiter plates, and coupling microbial droplet encapsulation to next-generation sequencing allows for scalable interrogation of microbial interactions.

Figure 1B:
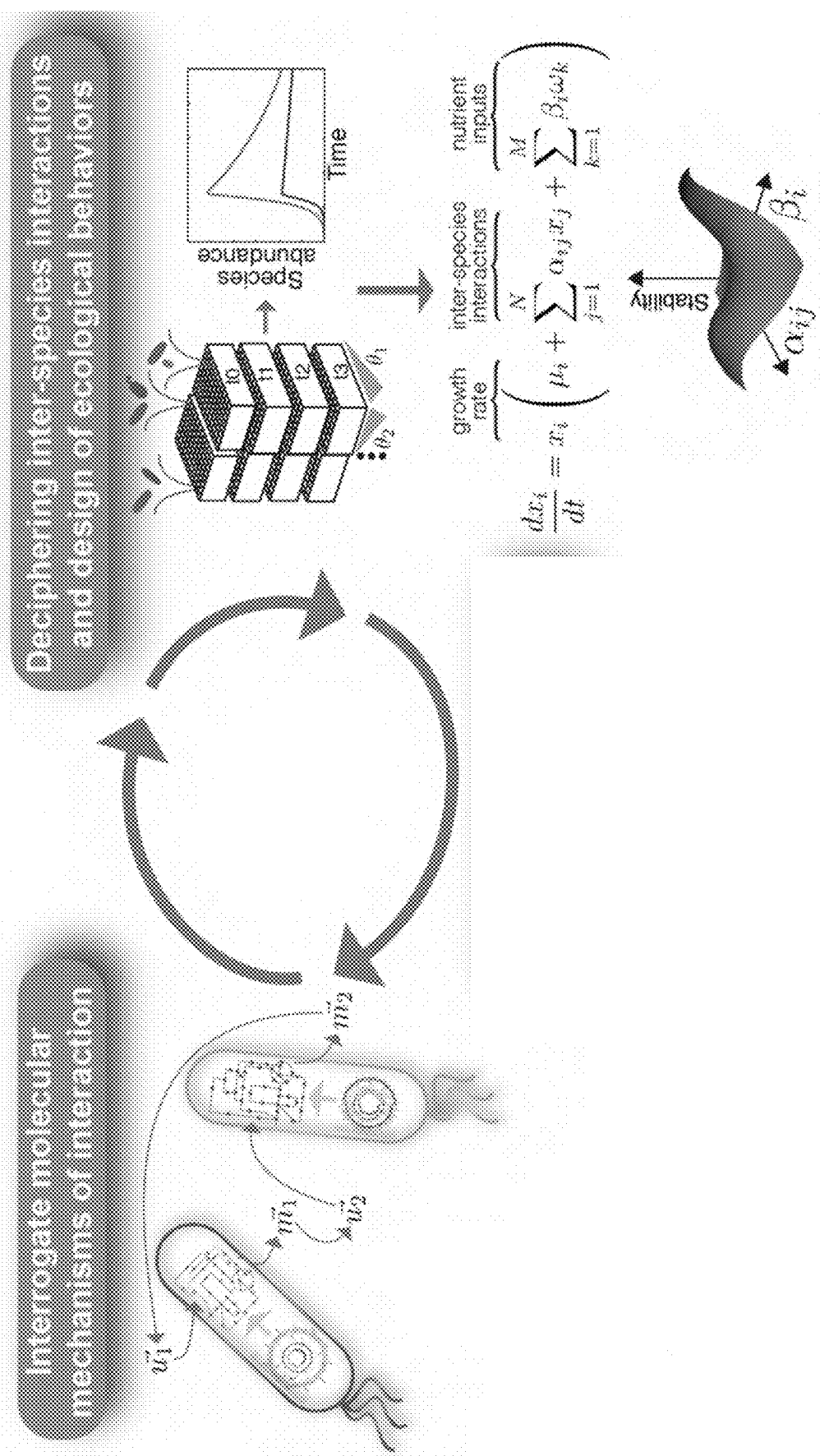

The present example provides a model-guided platform to interrogate the molecular and ecological basis of community-level functions of microbiomes. Methods are employed to analyze large-scale microbial interactions using droplet-microfluidics technologies (FIG. 1A). The methods can be leveraged, for example, to interrogate microbial interactions in microbiomes. The inferred microbial interaction network is used to down-select stable sub-communities for detailed temporal characterization in response to environmental shifts. Population dynamic models are constructed to represent growth, microbial interactions and coupling of microbial fitness to specific environmental stimuli (FIG. 1B). Barcoded transposon libraries can be constructed for highly influential species to pinpoint the genetic determinants underlying community behaviors. A detailed and mechanistic understanding of community-level properties can have profound implications on the ability to remodel the microbiome to improve human health.

Exemplary Droplet-Microfluidic Platform for Large-Scale Mapping of Interactions in the Human Gut Microbiome An exemplary platform for large-scale mapping of microbial interactions is shown in FIG. 1A. The approach uses a high throughput emulsion-based assay to probe interactions between hundreds of individual species. Members of a complex microbial ecosystem are encapsulated into millions of picoliter droplets. Each droplet contains 1-3 randomly encapsulated species based on Poisson statistics, and are incubated under various environmental conditions. The composition of each droplet is analyzed using next-generation 16S sequencing. The interactions are assessed by comparing the frequency of species co-occurrence with a non-interacting null model. The combination of emulsion-based assays and next-generation DNA sequencing allows performing millions of individual experiments, and therefore enables analysis of all pairwise and higher-order interactions among hundreds of microbial species. Picoliter water-in-oil emulsions are generated, processed, and analyzed using droplet-based microfluidic technology.

Figure 2:
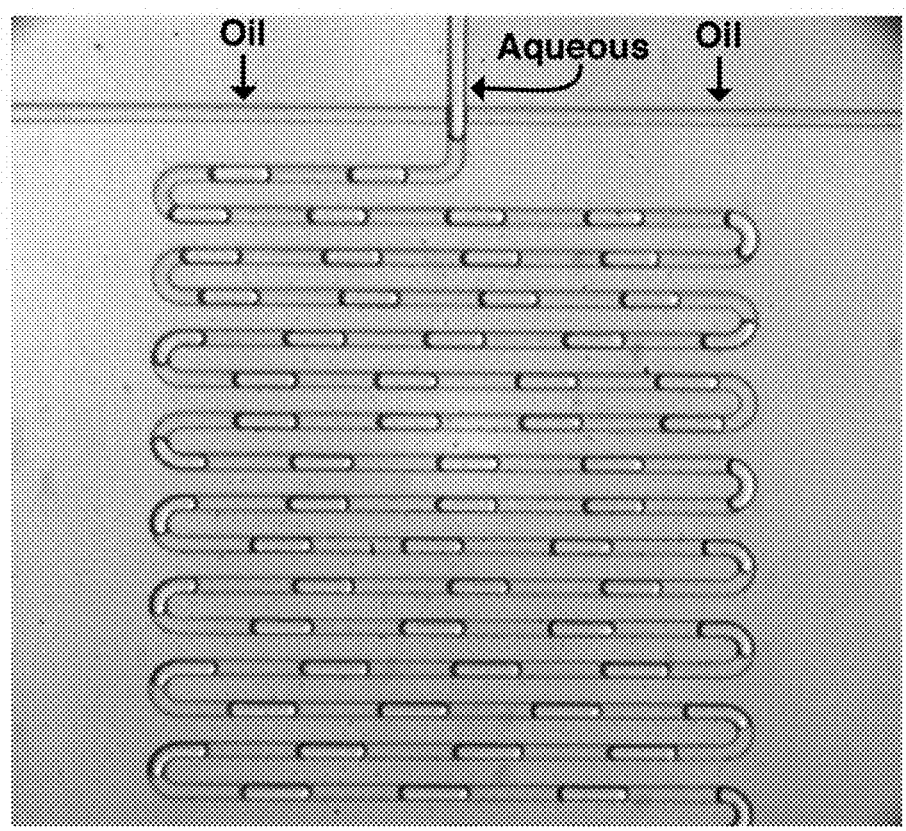
FIG. 2. Microscopy image of a droplet-maker microfluidic device. Water (aqueous phase) and oil are injected into a microfluidic junction, generating monodispersed water drops.

Droplets are formed by injecting an oil stream and an aqueous stream into a confined microfluidic junction (FIG. 2). This method generates thousands of highly monodisperse water droplets per second. The droplet volume and generation frequency can be easily tuned by adjusting the oil and aqueous flow rates. A fluorinated oil (HFE-7500) can be used to minimize interactions with biological samples, and a biocompatible surfactant can be used to stabilize the droplets against coalescence. Aspects regarding droplet-based microfluidics that can be employed in the present invention are described in Romero et al., 2015, and Romero and Abate, 2012. The microfluidic devices can be built according to known techniques, using photomask printing, lithography, polydimethylsiloxane (PDMS) molding and bonding, device surface treatment, etc.

A sample containing a microbial ecosystem is loaded onto a microfluidic drop-making device, and cells are randomly encapsulated into emulsion droplets. It is preferred to aim to encapsulate one cell per droplet on average, which will result in ~37% empty drops, ~37% single cells, ~26% multiple cells, according to Poisson statistics. The emulsion droplets are collected into a tube and incubated, allowing the encapsulated cells to grow for hours to days under desired conditions. Next, the droplets are reinjected onto a microfluidic merging device that pairs a cell droplet with a droplet containing lysis reagents and a DNA-barcoded bead. A focused high-voltage electrode can disrupt the surfactant interface between these two droplets and cause a merging event. Droplet merger can occur at ~1 kHz. At this rate, at least 3.6 million drops can be processed per hour The microparticles and oligonucleotides can be synthesized by ChemGenes Corporation (Wilmington, Mass.) or any of a number of other commercial vendors. Each microparticle preferably contains oligonucleotides with the following regions in order from the 5' end to the 3' end: (1) spacer region attached to the bead; (2) a 5' sequence used as a common primer annealing region; (3) a unique bead identifier (UBI), which is an ~8-12 bp random sequence specific to each bead; (4) a unique molecule identifier (UMI), an ~8-12 random sequence specific to each oligonucleotide, for digital abundance quantification; and (5) a targeting sequence (~20 bp) for capturing the V3/V4 region of the 16S rRNA. The bead barcode allows associating microbial contents of each droplet and extracting relative and absolute (based on the number of unique UMI sequences) abundance of the microbes in each droplet. The number of unique UMI sequences per UBI is proportional to the total amount of 16S rRNA and this quantity should correlate with microbial growth rates.

After merging, the cells lyse within the droplets. The droplets containing the lysed cells and DNA-barcoded beads are then cooled, allowing 16S RNA to hybridize to the DNA capture region on the bead. The emulsions containing the hybridized 16S rRNA are then coalesced using a surfactant-disrupting agent such as perfluorooctanol. The beads are washed several times before performing reverse transcription (cDNA synthesis), ExoI treatment, and PCR amplification. In the reverse transcription, the targeting sequences bound to the 16S rRNAs serves as primers that extend along the 16S rRNAs into the V3/V4 regions. ExoI reaction serve to remove unextended oligonucleotides on barcoded beads to prevent usage as primer for amplification in PCR. Any other single-strand DNA exonuclease, particularly those that degrade single-stranded DNA in a 3'→5' direction, can be used in place of or in addition to ExoI. Examples include RecJ, ExoVII, and SbcCD The PCR reactions generate amplicons that link the UBI to the 16S V3/V4 sequence. Next, the emulsions are coalesced, the DNA amplicons are purified, and next-generation sequencing adaptors (e.g., Illumina) are ligated onto the 5' and 3' ends of the amplicons. Sequencing of the sample provides a mapping between bead barcodes and species, which can be assembled to infer the relative proportions of species that were present in each approximately million picoliter droplets. Both positive and negative interactions can be identified by comparing the observed covariance patterns to a null model that assumes no inter-species interactions (see the following example). The null model accounts for the initial abundance of each species. The initial community structure is determined by next-generation sequencing of the full community prior to droplet encapsulation.

Network Inference and In-Silico Design of Stable Sub-Communities for Temporal Characterization Data analysis pipelines decipher microbial interactions based on the frequencies of species co-variation across drops. Specifically, the frequencies of pairwise species co-presence or co-exclusion are analyzed using an ensemble of distance metrics such as correlations, hypergeometric distribution and mutual information (Faust and Raes, 2012). These distance metrics are compared to a randomly permuted null model that accounts for the initial species abundances in the community. Statistical significance values compared to the null model are used to score the strength of predicted relationships between species. Beyond pairwise interactions, regularized regression methods and cross-validation are used to pinpoint higher-dimensional relationships among combinations of species. Using the inferred network, the node degree distribution and hub nodes are analyzed to highlight potential "keystone" species that exhibit a disproportionately large influence on the network. The modularity of the network is examined by identifying organism clusters that are densely connected within a group and sparsely linked to external groups (Clauset et al., 2004). Species are scored by their total positive or negative impact on the network, illuminating potential species that operate as global ecosystem enhancers or antagonists.

A combination of network analysis and dynamical systems modeling is used to analyze the stability of sub-community "clusters" identified by network analysis. To analyze stability, a generalized Lotka-Volterra (gLV) model that approximates inter-species interaction parameters is constructed using the inferred interaction network. In the absence of inter-species interactions ($\alpha_{ij}=0$), the gLV growth parameters are derived from time-resolved absorbance data (OD600) of monospecies. The inter-species interaction parameters are approximated based on the pairwise interaction network. In some cases, the directionality of a strong positive interaction can be extracted using a quantitative comparison between the frequencies of the pairwise assemblage and monospecies across samples. When directionality cannot be determined, equal interaction coefficients ($\alpha_{ij}$ and $\alpha_{ji}$) are assumed. Using these initial approximated models, stability, species co-existence (diversity), and the number of stable equilibria are analyzed. Network analyses and optimization methods are used to design a set of sub-communities that satisfy the following criteria: (1) span the genetic diversity of the gut microbiota by containing at least three distinct phyla; (2) contain a balance between significant negative and positive interactions previously shown to enhance community stability (Coyte et al., 2015); (3) include at least one butyrate-producing species; and (4) exhibit at least one stable equilibria that exhibits non-zero abundance of all constituent members (stable coexistence).

Validation of Generalizable Framework for Data-Driven Modeling of Microbial Community Dynamics The present example shows a generalizable framework to build data-driven population dynamic models of microbial communities from time-series data.

A simplified (12-member) human gut microbiome synthetic ecology that included the following species was studied: *Bacteroides thetaiotaomicron* (BT), *Bacteroides ovatus* (BO), *Bacteroides vulgatus* (BV), *Bacteroides uniformis* (BU), *Eubacterium rectale* (ER), *Collinsella aerofaciens* (CA), *Desulfovibrio piger* (DP), *Blautia hydrogenotrophica* (BH), *Prevotella copri* (PC), *Clostridium hiranonis* (CH), *Faecalibacterium prausnitzii* (FP) and *Eggerthella lenta* (EL). These organisms represent a broad functional and phylogenetic diversity, are prevalent across individuals (Qin et al., 2010) and include primary fermenters that break down complex dietary polysaccharides (*Bacteroides* spp.), secondary fermenters (*E. rectale, C. aerofaciens*), and several H2 consuming organisms (*D. piger, B. hydrogenotrophica*). Several of these species have also been implicated in disease states (Scher et al., 2013; Thota et al., 2011; Fujimoto et al., 2013).

Specific combinations of species were arrayed into 96-well plates and samples were collected for genome extraction approximately every 12 hr over a period of 3 days. The community was transferred to a fresh media environment (1:20 dilution) approximately every 24 hr to mirror dietary perturbations via periodic shifts in nutrient availability. The dual-indexed primers amplify a ~466 bp variable region of the 16S rRNA (V3/V4) and contain 5' adaptors necessary for sequencing on Illumina platforms. The set of 96 forward and 48 reverse indices permit multiplexed sequencing of 4,608 unique conditions. In addition to measuring community structure relative abundance, we monitored the total biomass of each community as a function of time to compute absolute species abundance. Absolute abundance information is critical for model parameterization (Lovell, 2015). Indeed, compositional data can lead to spurious correlations (Friedman et al. 2012) and an infinite set of models can represent relative abundance.

Figure 3:
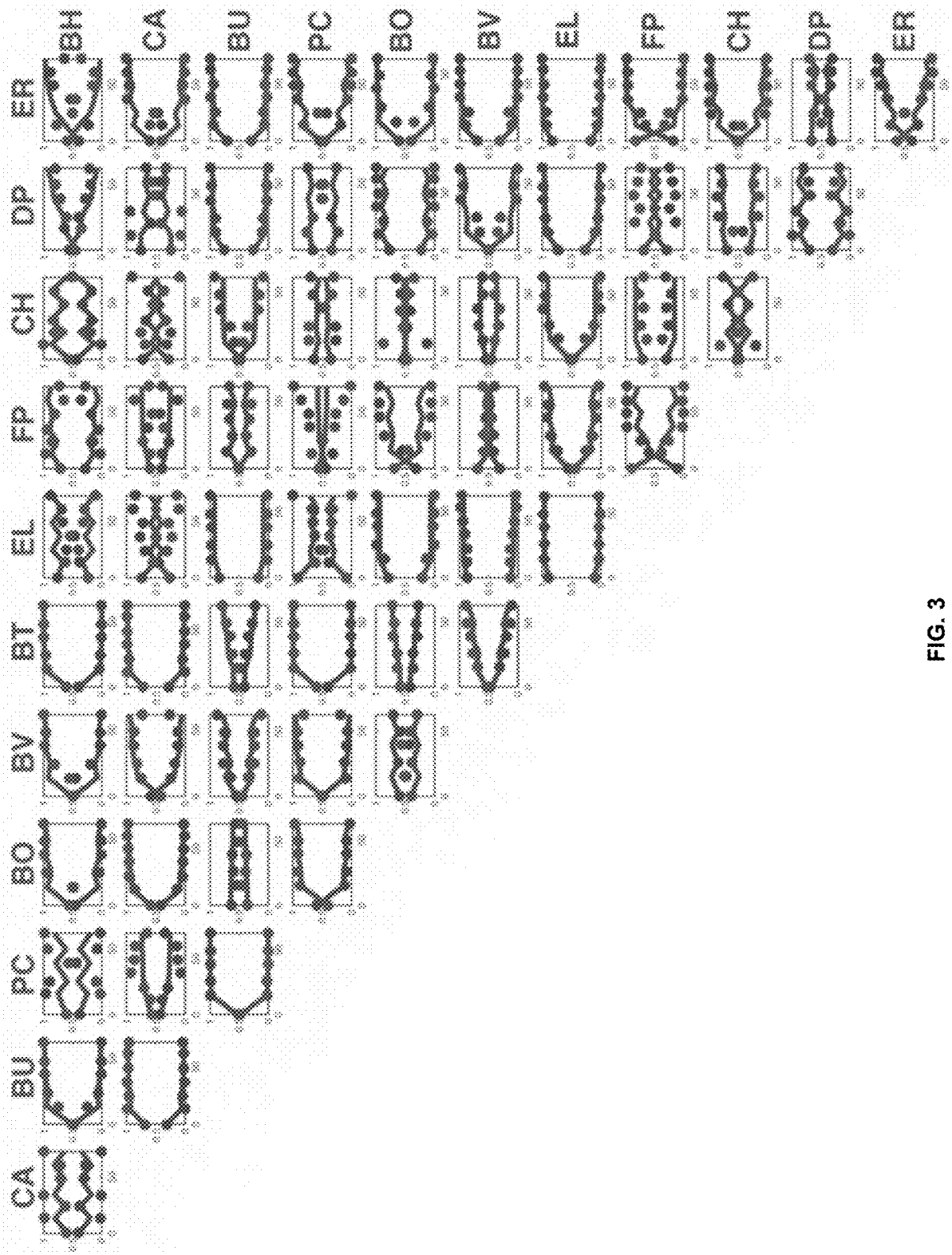
FIG. 3. Comparison between model prediction and time-series experimental data for pairwise assemblage of a microbes in a simplified 12-member human gut synthetic ecology with the following species: *Bacteroides thetaiotaomicron* (BT), *Bacteroides ovatus* (BO), *Bacteroides vulgatus* (BV), *Bacteroides uniformis* (BU), *Eubacterium rectale* (ER), *Collinsella aerofaciens* (CA), *Desulfovibrio piger* (DP), *Blautia hydrogenotrophica* (BH), *Prevotella copri* (PC), *Clostridium hiranonis* (CH), *Faecalibacterium prausnitzii* (FP) and *Eggerthella lenta* (EL). Each subplot represents time (x-axis) vs. relative abundance (y-axis). Data points and lines represent experimental measurements and model predictions, respectively.

Using a set of community and monospecies measurements, we developed a modeling framework to infer the parameters of the generalized Lotka-Volterra model. See Venturelli et al., 2018, which is incorporated herein by reference in its entirety. First, an initial guess was computed using linear regression by transforming the non-linear model into a linear equation (Mounier et al., 2008; Stein et al., 2013). Second, this initial solution was used as a starting point to a nonlinear optimization using subsets of the data for model training and the remaining fraction as a validation set. To minimize over-fitting and identify a sparse and predictive solution, we leveraged a regularized parameter estimation method using the L1-norm that balanced the model fit with the magnitude of the parameter values. Our data sets included time-series measurements of monospecies, all pairwise assemblages (66 combinations, FIG. 3), an informative collection of 3-6 member communities and leave-one-out communities (11-member) including the full community.

Figure 4A:
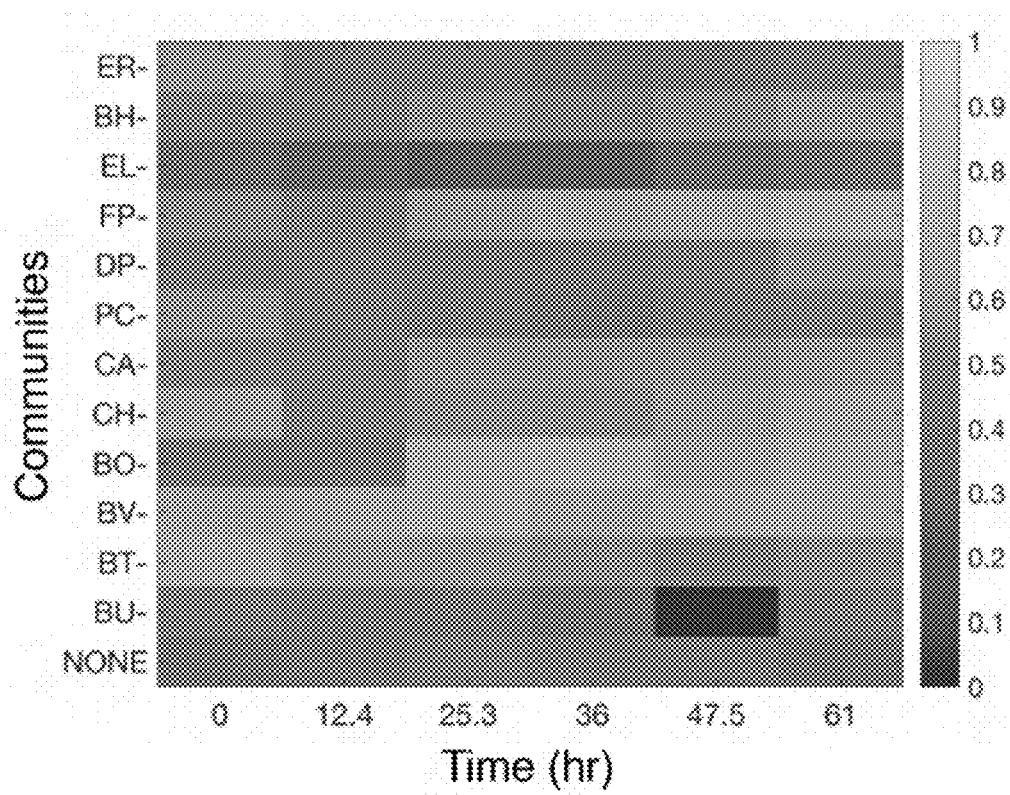
FIGS. 4A-4E. Heat-maps of Pearson's correlation coefficient between the relative abundance in an exemplary model of microbial community dynamics and experimental data using different model training sets. Organisms excluded from the community are denoted by X- (e.g. ER-denotes a community containing all species except ER) and "NONE" indicates the full community. Correlation coefficients across time in hr (x-axis) and communities (y-axis). The model was parameterized on (FIG. 4A) monospecies only, (FIG. 4B) monospecies and pairwise assemblages, (FIG. 4C) monospecies, pairwise assemblages and 20 three-member communities, (FIG. 4D) monospecies, pairwise and 24 three- to six-member consortia and (FIG. 4E) monospecies, pairwise and EL-.
Figure 4B:
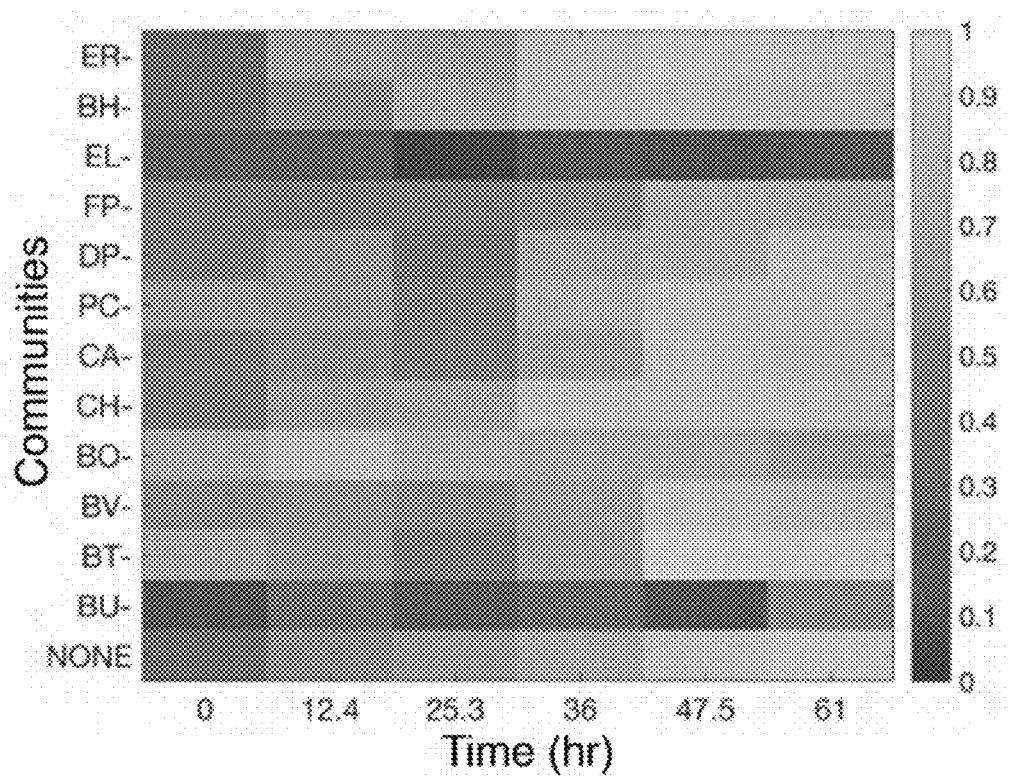
Figure 4C:
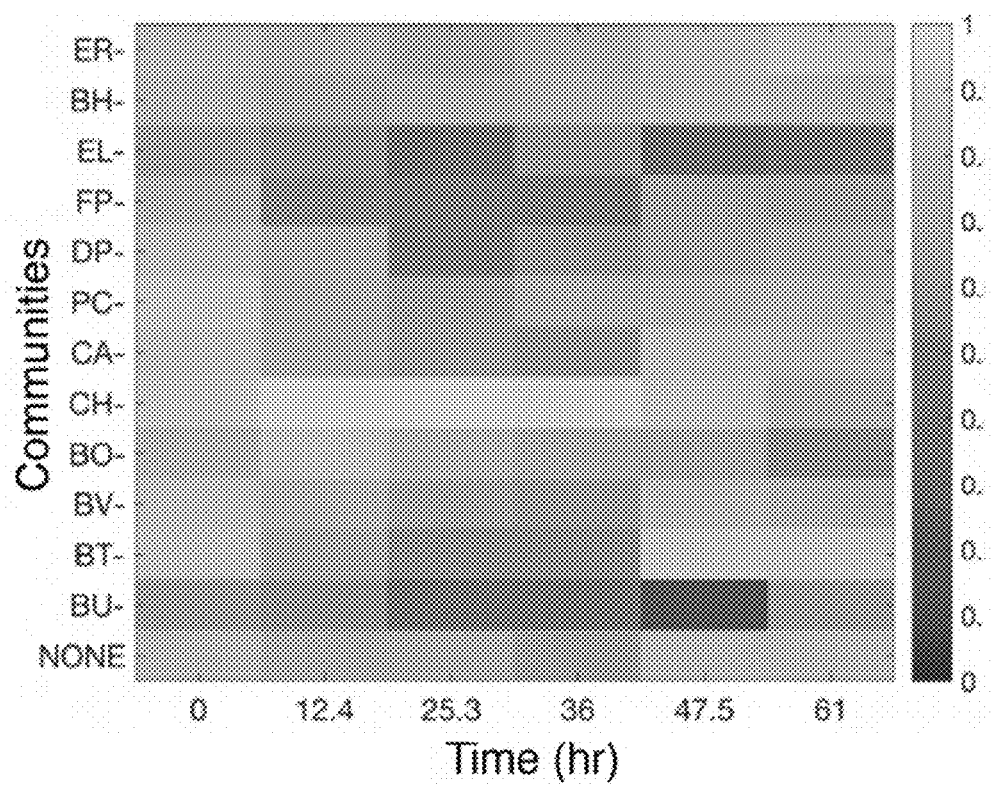
Figure 4D:
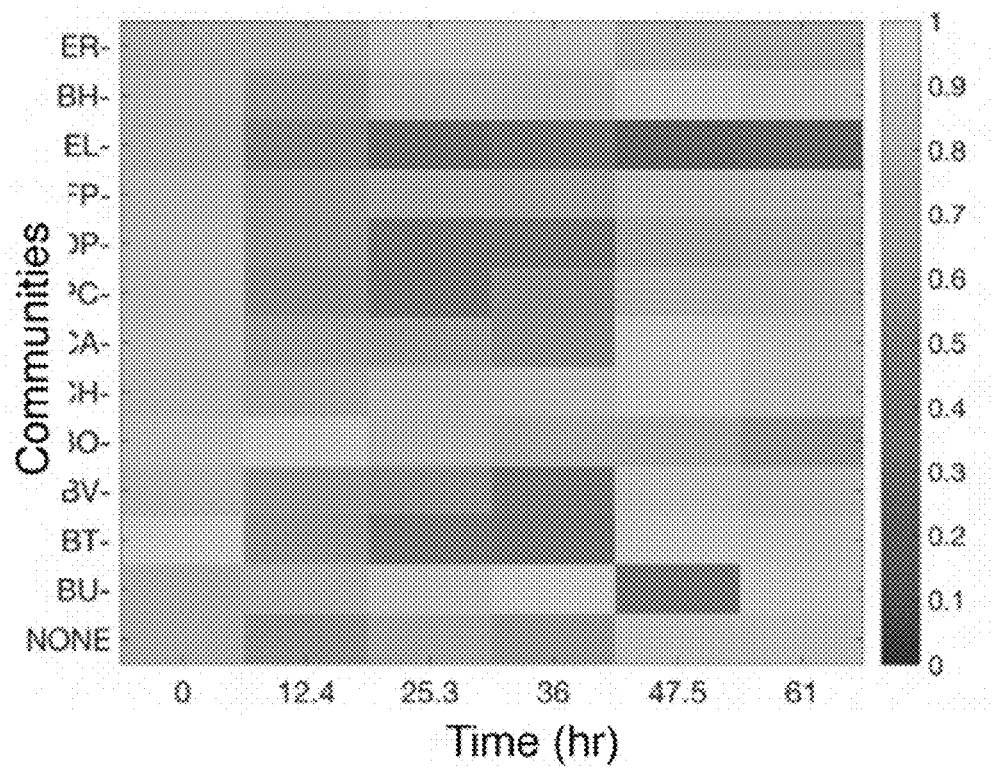
Figure 4E:
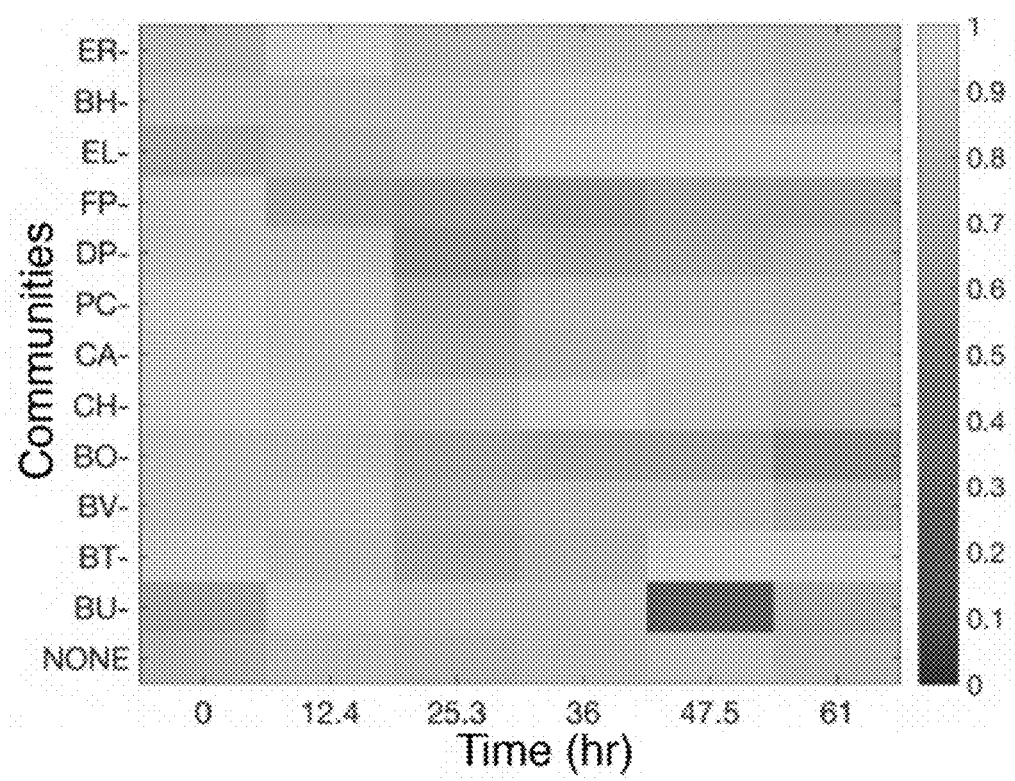

To evaluate the predictive capability of the model, the model was parameterized to lower-order species and used to predict the dynamics of the most complex subcommunities—the full community and leave-one-outs. Parameterization of the model using monospecies growth responses did not yield a predictive model, suggesting that microbial interactions significantly influence community assembly (FIG. 4A). Combining the monospecies and pairwise community data sets into the modeling fitting pipeline generated a model that could accurately predict the final stage of growth, but poorly represented the earlier stages of community assembly (FIG. 4B). Incorporating multi-species communities into the model training process significantly improved the prediction of transient community assembly, illustrating higher-order data can augment the predictive capability of the model (FIGS. 4C-4E). In sum, these results highlighted that a pairwise model was able to accurately capture the assembly dynamics of complex multi-species assemblages.

Figure 5:
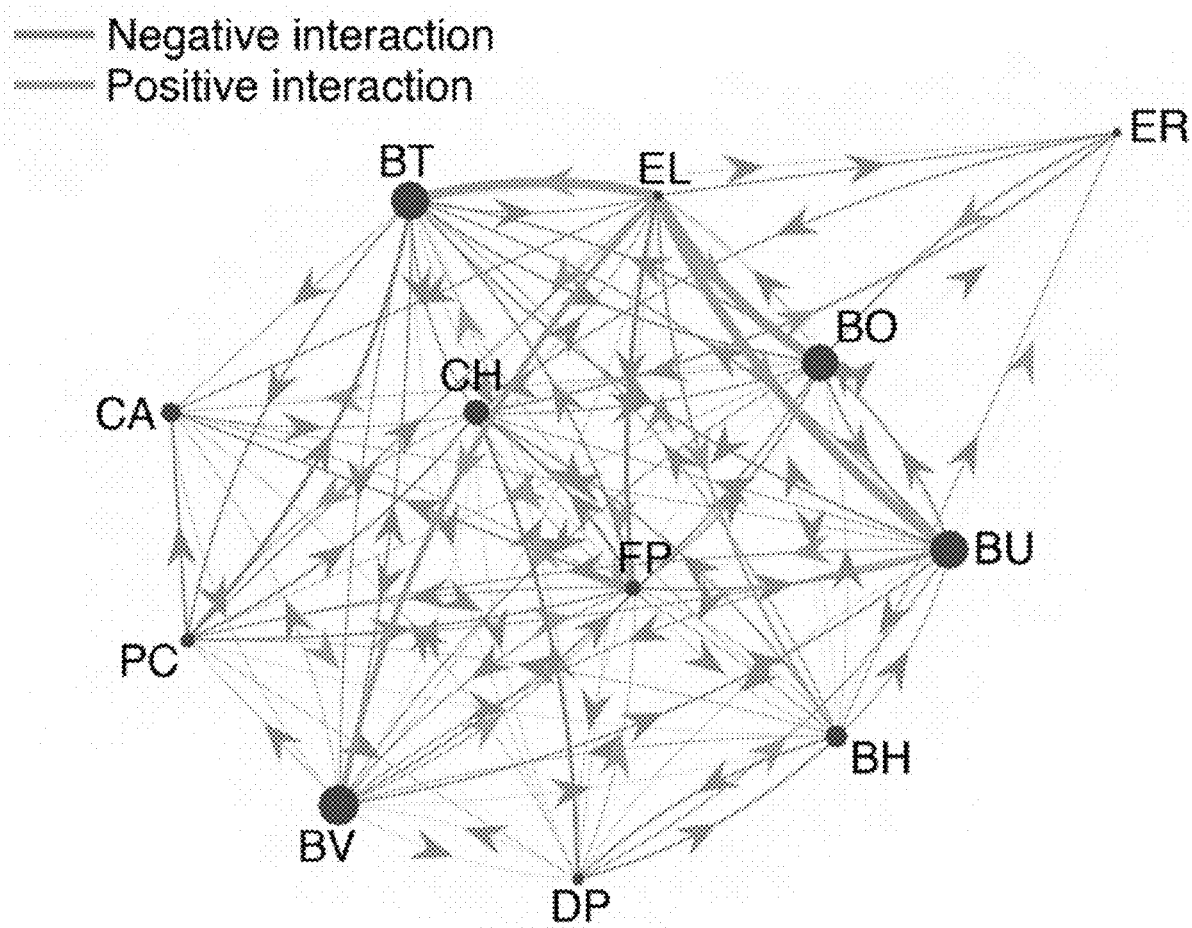
FIG. 5. Inter-species interaction network highlighting positive (green) and negative (red) interactions between human gut microbiome species. The width of the edge is proportional to the inter-species interaction strength. The size of the node denotes the carrying capacity of the monospecies.
Figure 6A:
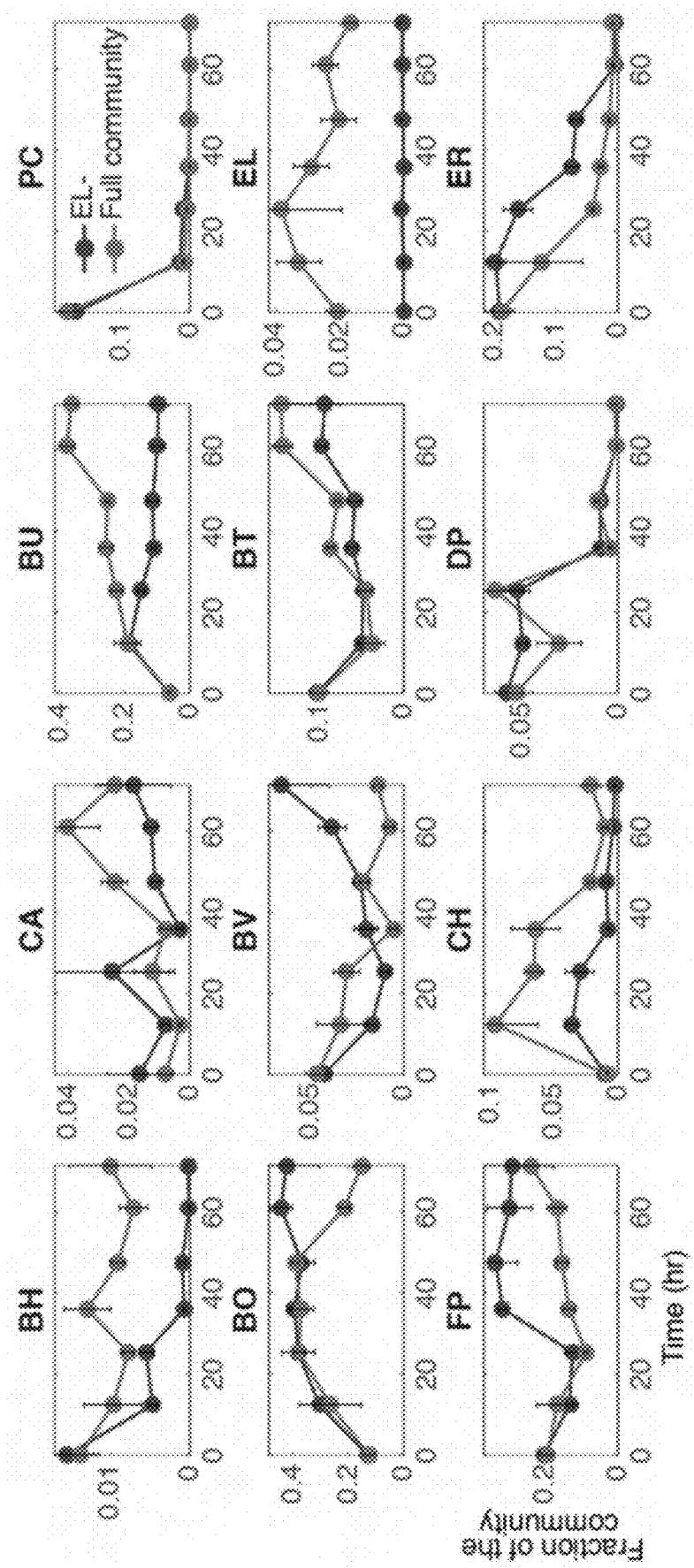
FIGS. 6A and 6B. *E. lenta* (EL) significantly impacts multi-species community assembly.
Figure 6B:
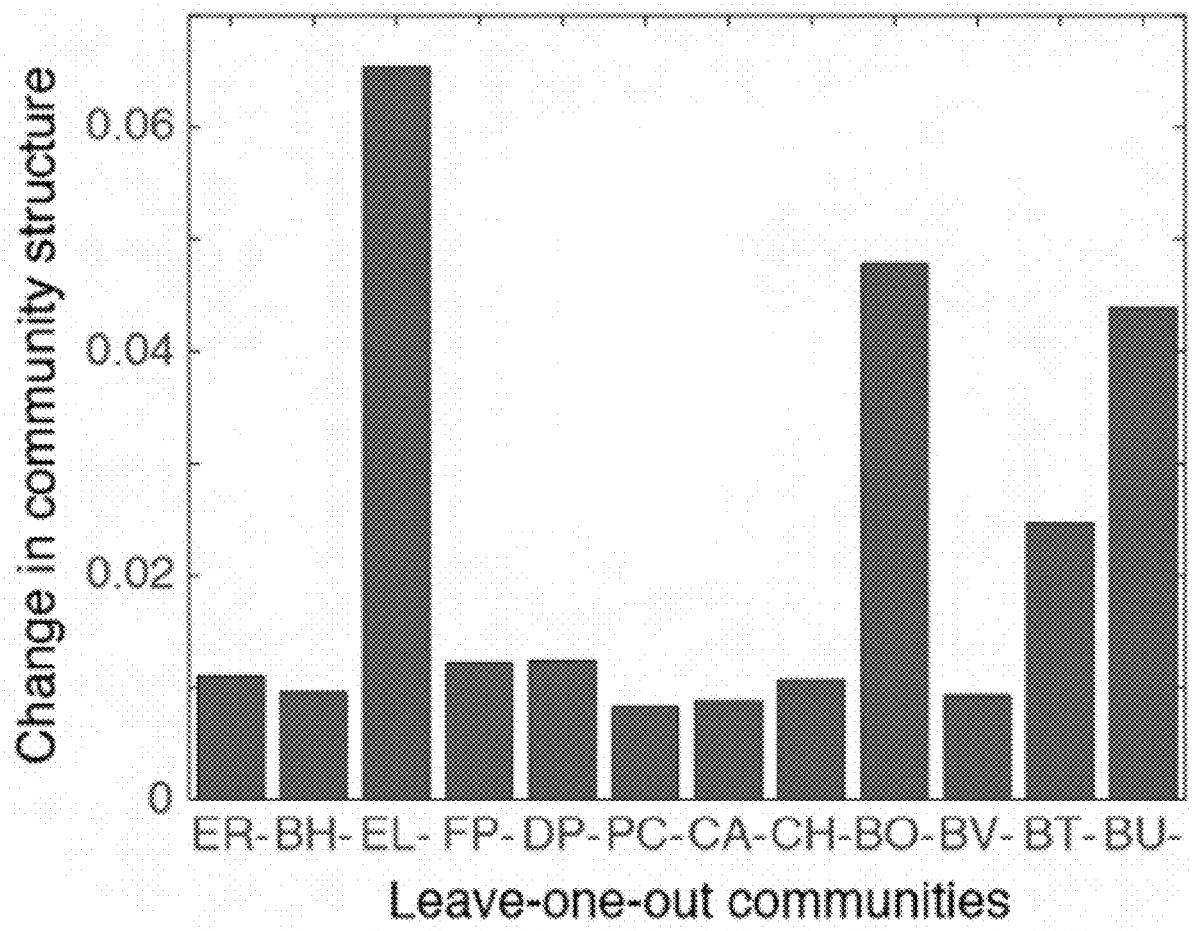

The inferred microbial interaction network based on the model showed that an Actinobacteria EL had the largest number of positive outgoing edges (FIG. 5). Further, the absence of EL significantly altered community assembly dynamics, highlighting that EL was a "keystone" species (FIGS. 6A and 6B). The butyrate-producing species FP was stimulated by the largest number of species in the network. Indeed, the fitness of FP was significantly enhanced by ecological interactions in the full community. *Bacteroides* spp. had an overall negative impact on the network.

To interrogate potential metabolites mediating inter-species interactions, we performed exo-metabolomic profiling of monospecies using liquid-chromatography mass spectrometry (LC-MS). In some cases, the exo-metabolomics predicted metabolites potentially involved in inter-species interactions. For example, FP was a predominantly a consumer of secreted metabolites, corroborating the significant enhancement of the fitness of FP in the context of the full community. Another butyrate producer ER operated as a consumer of secreted metabolites. In sum, these results suggest that ecological interactions are major variables that impact the stability and activity of butyrate producers.

Figure 7:
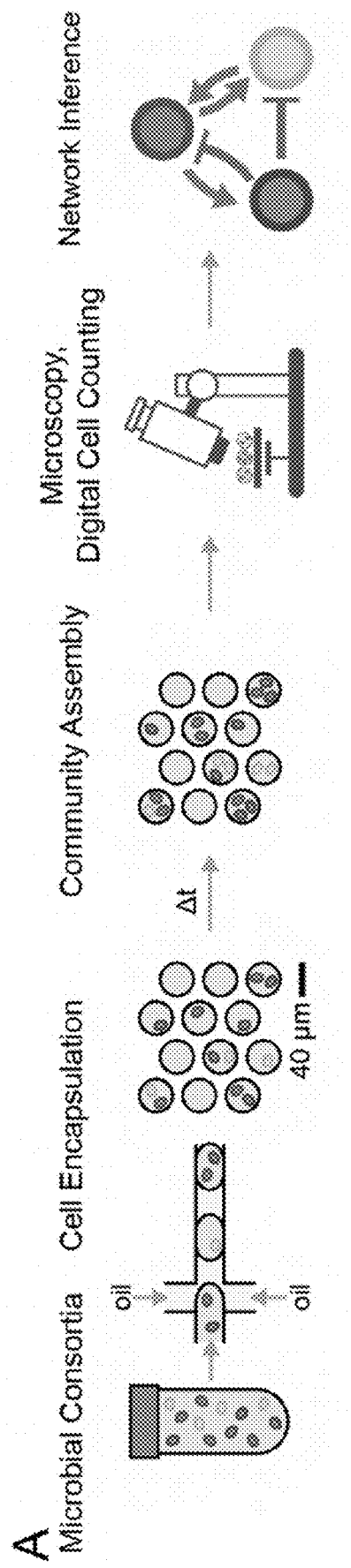
FIG. 7. A schematic of a method of deciphering microbial interaction networks by randomly encapsulating cells in droplets and detecting the encapsulated cells using microscopy.

Deciphering Microbial Interaction Networks by Randomly Encapsulating Cells in Droplets and Detecting Encapsulated Cells Using Microscopy Summary The present example demonstrates deciphering microbial interaction networks by randomly encapsulating cells in droplets and detecting the encapsulated cells using microscopy. A schematic of the microbial interaction mapping pipeline is shown in FIG. 7. A microbial consortium and oil are loaded into a droplet-forming microfluidic device. Cells are encapsulated into droplets based on a Poisson distribution. The cells in droplets are incubated for a period of time to allow cell growth, metabolite secretion, uptake and cell division. The droplets are imaged using fluorescent microscopy and the number of cells is determined using a computational image analysis workflow. From these data, the microbial interaction network is inferred.

| | | Strains | | |
|---|---|---|---|---|
| Species | Genotype | Plasmid | Fluorophore | Abbreviation |
| B. subtilis | B. subtilis 168 | None | GFP | BS Trp- |
| E. coli | K12 BW25113ΔMetA ΔLacZ | pOSV005 | RFP | EC Met- Lac* and EC Met- |
| E. coli | LuxI | pOSV022 | GFP | Sender |
| E. coli | E. coli MG1655z1 | pOSV151 | RFP | Receiver |
| E. coli | K12 BW25113 ΔMetA | None | CFP | EC Met- |
| S. typhimurium | LT2 | None | YFP | ST Lac* |
| E. coli | wildtype | pOSV006 | RFP | EC WT |

Strain Pre-Culture

Strains were grown overnight at 37° C. in LB medium, diluted 1:50 into LB, and grown to exponential phase (OD600 0.3-1.0). 3 mL of culture was pelleted by centrifugation at 3,500×g for 2 minutes and supernatant was removed. The cells were washed four times by resuspending into 0.5 mL of the indicated medium, centrifuging at 3,500×g for 2 minutes, and removing the supernatant. The cell suspensions were normalized to 0.15 OD and mixed in a 1:1 ratio. In two-member mutualism experiments, B. subtilis and E. coli were mixed in a 2:1 ratio to account for differences in cell number to OD ratios. Inducers and antibiotic were added as indicated.

Dynamic Range of Cell Counting

EC Met- (CFP), EC WT (RFP), and ST WT (YFP) were grown in LB medium to early stationary phase, washed once and then resuspended to higher cell density in M9 minimal medium without glucose (OD600 of 14.4, 19.6, and 6.4, respectively). Equal volumes of each culture were mixed together to form the concentrated consortium. Serial dilutions by a factor of 2 were performed on this sample until a dilution of $2^{-7}$ was reached. Each dilution was encapsulated separately using the droplet-forming device and the resulting droplets were imaged and quantified using the image analysis pipeline.

Media

In two-member crossfeeding experiments, M9 Glucose (lx M9 Salts, 2 mM $MgSO_4$, 100 μM $CaCl_2$), 0.4% glucose) with 25 μg/mL chloramphenicol was used. In quorum sensing mediated toxin experiments, LB with 50 ng/mL anhydrotetracycline (atc), 1 mg/mL arabinose, and 25 μg/mL chloramphenicol was used. In three-member crossfeeding experiment, M9 was used as a base medium (lx M9 Salts, 2 mM $MgSO_4$, 100 μM $CaCl_2$)). In each condition, either 0.4% glucose or 0.2% lactose was added. 200 μM methionine was added where indicated.

Encapsulation into Droplets 1 mL syringes (BD Luer Lok) were fitted with 27 gauge needles and PE/2 tubing. 500 of mixed consortium was drawn into a 1 mL syringe. Hydrofluoroether oil was prepared with 2% surfactant (Holtze et al., 2008) and loaded into a 1 mL syringe. The syringes were inserted into the droplet-making polydimethylsiloxane (PDMS) device. Droplets were generated using 600 μL/hr oil and 300 μL/hr flow rates at a 30 μm×25 μm junction, producing ~40 μm diameter droplets at 4.8 kHz. Droplets were collected into a test tube for 15 minutes, then incubated for 18 hours at 37° C. to allow the cells to grow.

Microscopy and Image Processing

Droplets were pipetted into chamber microscopy slides (Invitrogen #C10228) and imaged with a 20× objective (Nikon, #MRH10201) on a Ti-E Eclipse inverted microscope (Nikon). Fluorescence was imaged using 455 nm, 495 nm, 515 nm, 585 nm wavelength filters (Chroma).

A computational pipeline in Python was developed to perform automated interaction network inference. Droplets were identified from the phase contrast image using the Hough transformation algorithm (OpenCV 3). Droplets that deviate more than 10% from 40 μm were not analyzed. Cells in each fluorescent channel were counted by identifying connected regions by scanning a range of intensity thresholds and binarizing the image. Interaction strength was calculated as $\log_2$(mean cell count with partner/mean cell count alone) (Foster and Bell, 2012). Networks were exported to Cytoscape 3.5 for visualization.

Development and Validation of Cell Counting Workflow in Droplets

Figure 8A:
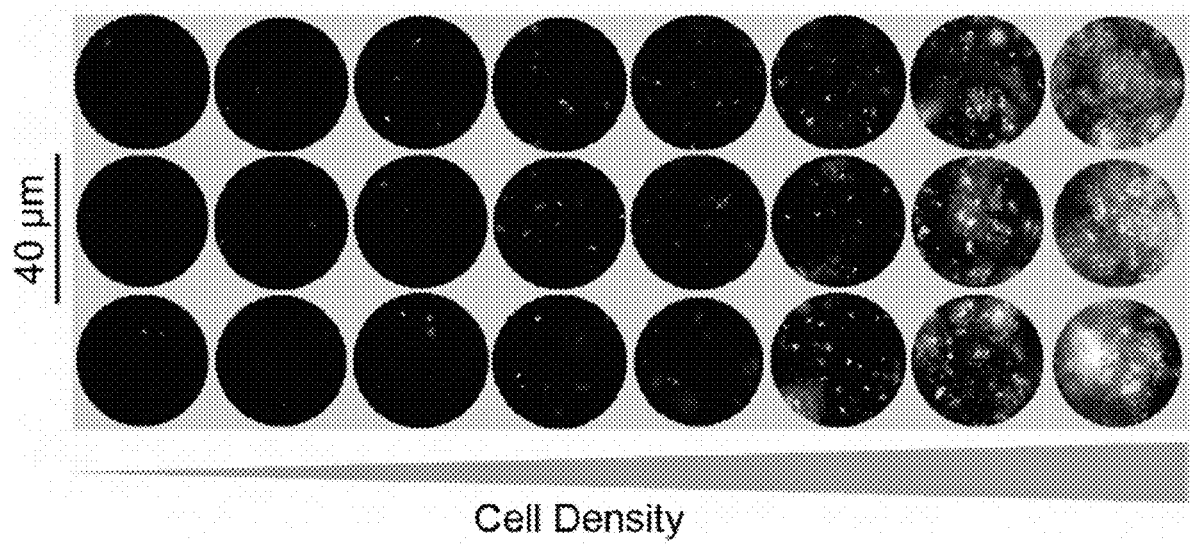
FIG. 8A. Representative fluorescent microscopy images of droplets containing three fluorescently labeled bacterial strains with YFP (strain ST Lac*), RFP (strain EC WT) or CFP (strain EC Met-). Each column represents a 2-fold dilution of the mixed culture prior to cell encapsulation in droplets.
Figure 8B:
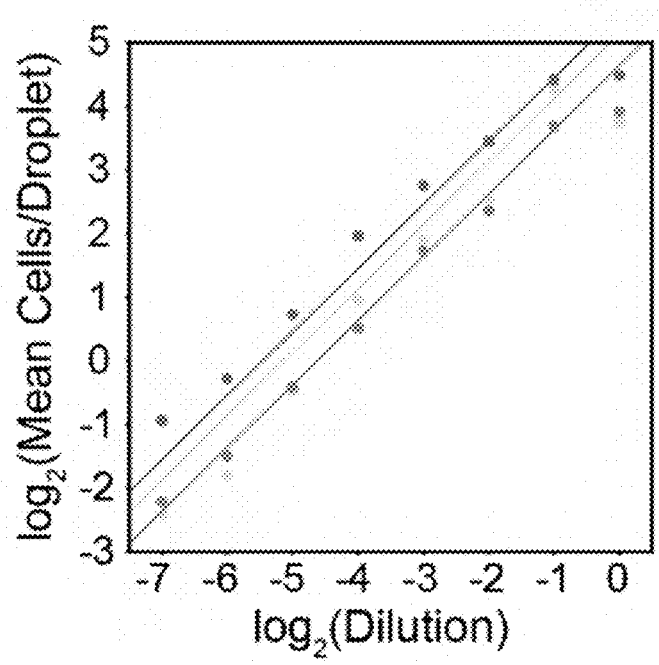
FIG. 8B. Scatter plot of dilution vs. the log 2 transform of the mean number of cells per drop in the experiment of FIG. 8A. Each data point represents the mean of between 400 and 600 droplets.

To elucidate how the presence of a partner (different bacterial strain) altered microbial growth, we needed to develop a method to accurately count fluorescently labeled cells within each droplet. To determine the cell count dynamic range, we applied this method to a mixture of three fluorescently labeled strains (CFP-labeled E. coli (strain EC Met-), RFP-labeled E. coli strain (strain EC WT) and YFP-labeled Salmonella (strain ST Lac*)) across a broad range of total cell densities (see above). The number of counted cells of each species decreased linearly with each dilution, except for the highest density droplets, suggesting that the linear range of this cell-counting method extends from 1 to ~40 cells per droplet (FIG. 8A). Fluorescent images of the highest density droplets showed cells that were difficult to count, even with the naked eye, so the diversion of this condition from the linear trend is not surprising (FIG. 8B).

Investigating Two-Member Consortia with Defined Positive or Negative Interactions We investigated whether we could infer defined microbial interactions in synthetic two-member consortia. A microbial interaction was inferred by computing the ratio of the average number of cells of a specific organism in the presence and absence of a distinct partner strain at a specific time point. To determine whether our method could illuminate known interactions, we constructed a synthetic consortium composed of bi-directional positive interactions (mutualism) or a uni-directional negative interaction (amensalism). We applied our method to reverse engineer the network based on the absolute abundance patterns of each strain across all droplets.

Figure 9A:
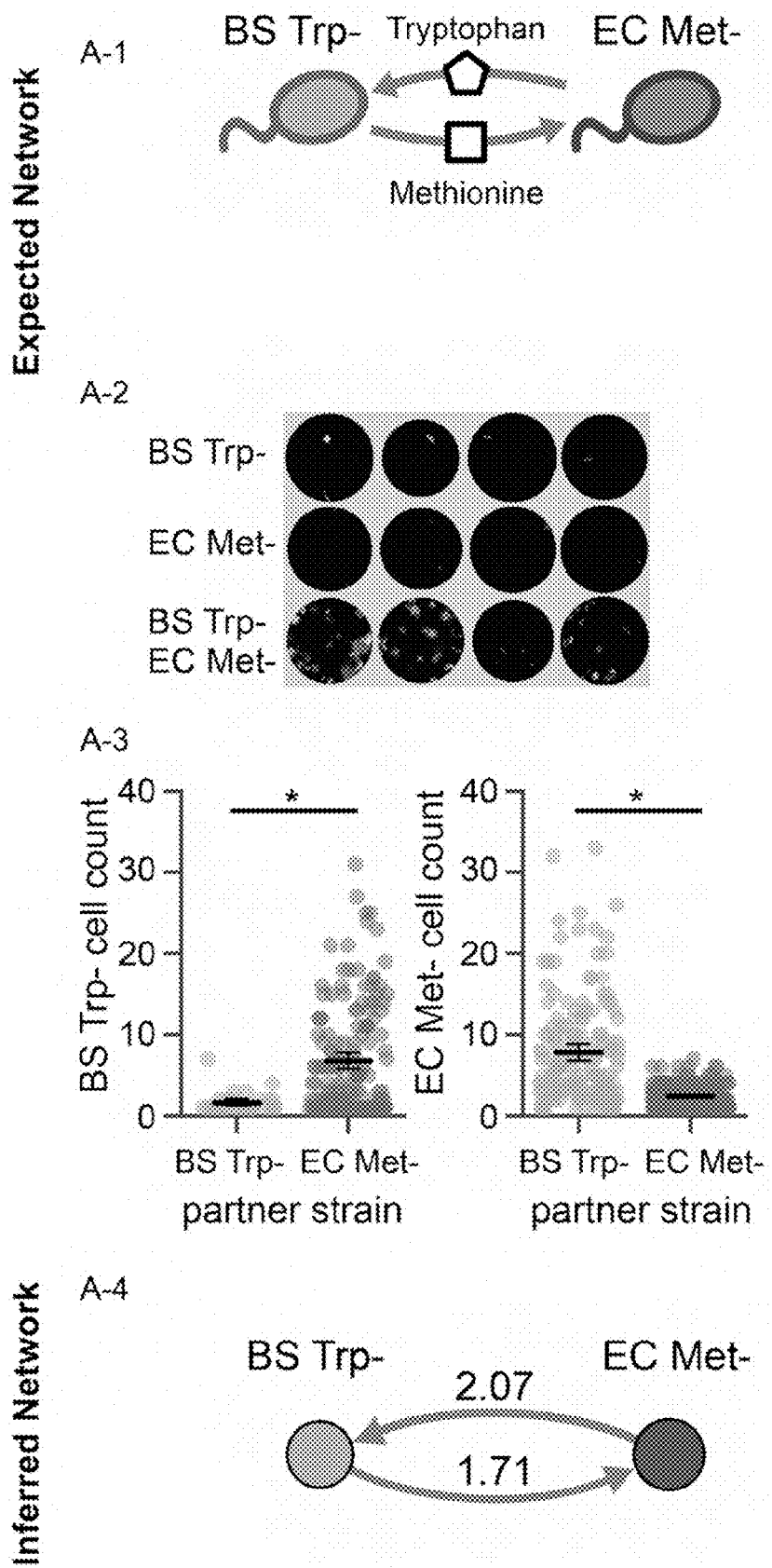
FIGS. 9A and 9B. Inferring microbial interactions in two-member mutualism (FIG. 9A) and amensalism (FIG. 9B). The mutualism community consisted of a GFP-labeled *B. subtilis* tryptophan auxotroph (BS Trp-, green) and RFP-labeled *E. coli* Methionine auxotroph (EC Met-, red) and designed to exhibit a mutualism (A-1). Representative fluorescence microscopy image of droplets containing single or a two-member community (A-2). The average growth of each strain was significantly increased in co-culture than alone (A-3, n=187 p<0.0001 left, n=372 p<0.0001 right). The inferred interaction network for the EC Met-, BS Trp- consortium matches the expected topology (A-4). The amensalism community consisted of a GFP-labeled sender strain that produces a quorum sensing signal to activate the expression of an endoribonuclease (MazF) in a RFP-labeled receiver strain (B-1). Representative fluorescence microscopy image of droplets containing single or a two-member community (B-2). Scatter plot of the number of sender cells in each drop in the absence and presence of the receiver strain (n=1572, B-3 left). The difference in the means are statistically significant (p<0.0001, B-3 left). The difference in the means are statistically significant (p<0.0001, B-3 right). Edge labels represent the interaction strength ($log_2$ transformed). Node size represents average cell count of each strain alone.

A synthetic amino acid cross-feeding mutualism was constructed composed of an RFP-labeled *E. coli* auxotrophic for Methionine (EC Met−) and GFP-labeled *B. subtilis* auxotrophic for Tryptophan (BS Trp−). The expected interaction between these two strains is an obligate mutualism, whereby neither strain grows alone in minimal media lacking amino acids but can grow in the presence of the partner strain. Visually from fluorescence microscopy, the expected obligate mutualism was observed (FIG. 9A, A-1). Quantifying cell abundance across all droplets revealed that the BS Trp− and EC Met− strains grew to 3.3× ($p<0.0001$) and 4.2× ($p<0.0001$) in the presence of the partner strain compared to alone (FIG. 9A, A-3). These data demonstrated that we could infer a bi-directional positive interaction network based on the absolute abundance of cells across droplets (FIG. 9A, A-4).

Figure 9B:
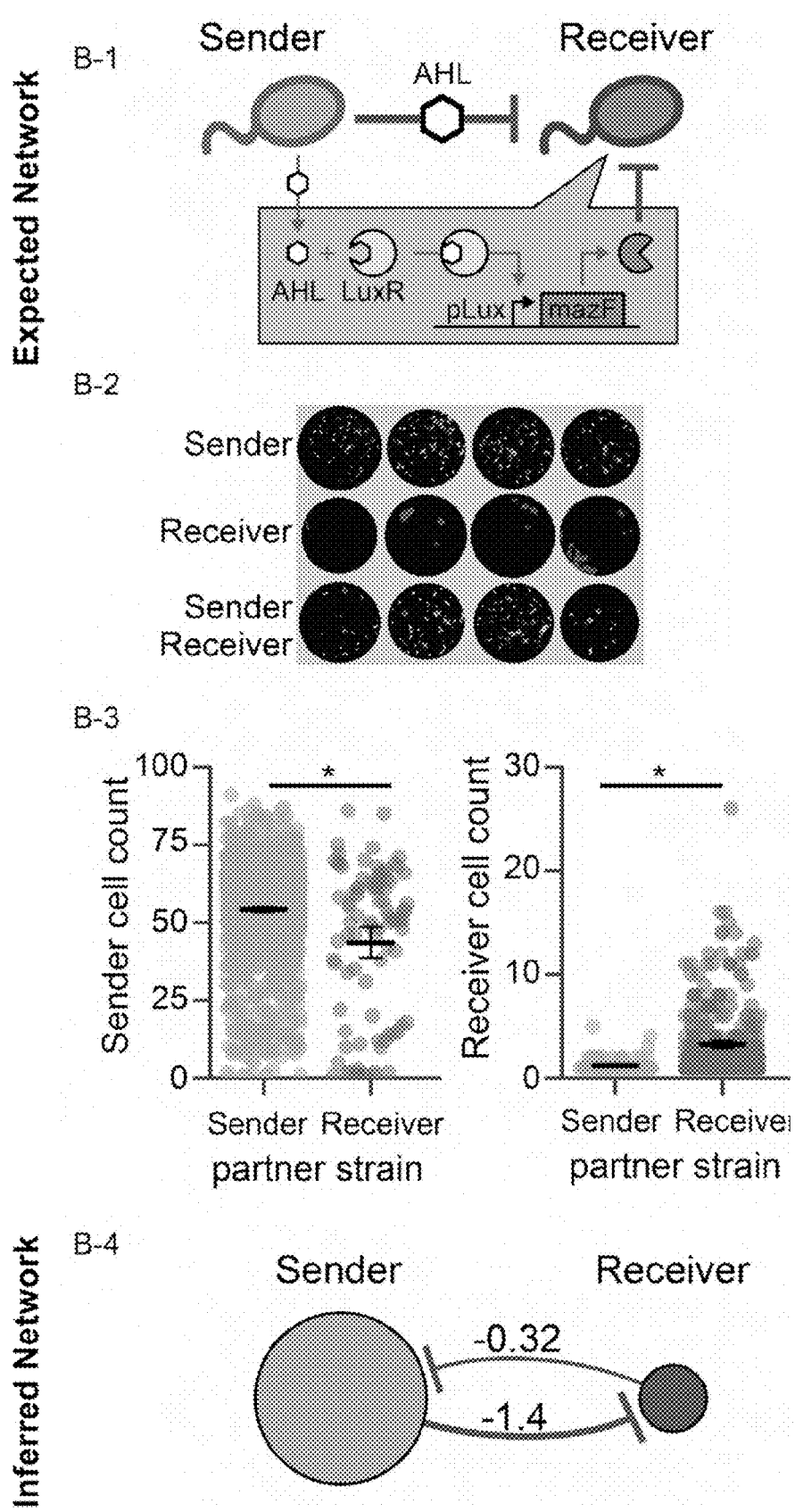
Figure 10A:
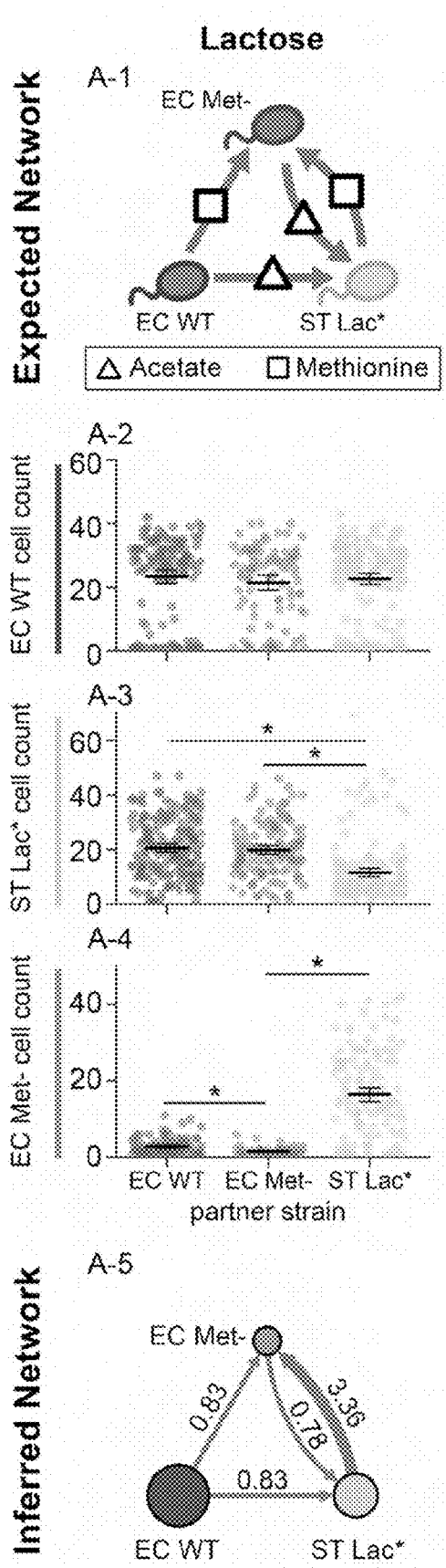
FIGS. 10A-10D. An engineered three-member consortium was grown in four variants of M9 media, Lactose (FIG. 10A), Lactose+Methionine (FIG. 10B), Glucose (FIG. 10C), and Glucose+Methionine (FIG. 10D). The expected interaction network topology changes depending on the media in which the community is grown (A1-D1). For the EC Met- strain, which requires methionine to grow, positive cross-feeding interactions are observed in media lacking methionine (p<0.0001, n=155 for EC WT to EC Met- in Lactose M9, p<0.0001, n=202 for ST Lac* to EC Met in Lactose M9, p<0.0001, n=95 for EC WT to EC Met- in Glucose M9, p<0.0001, n=78 for ST Lac* to EC Met- in Glucose M9). For the ST Lac* strain, which cannot metabolize lactose, positive interactions are seen in media containing lactose through acetate crossfeeding (p<0.0001, n=373 for EC WT to ST Lac* in Lactose, p<0.0001, n=317 for EC Met- to ST Lac* in Lactose, p<0.0001, n=333 for EC WT to ST Lac* in Lactose+Methionine, p<0.0001, n=300 for EC Met- to ST Lac* in Lactose+Methionine). Crossfeeding interactions can be switched on/off independently by the addition of the missing metabolite (A5-D-5). Edges represent interaction strengths ($log_2$ transformed). Node sizes represent average growth of each strain alone.
Figure 10B:
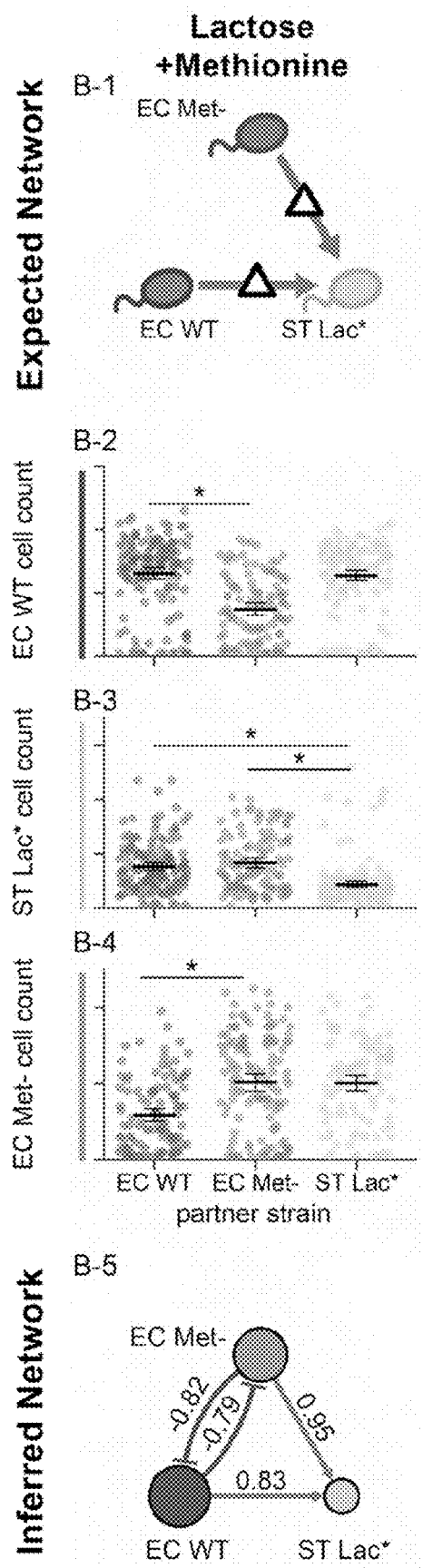
Figure 10C:
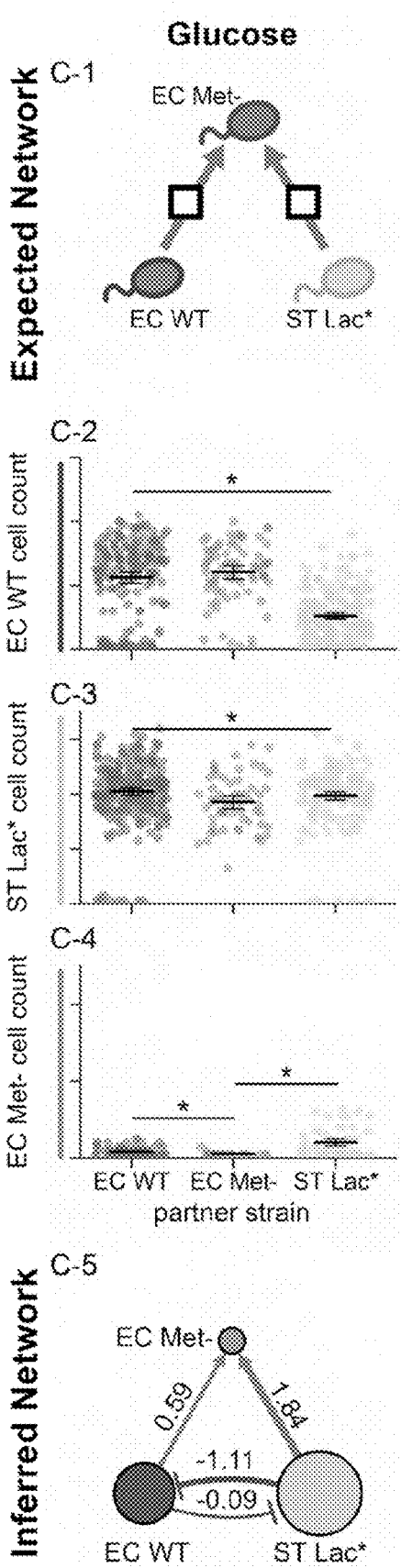
Figure 10D:
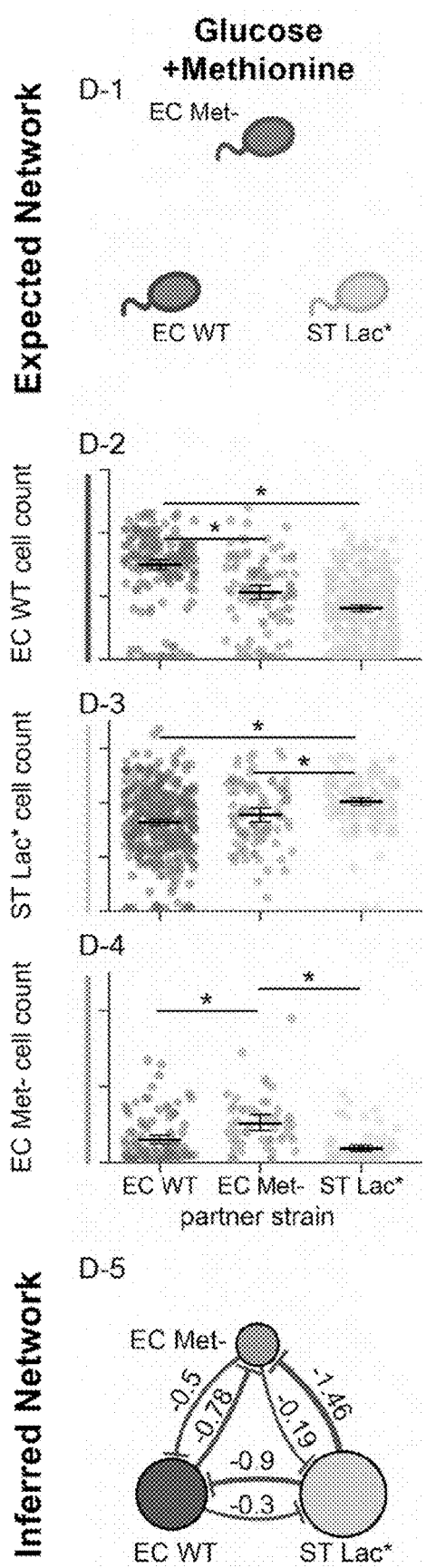

To determine if our method could deduce negative interactions, a synthetic community coupled by a uni-directional negative interaction was constructed. A GFP-labeled *E. coli* sender strain produced a quorum-sensing signal acyl-homoserine lactone that induced the expression of an endoribonuclease toxin (MazF) in the RFP-labeled *E. coli* partner strain (FIG. 9B, B-1). High expression of MazF inhibits cell growth by global mRNA decay (Venturelli et al., 2017). From imaging, we find visually that the receiver cells (red) do not divide if co-encapsulated with the sender cells (green) as expected (FIG. 9B, B-2). Computational cell counting revealed that the receiver strain was strongly inhibited by the sender, reaching a 0.38× average cell count with the sender compared to alone (FIG. 9B, B-3). We also identified that the sender strain was slightly inhibited to a 0.80× average cell count when grown with the receiver compared to alone (FIG. 9B, B-3). The inferred interaction network correctly identifies the engineered negative interaction (FIG. 9B, B-4, green to red) and an additional negative interaction (FIG. 9B, B-4, red to green).

Nutrient Availability Modulates the Interaction Network of a Three-Member Consortium The interaction network for a three-member consortium consisting of RFP-labeled *E. coli* MG1655 (EC WT), CFP-labeled *E. coli* auxotrophic for Methionine (EC Met−), and YFP-labeled S. *Typhimurium* unable to metabolize lactose (ST Lac*) was characterized in four variants of M9 medium (FIGS. 10A-10D, panels A-1, B-1, C-1, and D-1). This system was adapted from the work described in (Hammarlund et al., 2018). In each medium, either Lactose or Glucose was used as the primary carbon source and supplemented with Methionine when noted. In Lactose M9 medium, ST Lac* requires crossfeeding of acetate from the *E. coli* strains, which can metabolize lactose and secrete acetate as a byproduct. In medium lacking methionine, EC Met− requires crossfeeding of methionine from ST Lac* or EC WT. We were able to detect all engineered positive interactions as significantly improved growth of each strain when grown with a partner strain producing the cross-fed metabolite (FIGS. 10A-10D, panels A-2 through D-4). Additionally, if a strain is fit in media where it does not require cross-fed metabolites, it exhibits a negative interaction with other strains, likely through space and resource competition (FIGS. 10A-10D, panels A-5, B-5, C-5, and D-5, red edges). We find that we can independently turn off specific interactions by adding or removing the cross-fed metabolite.

Detecting Higher Order Interactions

Figure 11:
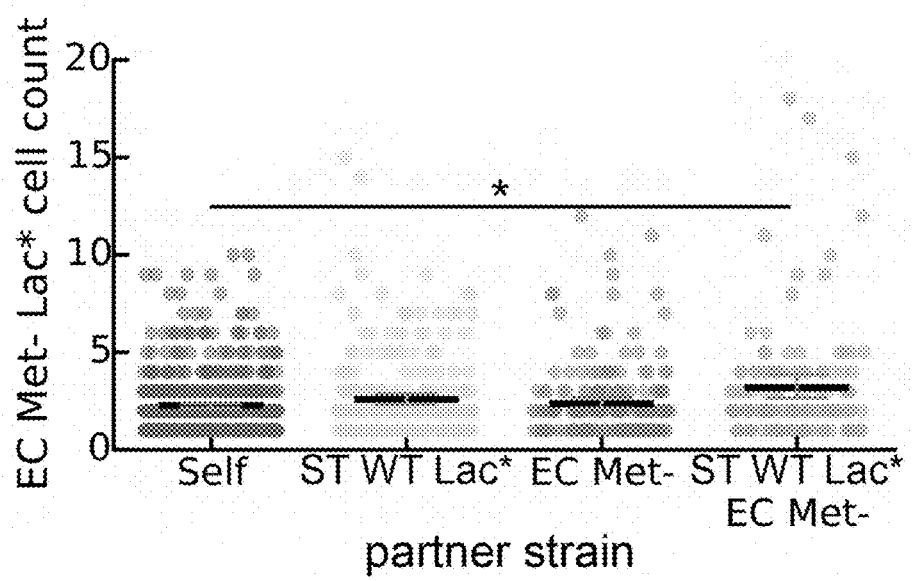
FIG. 11. An engineered three-member consortium was designed to contain a higher order interaction, where the EC Met- Lac* strain requires simultaneous crossfeeding from both an acetate producer (EC Met-) and methionine producer (ST Lac*). By analyzing the single-, two-, and three-member droplets, we can detect this higher order interaction (p<0.05, n=703, panel A). This allows us to infer the AND topology, where the EC Met- Lac* strain grows significantly only in the presence of both strains (panel B).
Figure 11:
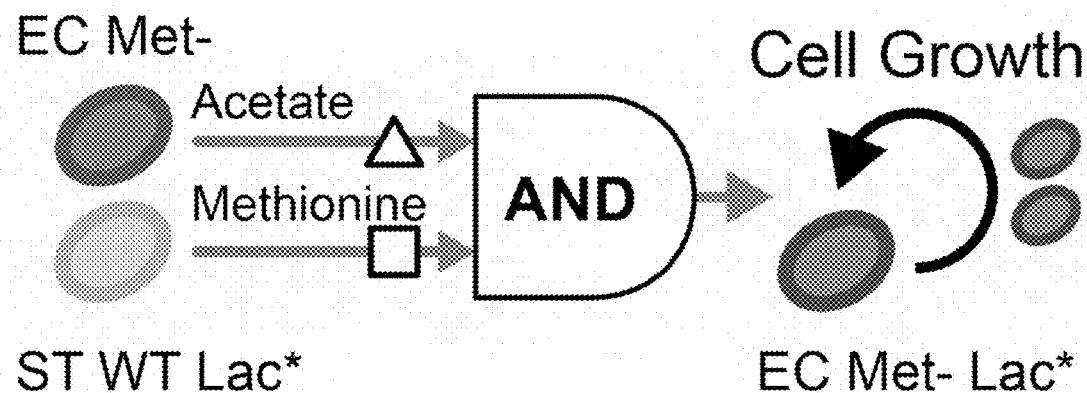

Higher order interactions are those where the interaction between two strains is modified by a third organism. To test whether the method can be used to detect higher order interactions, we used an *E. coli* strain that cannot synthesize methionine nor metabolize lactose (EC Met− Lac*) in M9 Lactose medium. In consortia, this strain cannot grow unless it is cross-fed acetate as the carbon source from EC Met− and cross-fed methionine from ST Lac*. Through Poisson loading, some droplets start with all three strains, which allow us to compare growth of each strain alone, in two-member consortia, and three-member consortia. As expected, we find that the mean growth of the double auxotroph EC Met− Lac* RFP is significantly increased only when grown in the three-member consortium ($p<0.05$). See FIG. 11.

Deciphering Microbial Interaction Networks by Randomly Encapsulating Cells in Droplets and Quantitating Cells Using Sequencing with Barcoded Beads Barcoded DNA Bead Design Bead-bound barcoded oligonucleotides are used as reverse transcription primers to sequence cells within droplets and map reads to back to individual droplets. The oligonucleotides included the following from 5'-to-3': (a) a poly-T tail as a spacer; (b) an Illumina adaptor sequence; (c) a Unique Bead Identifier (UBI), which is an 8 bp random sequence specific to each bead; (d) a Unique Molecule Identifier (UMI), which is an 8 bp random sequence specific to each oligonucleotide, and (e) a 16S rRNA annealing region, which captures a conserved region of the 16S rRNA. The beads were synthesized by ChemGenes Corporation (Wilmington, Mass.). The oligonucleotides had the following sequence:

(SEQ ID NO: 1)
5'-Bead-linker-TTTTTTTCCTACACGACGCTCTTCCGA
TCTJJJJJJJJJNNNNNNNNGGACTACHVGGGTWTCTAAT-3'

The TTTTTTT sequence (bases 1-7 of SEQ ID NO:1) is a spacer to distance priming regions from the bead. The CCTACACGACGCTCTTCCGATCT sequence (bases 8-30 of SEQ ID NO:1) is a priming region for PCR amplification after reverse transcription. The BMW sequence (bases 31-38 of SEQ ID NO:1) represents the UBI (wherein J can be any nucleotide), which is conserved across all oligos on a single bead. The sequence (bases 39-46 of SEQ ID NO:1) represents the UMI (wherein N can be any nucleotide), which is randomized across all the oligonucleotides on a single bead. The GGACTACHVGGGTWTCTAAT sequence (bases 47-66 of SEQ ID NO:1) is a 16S rRNA primer for hybridization to rRNA molecules and subsequent reverse transcription.

Preparation for Merging

*E. coli* MG1655 expressing RFP (EC) and *S. typhimurium* expressing YFP (ST) were grown overnight at 37° C. to stationary phase from glycerol stocks into LB medium containing 1M IPTG, Chloramphenicol (25 ug/mL) and Kanamycin (25 ug/mL) respectively. Prior to loading cells into 1 mL syringes, the OD600 reading of the strains were taken, and were usually at OD600 of 7 and 3.2 respectively. Hydrofluoroethylene (1% surfactant) was filtered with 20 um filter to remove dust prior to loading into a 1 mL syringe. Approximately 45 μm diameter droplets were generated using a droplet forming device as shown in FIG. 2 with flow rates of 600 μL/hr (oil) and 500 μL/hr (cells) at a 30 μm×25 μm junction. Droplets were collected into separate test tubes and mixed according to ratios indicated prior loading into a 1 mL syringe for merging. Fresh 1M NaCl, and Hydrofluoroethylene (1% surfactant) were prepared in 1 mL syringes and 5 mL syringes respectively. Approximately 50,000 barcoded DNA beads (ChemGenes Corporation, described previously) were washed with 10,000× volume molecular biology grade water to remove free barcoded bead oligos, and resuspended in 2 mL lysis buffer (Lucigen Corporation, Middleton, Wis.). The bead suspension was loaded into a 3 mL syringe containing a magnetic stir bar that keeps the beads resuspended when performing the merging experiment.

Merger Design

Figure 12:
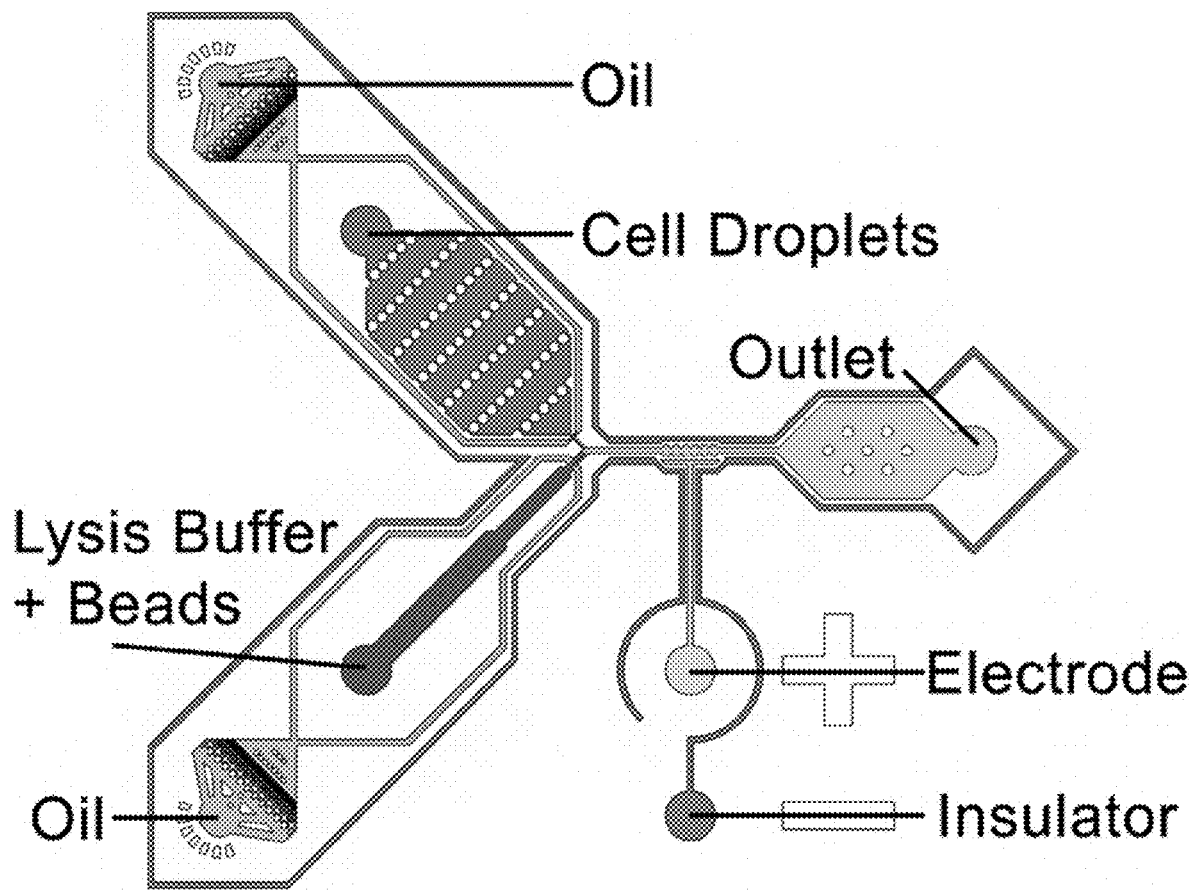
FIG. 12. A droplet merger microfluidic device for rRNA capture.

A droplet merger microfluidic device to merge droplets containing a microbial community (cell droplet, CD) with a droplet containing a barcoded bead (bead droplet, BD) is shown in FIG. 12. Characteristics include: (1) A narrow lysis buffer loading channel to maintain high flow velocity and prevent bead clogging; (2) A two-layer design to independently control droplet reinjection chamber and lysis buffer channels; (3) A modified 'moat' to produce electronic shielding from the electrode; and (4) A longer droplet co-flow channel to allow more time for cell-droplets to merge with lysis buffer droplets. Once microbial communities have formed in droplets (cell droplets), they are loaded into the device. Simultaneously, DNA-beads suspended in lysis buffer are emulsified and co-flowed with cell droplets. The cell droplets and bead droplets pair up, approximately 1:1, and flow into an electric field produced by the electrode, causing the two droplets to merge. The cells then lyse, allowing the rRNA to anneal to the DNA barcoded bead for downstream library preparation.

Merging

The 1M NaCl syringe tubes were first inserted into the merging microfluidic device as shown in FIG. 12 and were manually operated to fill the moat. Following that, the CD, oil for diluting CD, oil for BD formation, bead suspension and outlet tubes were inserted into the merging microfluidic device. The magnetic stirrer (VP Scientific Part #710D2) was also set to 30 to make sure the beads were evenly mixed for the merging experiment. For merging experiments, typical flow rates were:

1. Beads in lysis buffer—1000 µl/hr
2. Oil for beads—2000 µL/hr
3. Cell droplets—25 µL/hr
4. Oil for cell droplets—10 µL/hr After achieving optimal flow rate, where cell droplets to bead droplets are as close as 1:1, the voltage for the electrode connected to the 1M NaCl syringe (+) channel was set to ~2V to facilitate merging. Following visual confirmation via slow motion videos of droplets merging, the flow was allowed to continue for 5 minutes before collecting the merged droplets in a 50-mL conical tube. Merged droplets were collected for 30 minutes to 2 hours depending on the experiment.

Optimization of Merging Workflow

We have identified key parameters that are important for achieving a high merging efficiency between CD and BD. A key parameter is the oil flow rate which allows modulation of the size of the BD relative to the CD (approximately 5:1 difference in droplet diameter). Higher merging efficiency is achieved by tuning the flow rates such that the CDs are closer to the BDs in the merger device by reducing the oil flow rate of CDs. By making these two modifications, we have increased our merging efficiency to approximately 80% merging efficiency. Our current flow rates are: (1) Bead droplets—1000 µl/hr; (2) Oil for beads—2000 µL/hr, and (3) Cell droplets—25 µL/hr.

Following collection of merged droplets, we coalesced the collected droplets using an antistatic gun (Karbaschi et al., 2017), spun the beads (containing hybridized 16S rRNA), and diluted the samples to reduce the concentration of free RNA and bead oligos. Next, we performed a reverse transcriptase reaction to generate cDNA.

Reverse Transcription (RT)

Following collection of merged droplets, the 50-mL conical tube was left on ice for 10 minutes to ensure hybridization of 16S rRNA to barcoded DNA primers bound to beads. Oil at the bottom of the conical tube was removed and droplets were aliquoted to microfuge tubes. Typically, 1 mL of water would be added to 200 µL of droplets in a microfuge tube to dilute away free RNA and free bead oligos when coalescing with the static gun. Following coalescence, the beads were spun down with a table-top centrifuge at 1000 Xg, and the remaining oil was removed. Similarly, most of the water was removed until 15 µL remained containing the beads for reverse transcription (RT) reaction.

RT was carried out (iSelect cDNA synthesis kit) in a 42° C. water bath with rotation using a 3D-printed spinner. The magnetic stirrer was set at ~22 to ensure the beads were resuspended during the RT reaction. Following RT, the beads were spun down and washed once with 100 µL TE-SDS, and twice with 100 µL TE-TW. The beads were then treated with ExoI exonuclease enzyme (NEB) with rotation using the spinner at 37° C. Similarly, the beads were also spun and washed with 100 µL TE-SDS and twice with 100 µL TE-TW to prepare for PCR. PCR of the beads was then carried out using Kapa HiFi HotStart DNA polymerase (KapaBiosystems KK2601), with 1M Betaine at 68° C. annealing temperature.

Sequencing Library Preparation and Data Analysis

Two methods were used for sequencing libraries generated through the methods outlined above. The first was through standard Illumina MiSeq using primers oOSV377 (5'-AATGATACGGCGACCACCGAGATCTA-CACTGGCGCACACTCTTTCCCTACAC GACGCTCTTCCGATCT-3', SEQ ID NO:2) and oOSV381 (5'-CAAGCAGAAGACGGCATACGAGA-TACGACACTGTGACTGGAGTTCAGACGT GTGCTCTTCCGATCTCGTGCCAGCAGCCGCGGTAA-3', SEQ ID NO:3). In the oOSV377 primer, the AATGA-TACGGCGACCACCGAGATCTACAC sequence (bases 1-29 of SEQ ID NO:2) and the ACACTCTTTC sequence (bases 36-45 of SEQ ID NO:2) are Illumina adapter sequences, the TGGCGC sequence (bases 30-35 of SEQ ID NO:2) is an Illumina index for multiplexing of libraries, and the CCTACACGACGCTCTTCCGATCT sequence (bases 46-68 of SEQ ID NO:2) is a priming region for PCR amplification after reverse transcription (this is also part of the partial Illumina adapter sequence in the oligonucleotides). In the oOSV381 primer, the CAAGCAGAA-GACGGCATACGAGAT sequence (bases 1-24 of SEQ ID NO:3) and the GACTGGAGTTCA-GACGTGTGCTCTTCCGATCT sequence (bases 35-66 of SEQ ID NO:3) are Illumina adapter sequences, the ACGACACTGT sequence (bases 25-35 of SEQ ID NO:3) is an Illumina index for multiplexing of libraries, and the CGTGCCAGCAGCCGCGGTAA sequence (bases 67-86 of SEQ ID NO:3) is a priming region for PCR amplification after reverse transcription. Samples sequenced via this method are referred to in the following examples with a [UW] after the sample name.

The second method, is called "Amplicon-EZ" and is provided by GeneWiz, Inc. (South Plainfield, N.J.). For this method, primers (oOSV570 and oOSV571) with partial Illumina adapters were used in the final PCR step of the protocol in generate a library. The library was then sent to GeneWiz, Inc. to amplify it further through PCR with primers containing indices as well as other parts of the Illumina adapters. The samples are then combined with samples from other customers and sequenced on Illumina MiSeq. The sequence of the oOSV570 primer is 5'-ACACTCTTTCCCTACACGACGCTCTTCCGATCT-3' (SEQ ID NO:4), wherein the ACACTCTTTC sequence (bases 1-10 of SEQ ID NO:4) constitutes the partial Illumina adapter and the CCTACACGACGCTCTTCCGATCT sequence (bases 11-33 of SEQ ID NO:4) constitutes a priming region for PCR amplification after reverse transcription (this is also part of the partial Illumina adapter sequence in the oligonucleotides). The sequence of the oOSV571 primer is 5'-GACTGGAGTTCAGACGTGTGCTCTTCC-GATCTCGTGCCAGCAGCCGCGGTAA-3' (SEQ ID NO:5), wherein the GACTGGAGTTCA-GACGTGTGCTCTTCCGATCT sequence (bases 1-32 of SEQ ID NO:5) constitutes the partial Illumina adapter and the CGTGCCAGCAGCCGCGGTAA sequence (bases 33-52 of SEQ ID NO:5) constitutes a priming region for PCR amplification after reverse transcription. Samples sequenced via this method will be referred to with a [EZ] after the sample name.

To analyze the next-generation sequencing data from our sequenced libraries, we extract the DNA barcodes, group similar barcodes that could be generated from PCR or sequencing errors, and assign a taxonomy to the associated 16S sequences. We can then calculate the ratio of unique 16S molecules of each species that were reverse transcribed from each bead by determining the number of unique molecule identifiers (UMIs) with 16S sequences assigned to the corresponding species.

An Exemplary Analysis Method is as Follows:
1. Merge forward and reverse reads using Pear (www.exelixis-lab.org/pear).
2. Create a whitelist of "true" UBI barcodes using the UMI-tools (Smith et al., 2017) whitelist function. By examining the associated distribution plots, choose a cutoff for the minimum number of barcodes to qualify as a "true" UBI barcode. The whitelist generated in this process also includes low read number barcodes that are one edit distance away from any "true" UBI barcode, which are assumed to be errors from PCR amplification or sequencing.
3. Extract the UBI and UMI sequences using the UMI-tools extract function. This corrects the erroneous barcodes identified in the previous step and screens out all reads that do not have a "true" UBI barcode.
4. Annotate the reads with their 16S taxonomy by comparing to a database of expected species 16S sequences using the usearch annot function (https://www.drive5.com/usearch/). This generates a text file that contains the species identification and percent identity for each read.
5. Filter out reads with less than 99% species identity.
6. Filter out UBI-UMI pairs for which the species specificity is not 100%. These products are not representative of the capture of a single 16S rRNA molecule and are therefore filtered out as noise. This typically occurs in 0.3-3% of the UBI-UMIs for experiments in which both EC and ST are present.
7. Determine the number of UMIs of each species associated with each UBI to determine the distribution of 16S sequences captured and reverse transcribed from each bead. Only UBIs with at least 10 different UMIs were included for further analysis to eliminate bias towards higher specificity from UBIs with low number of UMIs (i.e. for two UMIs, a mixed species UBI would falsely appear as 100% specific 67% of the time).

Amplification Optimization

Figure 13:
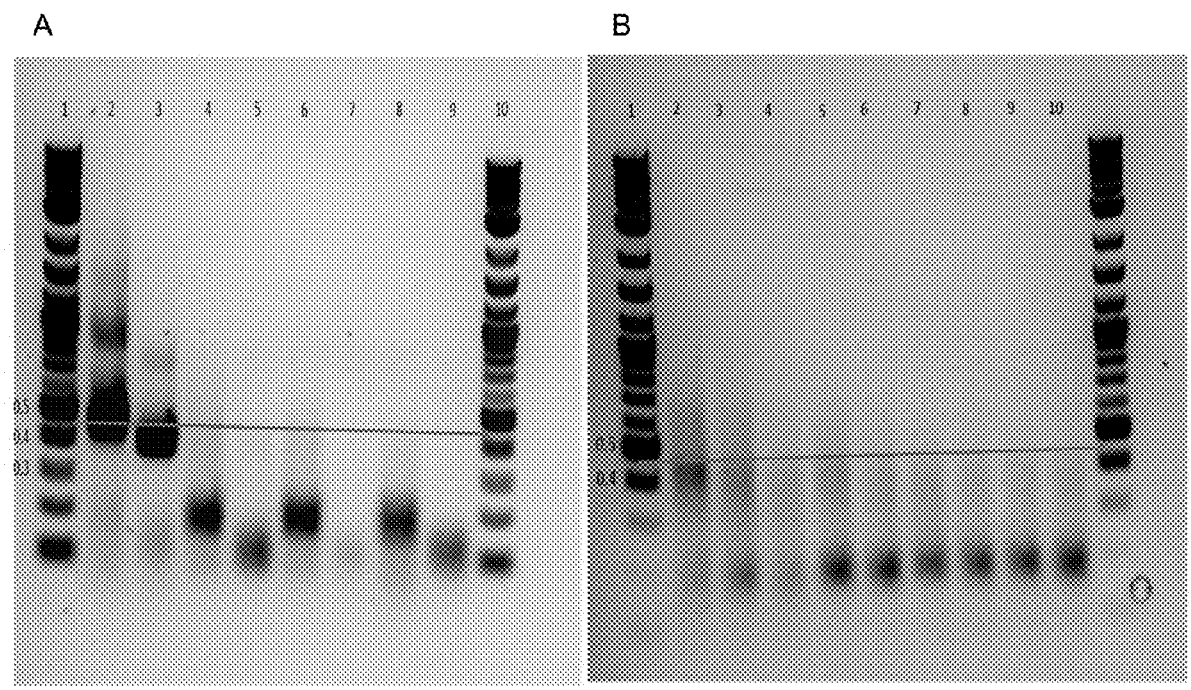
FIG. 13. Optimization of amplification using 1M betaine and higher annealing temperatures (68° C.). A) 1.5% agarose gel of PCR amplified products from cDNA generated by merging separately co-encapsulated E. coli and S. typhimurium droplets at 2:1 ratios, with different dilutions. [1,10: 2-log base pair ladder, 2: RT positive control. Primers with full Illumina adapters for sequencing by [UW] were used for PCR amplification of cDNA generated from reverse transcription of purified EC RNA using free oligo mimics of the bead oligos, 3: RT positive control. Same as 2, but PCR primers had partial Illumina adapters used for sequencing by [EZ], 4: [UW] primers used for PCR of cDNA generated from 200 uL of merged droplets, with 1 mL dilution in water, 5: Same as 4, but PCR with primers for [EZ], 6: [UW] primers used for PCR of cDNA generated from 800 µL of merged droplets, with 4 mL dilution in water, 7: Same as 6, but PCR with primers for [EZ], 8: [UW] primers used for PCR of cDNA generated from 800 µL of merged droplets, with 40 mL dilution in water, 9: Same as 8, but PCR with primers for [EZ]] (B) 1.5% agarose gel of PCR amplified products from same cDNA in (A) using [UW] primers and 1M betaine in each reaction, at different annealing temperatures. [1: 2-log base pair ladder, 2: 68° C. annealing temperature, cDNA from A-4, 3: 63° C. annealing temperature, cDNA from A-4, 4: 60° C. annealing temperature, cDNA from A-4, 5: 68° C. annealing temperature, cDNA from A-6, 6: 63° C. annealing temperature, cDNA from A-6, 7: 60° C. annealing temperature, cDNA from A-6, 8: 68° C. annealing temperature, cDNA from A-8, 9: 63° C. annealing temperature, cDNA from A-6, 10: 60° C. annealing temperature, cDNA from A-6]
Figure 14:
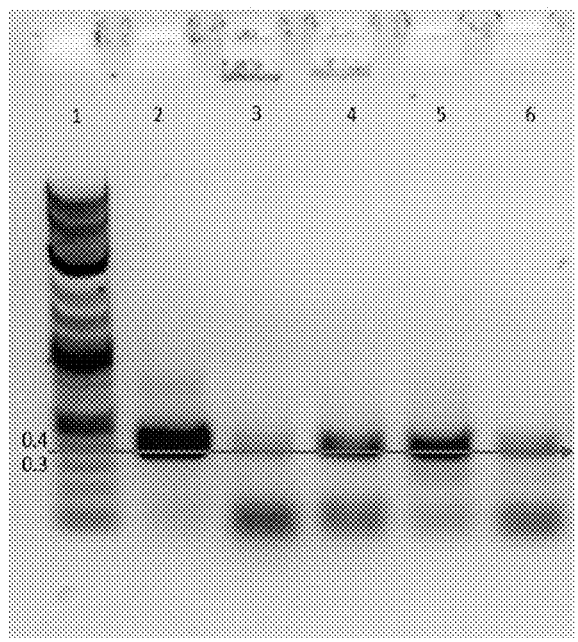
FIG. 14. 1.5% agarose gel of PCR amplified products from cDNA generated by purified RNA annealed with washed beads, with and without ExoI treatment with different bead concentrations. [1: 2-log base pair ladder, 2: RT positive control. Primers with full Illumina adapters for sequencing by [EZ] were used for PCR amplification of cDNA generated from reverse transcription of purified EC RNA using free oligo mimics of the bead oligos, 3: PCR amplification with [EZ] primers from cDNA generated from RT after incubation of 5000 beads with purified EC RNA, 4: Same as 3, but with the addition of ExoI treatment after RT, 5: Same as 4, but with 500 beads 6: Same as 4, but with 50 beads]

A step we had to troubleshoot was generating high yields (500 ng) of our amplicon for next-generation sequencing. We significantly improved the amplification of the correct product using 1M betaine and higher annealing temperature (68° C.) in the PCR amplification. Combining these two modifications reduced the yield of primer dimers and the correct amplicon (FIG. 13). Similarly, ExoI also significantly increased the correct amplicon (FIG. 14). See below for further information.

Cross-Talk Optimization

Figure 15A:
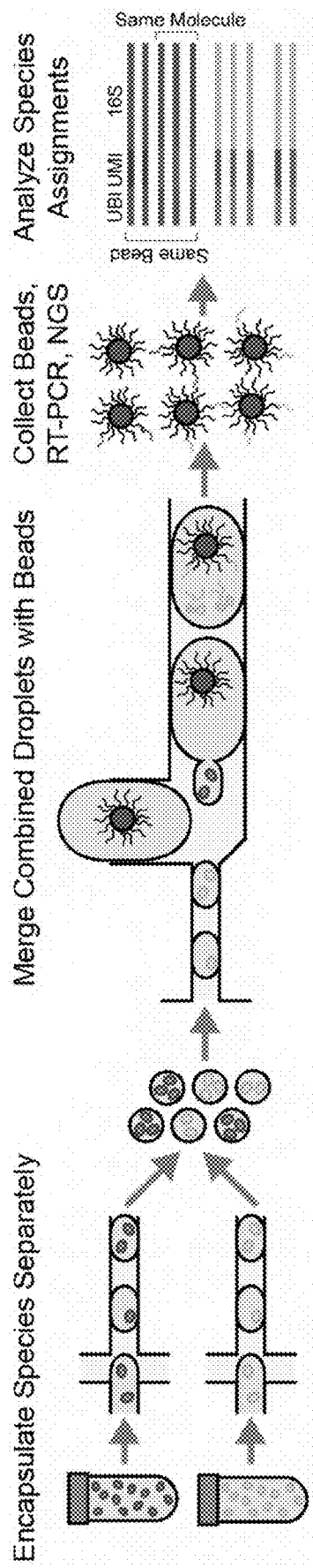
FIGS. 15A-E. Control experiments for merging.
Figure 15B:
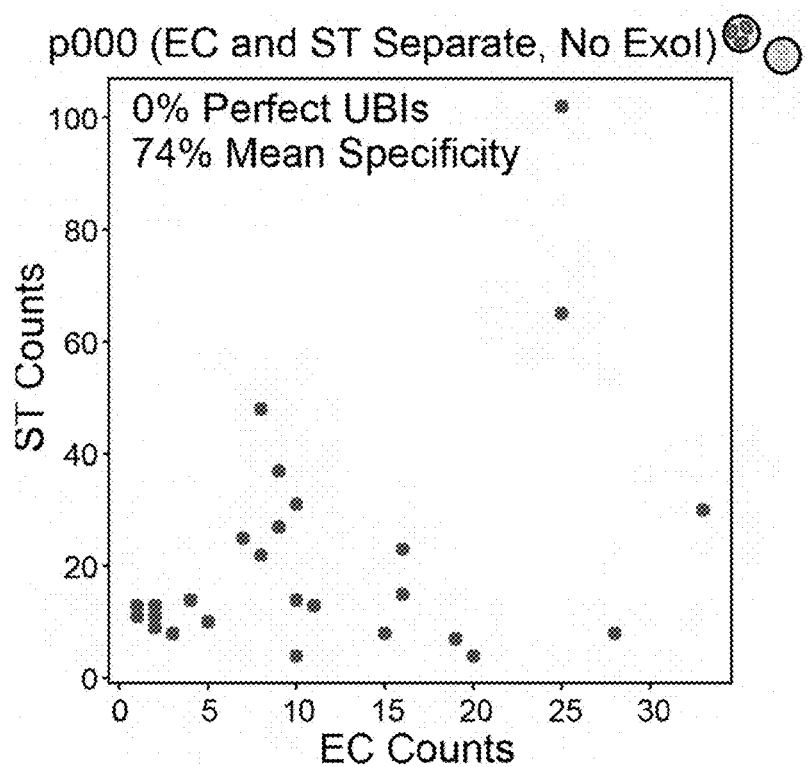

We conducted experiments to verify there is no cross-talk between beads. We devised a control wherein E. coli (EC) and Salmonella typhimurium (ST) were encapsulated in droplets and then combined before merging with RNA capture beads in lysis buffer (FIG. 15A). The beads were then collected, RT-PCR was performed, and the resulting products were sequenced using the [EZ] method (described in methods) and analyzed for their species specificity (i.e. whether E. coli 16S reads were found associated with beads that were primarily Salmonella or vice versa). FIG. 15B shows the number of counts of ST or EC for each UBI with a total number of counts greater than 10. 0% of these UBIs were perfectly specific for EC or ST and the mean specificity was only 74%. We hypothesized that the low species specificity of this data is due to the ability of oligonucleotides not used in RT to act as primers in subsequent PCR steps, wherein oligonucleotides from beads associated with one species could amplify cDNA of the other species.

Figure 15C:
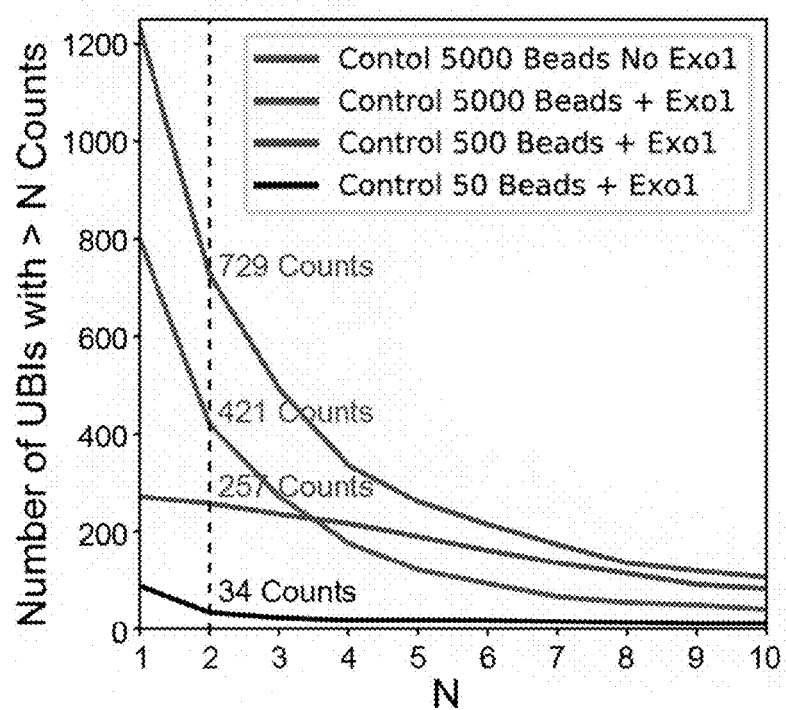

To address this issue, we modified the method to include treatment with exonuclease (ExoI) after RT and before PCR to degrade oligonucleotides not associated with an RNA template. To test the efficacy of this method, we performed RT-PCR with ExoI treatment on aliquots of 5000, 500, and 50 beads combined with purified E. coli RNA template and compared with a control of a 5000 bead sample without ExoI treatment. All conditions yielded DNA of the expected size (FIG. 14), so we performed sequencing on each sample with the [EZ] method (described above). FIG. 15C shows the number of UBIs versus increasing minimum number of counts. Several conclusions can be drawn from this result. First, treatment with ExoI allows more UBIs to rise above the background noise as can be seen by comparing the +/−ExoI samples, where the +ExoI sample had more UBIs above the minimum cutoff. Second, we saw a decreasing number of UBIs above the minimum counts cutoff with decreasing number of beads. However, the sample with the highest number of beads had exponentially increasing number of UBIs as the minimum cutoff was decreased, suggesting the read coverage was not sufficient to give a representative sample of the RT-PCR products from 5000 beads. In contrast, the lower bead count profiles were flatter and closer to the expected bead numbers.

Figure 15D:
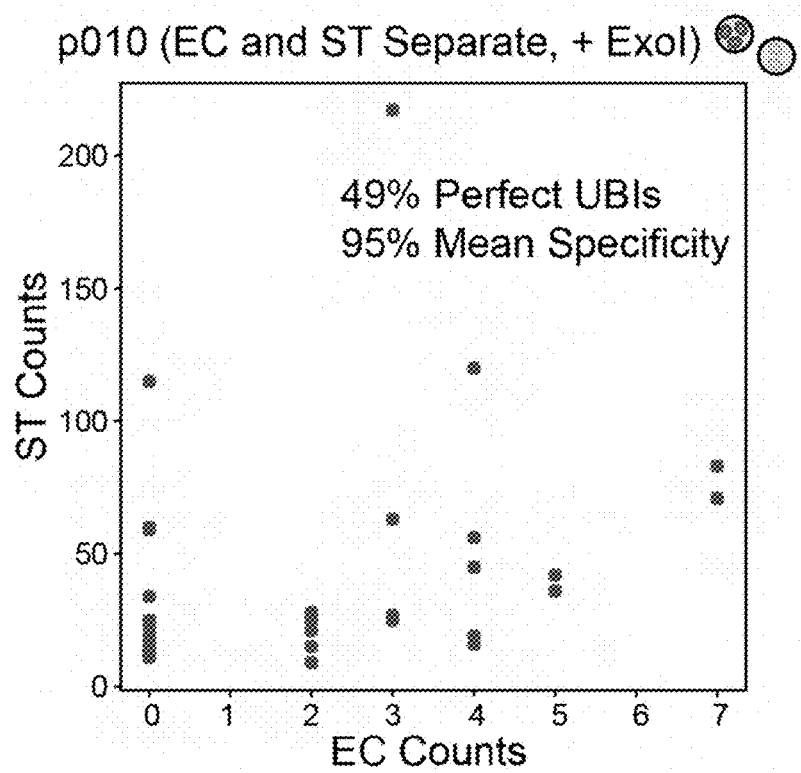
Figure 15E:
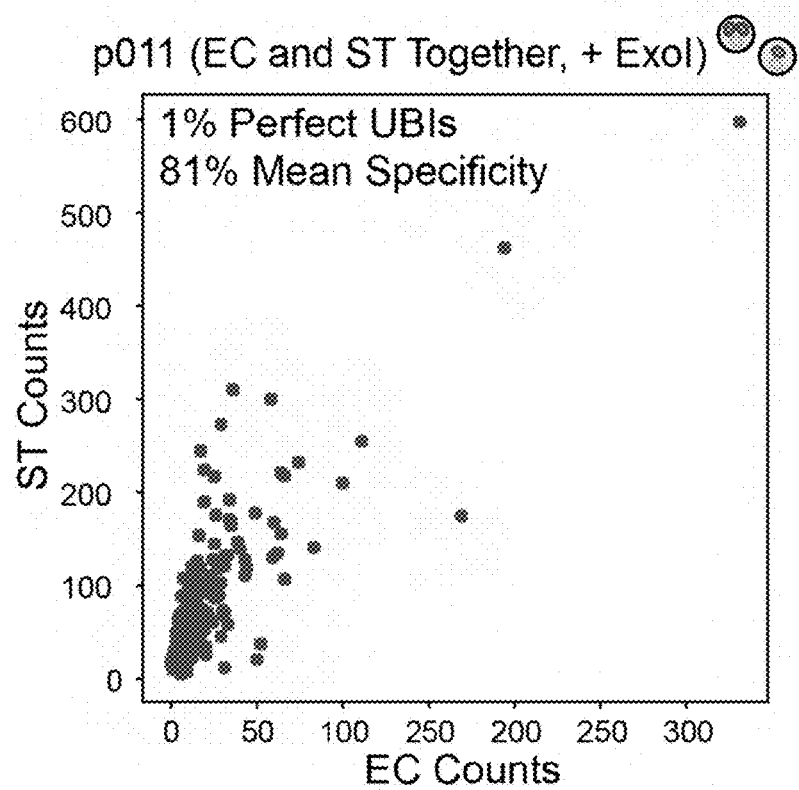

We repeated the merging experiment described for FIGS. 15A-C to determine whether ExoI treatment would decrease cross-talk between beads. FIG. 15D shows that the addition of ExoI treatment improved specificity such that 49% of beads were 100% specific for one species with a mean specificity of 95%. As a negative control for specificity, we performed a merging experiment with droplets containing a mixed population of EC and ST. FIG. 15E shows that this negative control had only 1% of UBIs with 100% specificity and a mean specificity of 81%. These results suggest that ExoI treatment greatly decreases cross-talk between beads.

The method can be improved with the use of perfluorooctanol for coalescing droplets, which should work more quickly and thus reduce the period during which RNA from one droplet could hybridize to a bead from a different droplet before being diluted into the bulk of the wash buffer (Macosko et al., 2015). Lower cell densities is also expected to reduce cross-talk.

Application of Methods to Gut Microbiota

Background

The human gastrointestinal tract is inhabited by a multitude of bacteria, fungi and viruses that collectively influence human health and performance. This human-associated microbial ecosystem impacts physiological functions via protection against invasion by intestinal pathogens, mediating energy balance and extracting nutrients from food, training the immune system and modulating neurological activities. The gut microbiota performs a myriad of chemical transformations to modulate human physiology including transformation of complex dietary substrates into short-chain fatty acids, synthesis of vitamins, modification of bile acids and xenobiotics and regulation of the immune system and host metabolism. Unraveling the emergent properties of this complex system requires a quantitative understanding of the mapping between network activities and population dynamics in response to environmental inputs.

In the last decade, it has become increasingly evident that alterations in the gut microbiota are associated with many diseases such as inflammatory bowel diseases, obesity, and type 2 diabetes. Short-chain fatty acids (SCFA—mainly acetate, propionate, and butyrate) have been suggested to play a major role in the dietary fiber—induced beneficial effects on obesity and insulin resistance. There are large interpersonal differences in the composition of the gut microbiota and the amount of SCFAs produced in response to different types of dietary fiber. Recent work showed that SCFAs regulate global histone acetylation and methylation, and gene expression in multiple host tissues. However, we are unable to predict how differences in the gut microbiota composition yield specific SCFAs profiles in response to dietary intervention.

Among the SCFAs, butyrate has received particular attention for its multiple beneficial effects, not only on the intestinal tract but the peripheral tissues as well. Butyrate has an important role as the preferred energy source for the colonic epithelium. In addition to its role as a fuel, butyrate affects gene expression, mainly through its action as a non-competitive inhibitor of histone deacetylases, leading to hyperacetylation of chromatin. Butyrate also has anti-inflammatory properties by inhibiting the activation of the transcription factor NF-κB and subsequent production of proinflammatory cytokines. Further, microbial species that synthesize butyrate were depleted in response to *Salmonella* invasion, illustrating that butyrate activity may enhance colonization resistance to intestinal pathogens. In humans, butyrate is synthesized by anaerobic gram-positive bacteria (butyrate-producing bacteria) distributed across several Clostridia clusters. The abundance of butyrate producers in the gut microbiota and butyrate activity varies significantly across individuals. The molecular, ecological and environmental factors that contribute to this variation remain unresolved.

Figure 16:
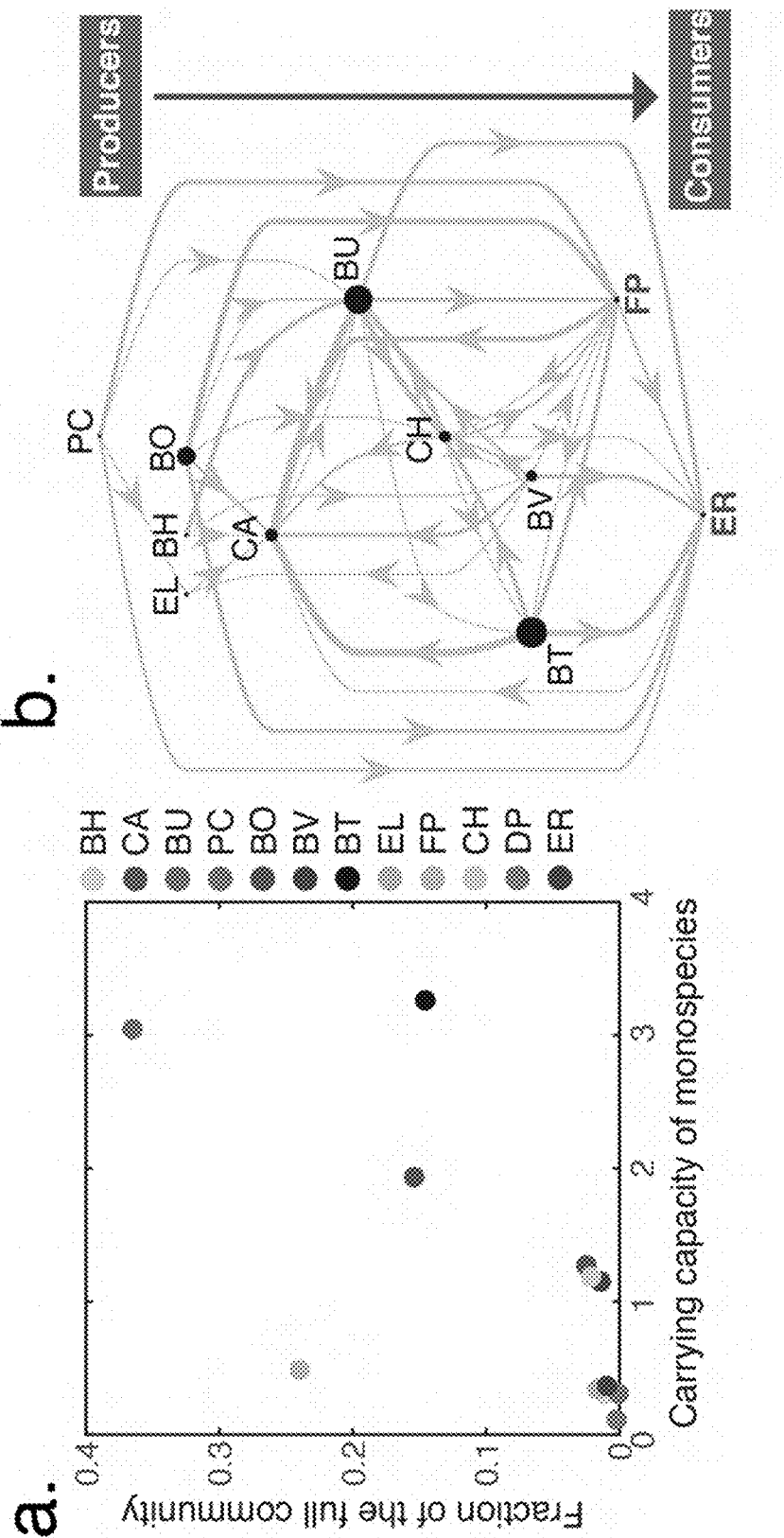
FIG. 16. Figures showing ecological interactions as major variables that influence prominent butyrate producers F. prausnitzii (FP) and E. rectale (ER) in human gut microbiome synthetic ecologies. Panel (a): Scatter plot of the carrying capacity of the monospecies vs. the fraction of the full (12-member) community at steady-state (t=71.4 hr). Panel (b): Exo-metabolomics network highlighting potential metabolic interchange between human gut microbiome species. The size of the node denotes the carrying capacity of the monospecies and the line width represents the number of secreted metabolites.

The multitude of bacteria that inhabit the mammalian intestine operate as an efficient bioreactor to transform complex dietary polysaccharides into fermentation end products using a division-of-labor strategy. For example, *Bacteroides* are equipped with the molecular machinery to degrade complex polysaccharides into substrates utilized by butyrate producers, highlighting metabolic complementarity between species. Mirroring these studies, data showed that ecological interactions significantly influenced the abundance of *F. prausnitzii* (FP) in synthetic ecologies (FIG. 16, panel A). Exo-metabolomic profiling data showed that FP and another prevalent butyrate-producing species *E. rectale* (ER) functioned as "consumers" in the network, suggesting that butyrate producers can exploit secreted metabolites synthesized by members of the gut microbiota for energy (FIG. 16, panel B). In sum, these findings indicate that ecological interactions are major variables that impact butyrate activity. In addition to metabolite interchange, signaling and warfare among microbial populations may shape community dynamics. Deciphering the molecular mechanisms that realize inter-species interactions is an area that remains largely unexplored in the gut microbiome and can provide novel approaches to manipulate the gut microbiota.

The gut microbiota contains hundreds of species spanning the Bacteroidetes, Firmicutes, Actinobacteria, Proteobacteria and Verrucomicrobia phyla. Due to the challenge of unraveling complex microbial interactions using limited resolution measurements, previous work has investigated simplified microbiome assemblages composed of 10-15 members (Faith et al., 2014; Faith et al., 2011). These simplified assemblages may not reproduce key features of the natural system including the breadth of microbial traits, density of ecological interactions, and mechanisms to promote stability and robustness to external perturbations. Using plate-based methods, it is not feasible to enumerate all possible pairwise assemblages. The experimental and computational methods provided herein can be employed to investigate microbiome communities that rival the complexity of the natural system.

While the identities of the organisms in the gut microbiota have been determined, the functional repertoire realized by each species is unknown. The functional capabilities of microbial species are highly intertwined with constituent members of the community and influenced by a myriad of abiotic and biotic factors. We lack an understanding of the organizational principles by which these intracellular networks, partitioned among species, are integrated into the total functional capabilities of the human gut microbiome, as well as how these activities are modulated by environmental context. The fundamental task resides in understanding biomolecular networks that span multiple species and deciphering mechanisms of stability and resilience in microbial ecosystems in response to environmental perturbations.

The gut microbiome is a dynamic and interdependent network shaped by resource competition and interchange, biomolecular warfare and signaling. A core challenge is that interactions in ecological networks do not follow a linear sequence but instead consist of numerous feedback loops, higher-order dependencies, coupling strengths and quantitative relationships that span multiple time and spatial scales. As a consequence, disturbances can propagate through the network in unexpected ways leading to shifts in the operating point of the system. To understand how community behaviors are realized by microbial interactions and environmental factors, it is important to go beyond static interaction networks and employ computational models that can analyze microbial community dynamics.

Computational models can be used to represent the complex interactions in microbial communities at different resolutions. The generalized Lotka-Volterra (gLV) model can realize a diverse repertoire of dynamical behaviors and the structure, and parameters of this model can be inferred from properly collected time-resolved data. In addition to illuminating network topology, "keystone" species, and strong interactions, this modeling framework can be used to analyze system stability, dynamical behaviors such as temporal order of community assembly, invasion by non-resident species and multistability. Further, concepts from control and dynamical systems can be used to analyze the robustness and controllability of the network to environmental inputs. Finally, the gLV model could be used to constrain mechanistic models that represent the bipartite structure of microbial interactions whereby metabolites produced or removed by specific species influence microbial fitness.

Apply Method to Reverse Engineer Interactions in a Complex Human Gut Microbiome Synthetic Ecology Since the gut microbiome is an anaerobic environment, the majority of bacteria that colonize the gastrointestinal tract are unable to grow in the presence of oxygen. Therefore, to study the ecological interactions in the gut microbiome, we a droplet-microfluidics station in an anaerobic chamber. As presented in the examples above, we mapped inter-species interactions between 12-member diverse human gut microbiome species using a data-derived modeling approach. Since we have extensively characterized the inter-species interactions in this synthetic ecology, we can use this system as a basis for our workflows in an anaerobic chamber. We can then interrogate inter-species interactions among members of a gut microbiome synthetic ecology that mirrors the complexity of the natural system (93 diverse species). Human gut microbiome type strains from ATCC and DSMZ can be selected based on the following criteria: (1) maximization of genetic diversity, (2) sequenced genomes, and (3) prevalent membership across microbiome samples (Qin et al., 2010). To elucidate how environmental conditions impact the ecological network, the community can be exposed to three nutrient conditions represent distinct dietary inputs: amylopectin, arabinogalactan, and porcine mucins.

In addition to environmental parameters, we can vary the average number of species encapsulated in each drop by controlling the initial cell density to interrogate higher-order interactions. A higher-order or conditional interaction is characterized by a change in pairwise interactions in the presence of a third species (Bairey et al., 2016). Higher-order interactions can be detected by analyzing the differences in network structure across different initial cell densities (Poisson distribution mean $\lambda=1-3$ cells per drop). Higher-order interactions can manifest as the appearance, disappearance or change in the nature of a pairwise interaction. Further, heterogeneity and low initial cell density across drops can allow us to probe the contribution of stochastic processes and density-dependent interactions to final community assembly. The contribution of stochastic processes to community assembly can be quantified using the absolute and relative abundance information. For example, the influence of stochastic processes would manifest as significant variability in steady-state community composition across drops.

Using a Model-Guided Approach to Dissect Community Dynamics, SCFA Activity, and Microbial Phenotypes Based on our procedure of reverse engineering the ecological network of a 12-member community, we can evaluate the robustness of the model to changes in environmental context and community complexity. We predict pairwise interactions can accurately represent the myriad of microbial interactions in microbiomes and how environmental factors impact microbial interaction rules.

To describe ecological dynamics across diverse operating regimes, we can employ models that link environmental parameters to population fitness. The time-resolved community structure of selected sub-communities can be measured in response to amylopectin, arabinogalactan, and porcine mucins. Leveraging the generalizable framework provided herein, we can infer the interactions between all members of the selected sub-communities to predict and analyze community behaviors. In addition to representing growth and inter-species interactions, the model can include a time-dependent environmental input that relates microbial fitness to nutrient concentrations. Our models can be validated using time-resolved measurements of the full community and leave-one-outs in response to alternating nutrient shifts over a 96-hr period.

Ensemble modeling has been used to address uncertainty and non-identifiability of parameter values and network structures for metabolic and biomolecular networks (Kuepfer et al., 2007; Jia et al., 2012). Using this method, libraries of models that exhibit equivalent goodness-of-fit to experimental data are used to discriminate among competing hypotheses (Geris et al., 2016). Ensemble models can be employed using local or global sampling of the initial guess for the optimization across regions of parameter space. Cross-validation and bootstrapping can be used to evaluate model predictive accuracy. To balance prediction accuracy and complexity, we can apply model selection techniques such as Akaike and the Bayesian information criterion (BIC). Feature selection can be used to pinpoint dominant higher-order interactions that shape community dynamics. Experiments can be selected based on the predicted variance of each model in the ensemble.

To elucidate the contribution of each species to a critical community-function that impacts human performance, we can interrogate SCFA production using a top-down approach. SCFA levels can be quantified for all leave-one-out communities at a single time point (~24 hr) using gas-chromatography mass spectrometry (GC-MS) using previously described methods (Krautkramer et al., 2016). Briefly, internal standards including acetate, propionate, and butyrate will be added to the samples containing flash-frozen filter-purified supernatant media. The samples can be acidified, extracted, and then injected onto an Agilent GC/MSD instrument. Quantification can be performed using selected ion monitoring and compared to relevant labeled internal standards. SCFA concentrations can be normalized to total biomass.

Single-cell analysis can be used to unravel the phenotypic properties of microbial populations and provide insight into the functions of diverse species in microbial communities. Building on our extensive experience in single-cell analysis (Venturelli et al., 2015; Venturelli et al., 2012), flow cytometry and microscopy coupled with dyes that detect nucleic acid content, enzymatic activity, membrane integrity, or metabolic activity can be used to examine functional properties of microbes in the full community and all leave-one-out sub-communities (Maurice et al., 2013). Fluorescence cell sorting combined with 16S rRNA gene sequencing (FACS-Seq) can be used to characterize phenotypically distinct sub-populations.

Statistical models can be used to analyze the relationships between community structure, activity and phenotypic properties. To unravel the contributions of each species to SCFA profiles, linear statistical models can be used to relate species abundance to SCFA concentrations using community structure data of the leave-one-out and full communities. Due to the underdetermined nature of the problem, we can use regularization to constrain the solution and cross-validation to compute the predictive capability of the model. Feature selection approaches such as stepwise regression can be applied to pinpoint species that contribute most significantly to the observed SCFA outputs. We can implement similar data analysis procedures to probe the relationship between community structure and phenotypes measured via flow cytometry (e.g. metabolic activity, DNA/RNA content, fraction of viable cells in the population). Together, these analyses can unravel the mapping between community structure, collective-functions and phenotypic characteristics.

Application of Methods to Investigating Other Microbiomes

The large-scale microbial interaction workflow provided herein can be applied to reverse engineer the ecological network of diverse microbiomes. The workflows and modeling approaches provided herein can be applied to interrogate the molecular and ecological principles of microbial community dynamics and activities across a broad range of environments. Genetic determinants of microbial community behaviors and inter-species interactions can be used as novel controllers for targeted microbiome editing. Defining the major abiotic and biotic forces that shape this system will have profound implications on the ability to modulate host physiology via targeted manipulation of the gut microbiota.

Application of Methods for Investigating Spatial/Physical Associated Between/Among Cells Our droplet-microfluidic workflow provided herein can be used to identify spatial associations between cells by encapsulating groups of adherent cells into a droplet and using the bead technology to barcode the aggregates. In this application, the barcode represents a physical association between or among cells.

Variations of Workflow Designs and Methods

The following examples describe variations on sequencing workflow methods to infer microbial interaction networks using droplet microfluidics.

As an overview of the workflow (FIGS. 17 and 18), the microbial community is first diluted in media and encapsulated into pico-liter droplets, such that there are 2 cells per droplet on average according to a Poisson distribution. Cells are randomly encapsulated into droplets at kilohertz rates, creating a large number of different consortia, with hundreds to thousands of replicates. The collected droplets are incubated to allow the community to assemble from a low number of cells. Next, the cell droplets are collected and loaded into a microfluidic device for merging of droplets containing cells with droplets containing barcoded beads and lysis buffer for concurrent cell lysis and capture of the 16S rRNA using barcoded beads. The merged droplets are collected and incubated on ice to allow 16S rRNA hybridization, before coalescing with perfluorooctanol (PFO) to collect the beads for cDNA synthesis using reverse transcriptase (RT). Following the RT reaction, the beads are incubated with the single-stranded exonuclease (Exo I) to remove oligonucleotides that are not associated with cDNA. Finally, the cDNA is amplified by PCR and purified for next-generation sequencing.

Figure 17:
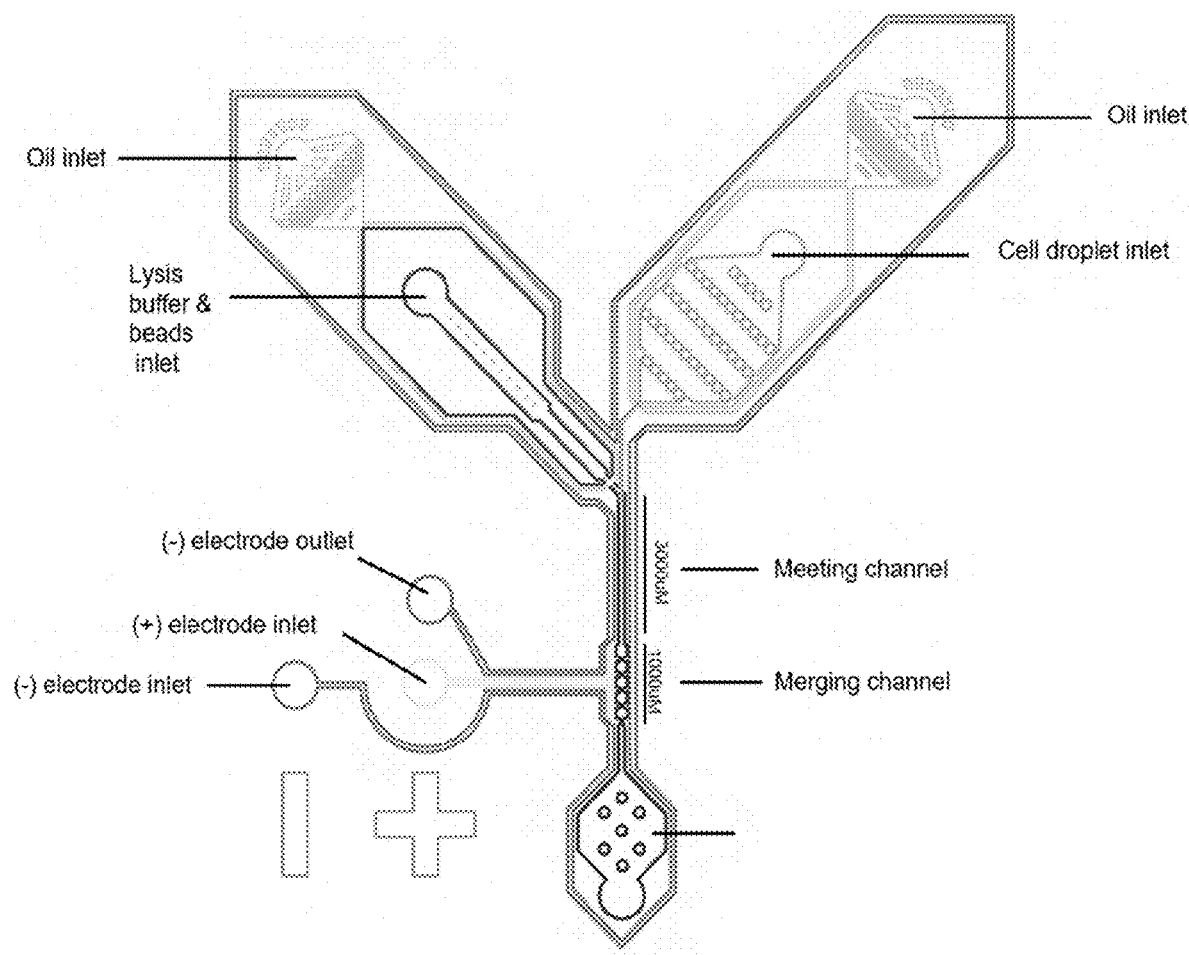
FIG. 17. Sequencing workflow overview and merger design. Design of merger device with longer meeting channels with channel expansions.
Figure 18:
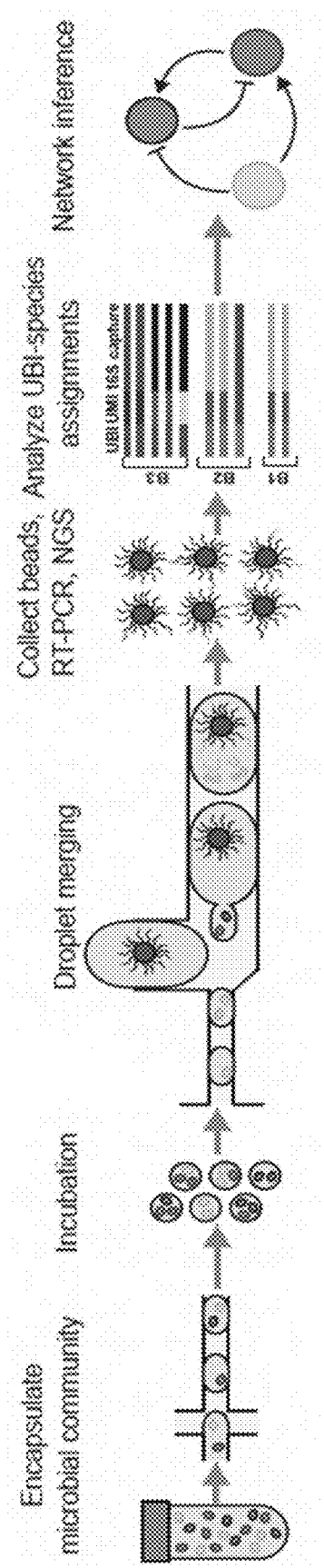
FIG. 18. Overview schematic of the sequencing workflow. A mixed microbial community and oil are loaded into a droplet-forming microfluidic device. Cells are randomly encapsulated into droplets based on a Poisson distribution. The droplets are incubated for a period of time to allow cell growth and division and then merged with barcoded beads for 16S rRNA capture. The barcoded beads droplets are then coalesced and washed, before performing reverse transcriptase, exonuclease treatment and PCR. The species identity based on the 16S sequences associated with UBI-UMI combinations are analyzed, and a microbial interaction network is inferred based on the difference in the data and the null model in the absence of a partner strain.

Merging rate can be inconsistent due to variation in the flow rates of cell droplets attributed to small variations in droplet size. To address that issue, we implemented a device with a longer meeting channel to allow cell droplets to catch up with the bead/lysis buffer droplets (FIG. 17). In addition, we extended the length and width of the merging channel to increase merging efficiency by increasing the length of exposure of droplets to the electric field. These modifications achieve a consistent merging efficiency.

In addition, we charged the lysis buffer channel (FIG. 17), which destabilizes the surfactants and allows the lysis buffer droplets to merge upon initial contact with the cell droplets. This approach improves specificity by reducing doublet formation.

Figure 19:
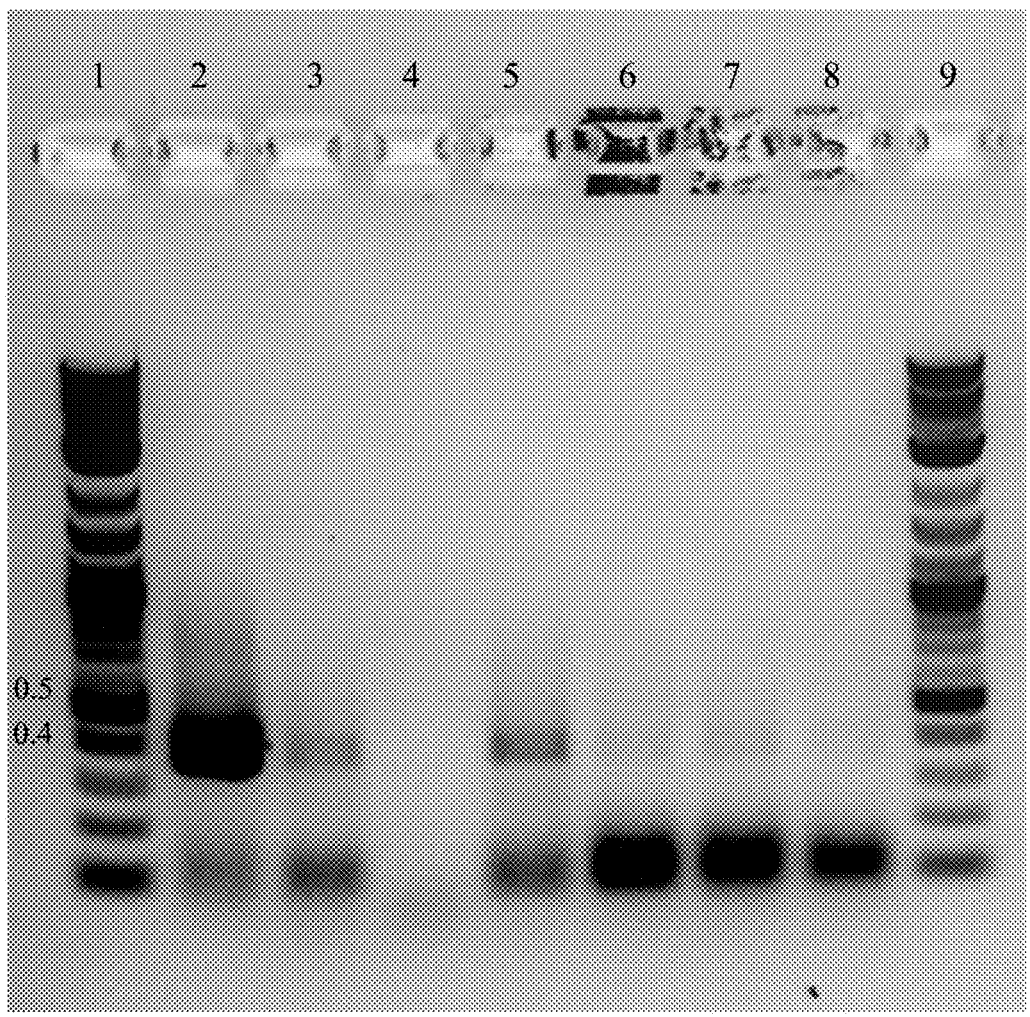
FIG. 19. Effect of salts on 16S rRNA capture and amplification. 1% agarose gel of PCR amplicons generated from cDNA of purified E. coli RNA hybridized with barcoded beads, and washed with different concentrations of $MgCl_2$ and NaCl. [1: 2-log base pair ladder, 2: RT positive control. Primers with full Illumina adapters for sequencing by [EZ] were used for PCR amplification of cDNA generated from reverse transcription of purified EC RNA using free oligo mimics of the bead oligos, 3: PCR amplification with [EZ] primers from cDNA generated from RT after washing 5000 EC RNA hybridized beads with 15 mM MgCl2, 4: Same as 3, but with the addition of 75 mM NaCl in wash buffer, 5: Same as 4, but with 0.5M NaCl, 6: Same as 3, but with 3 mM MgCl2 instead, 7: Same as 4, but with 3 mM MgCl2 instead, 8: Same as 5, but with 3 mM MgCl2 instead, 9: Same as 1]

Absence of salts in the lysis buffer can lead to inconsistent PCR bands. This variation is due to the absence of salts in the lysis buffer required for hybridization. We therefore added proteinase-K (0.4 mg/mL), 50 mM $MgCl_2$, and 0.5 M NaCl to the lysis buffer to result in consistent PCR bands (FIG. 19).

Figure 20:
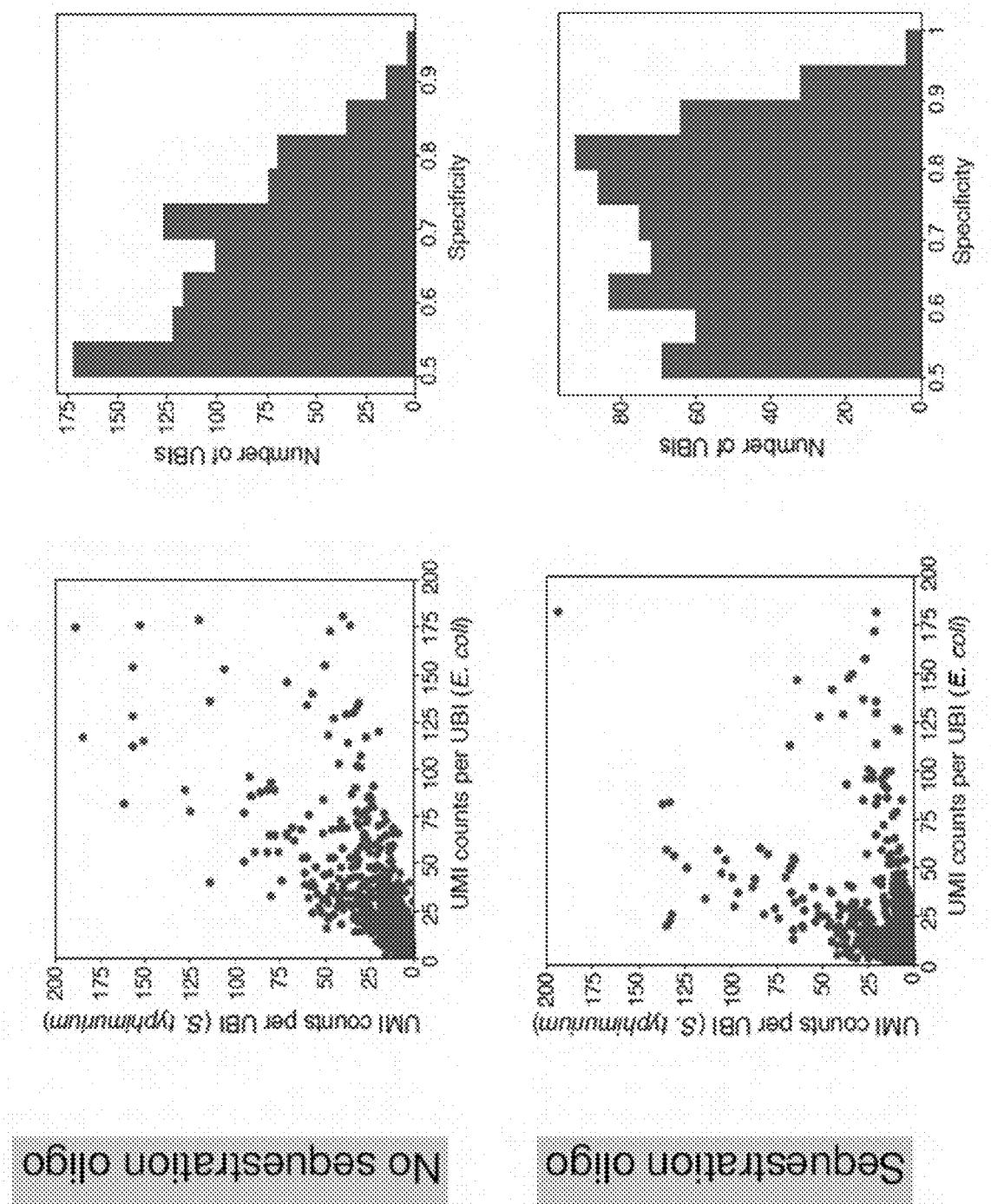
FIG. 20. Sequestering oligo improves specificity in test tubes. Scatter plots of the UMI counts per UBI for SE and EC. EC and ST total RNA were separately hybridized to beads. Top panels: Beads that were not treated with sequestering oligo and mixed in 30× dilution buffer. Bottom panels: Beads that were treated with 33 nM sequestering oligo and mixed together in 30× dilution buffer.

We carried out experiments to test for cross-hybridization of 16S rRNA between beads hybridized separately with ST or EC total RNA. First, we extracted RNA from EC or ST and mixed the total RNA of each species with beads in separate test tubes. Next, we mirrored the Drop-Seq protocol, by first mixing EC and ST hybridized beads in 30× dilution buffer (50 mM Tris, pH 7.5, 50 mM MgCl2, and 0.5 M NaCl) before washing a second time with another 30× dilution buffer. Our results showed two clusters, one with high ST and low EC or the reciprocal (FIG. 20, top panels). These data suggest that the beads were not fully saturated with 16S rRNA and could still cross-hybridize when mixed in 30× dilution buffer with the beads hybridized with the total RNA from the different species. To address this challenge, we aimed to substantially reduce two key parameters: unhybridized 16S rRNA in dilution buffer and unhybridized bead oligos. Adding 10-fold higher concentration of free sequestration oligos (oligos having the same elements as those bound to the beads but being unattached to beads and therefore free in solution) compared to the concentration of bead oligos to the dilution buffer before mixing improved the specificity (FIG. 20, bottom panels). Specificity is defined as ratio of the number of UMIs of the highest abundance 16S rRNA over the total number of UMIs for each UBI.

Figure 21:
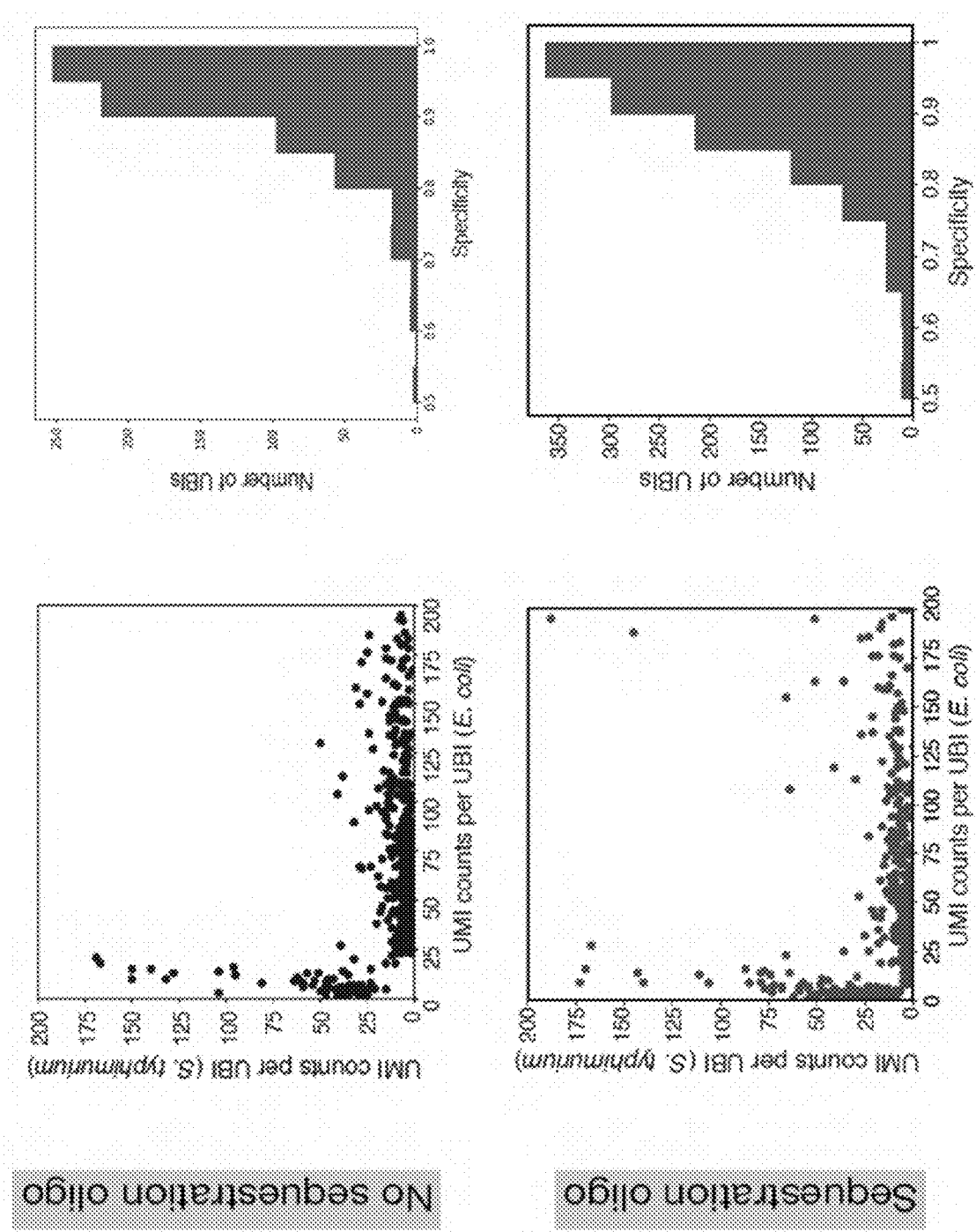
FIG. 21. Sequencing workflow in droplets has low cross-hybridization in the presence and absence of sequestering oligo. Scatter plots of S. typhimurium (Y-axis) and E. coli (X-axis) UMI counts per UBI from MiSeq run of merging separately encapsulated E. coli and S. typhimurium cells with beads. Specificity distributions of UBIs are plotted on right of scatter plots. Top panels: Beads that were not treated with sequestering oligo when mixed together in 30× dilution buffer. Bottom panels: Beads that were treated with 33 nM sequestering oligo when mixed together in 30× dilution buffer.

We separately encapsulated the beads in droplets with EC or ST total RNA. Our results showed low cross-hybridization in droplets in the presence and absence of the sequestration oligo (FIG. 21).

Figure 22:
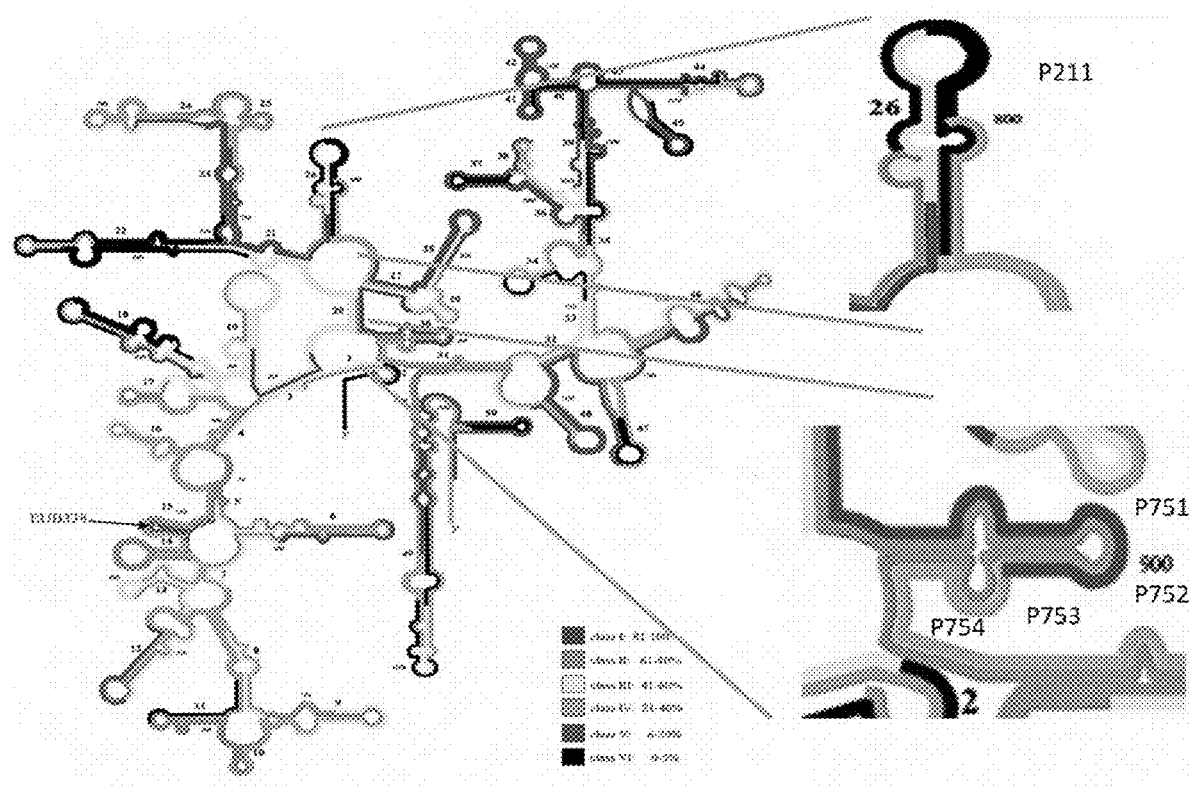
FIG. 22. Capture region optimization based on FISH probes. Distribution of relative fluorescence intensities of oligonucleotide probes, standardized to that of the brightest probe, Eco1482, on a 16S rRNA secondary structure model. Different colors indicate different brightness classes (I through VI). Current primer on barcoded beads (P211) is on class VI region, re-designed primers (P751-754) are on class I to class IV regions (Fuchs et al. 1998).
Figure 23A:
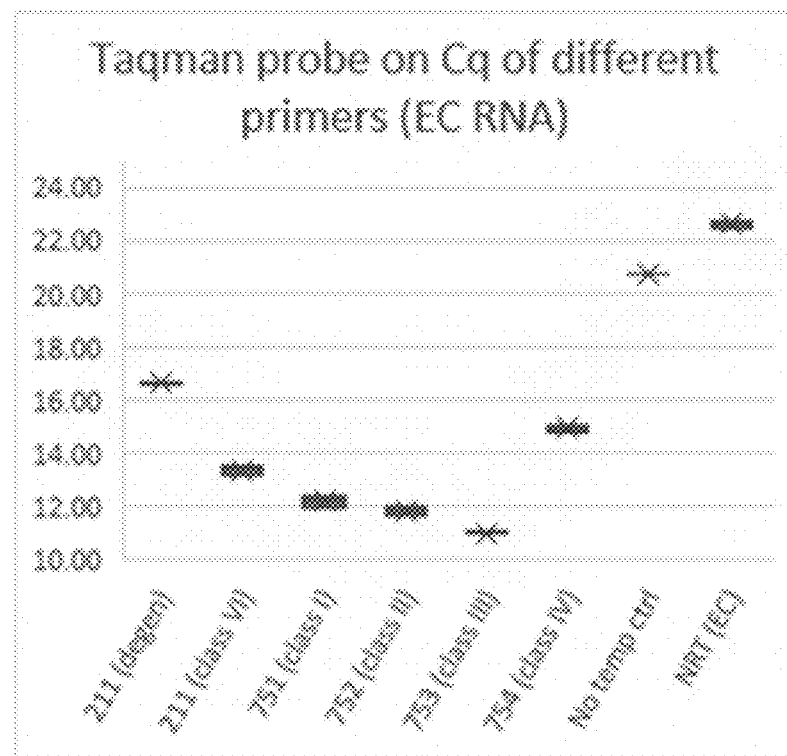
FIGS. 23A and 23B. Analysis of capture efficiency using quantitative real-time PCR. Box plot of Cq values for different annealing region of oligos annealing to 16SrRNA using Taqman probes. Current primer is 211 (degen) where the degeneracy in the primer sequence reduces the efficiency of the 16S rRNA capture compared to 211 (class VI) without degeneracy.
Figure 23B:
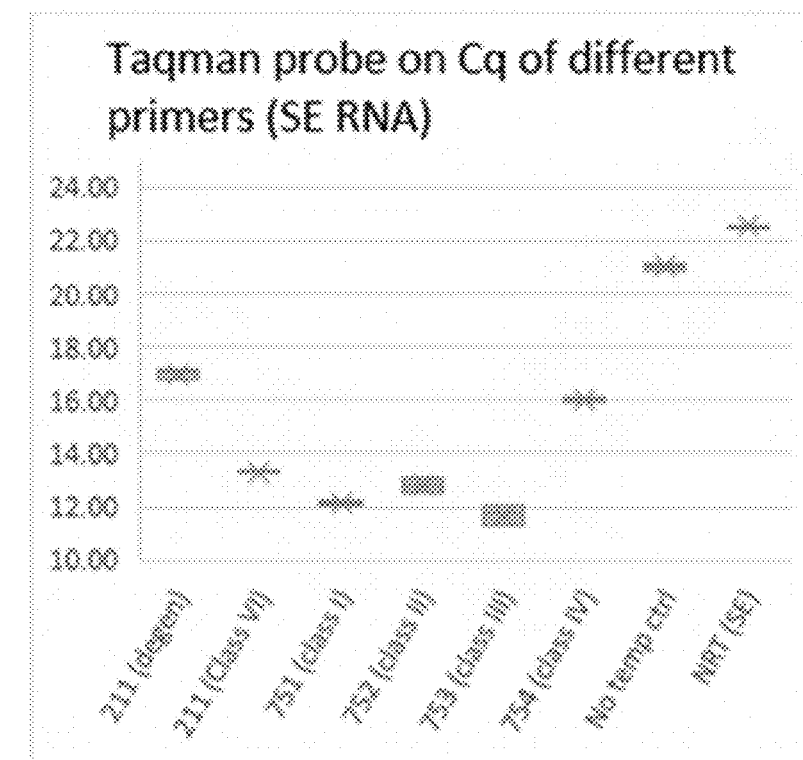

We also improved the capture sequence to improve the signal-to-noise ratio. We designed capture sequences based on a previous paper that analyzed the efficiency of FISH probes based on flow cytometry (Fuchs et al. 1998). We found that the first capture sequence is in a region with the lowest FISH signal, indicating that hybridization is not efficient in this region (FIG. 22). As such, we designed a new set of capture sequences based on the FISH signal. We used qPCR to determine the Cq value for each probe and identified sequences with a higher capture efficiency compared to the initial design (FIGS. 23A and 23B). The results show that 16S rRNA capture efficiency could be improved by at least 32-fold using the 753 (class III) primer.

Figure 24A:
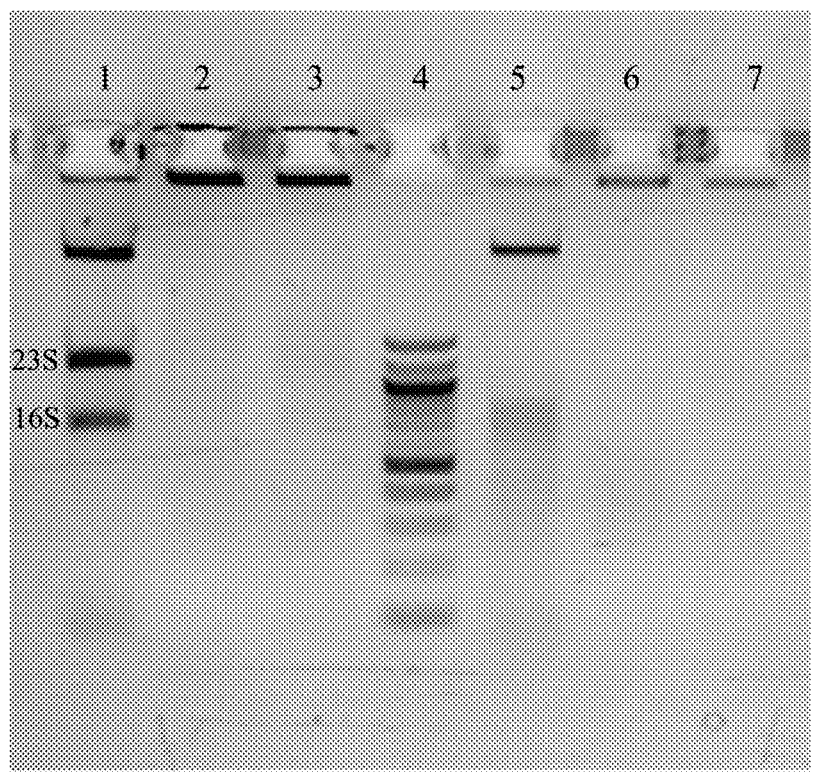
FIGS. 24A and 24B. Optimization of lysis buffer required for concurrent lysis and capture of 16S rRNA from *E. coli* and *S. typhimurium*.
Figure 24B:
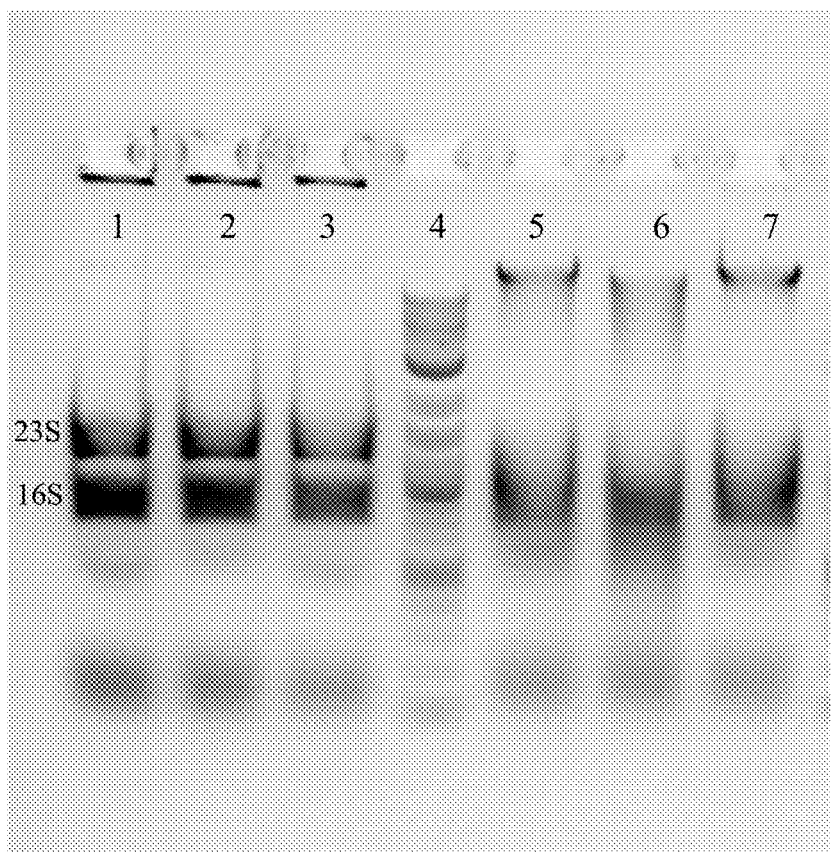

We operated the whole sequencing workflow, by lysing cells and hybridizing the 16S rRNA to the beads in droplets. Interestingly, proprietary lysis buffer (Lucigen QuickExtract RNA extraction kit) supplemented with proteinase K, failed to lyse cells in presence of salt (FIG. 24A). Therefore, we developed a new lysis buffer that includes 0.2% SDS, 0.5× BugBuster, proteinase-K (0.4 mg/mL), 50 mM $MgCl_2$, 0.5 M NaCl in 10 mM Tris and 1 mM EDTA buffer. This new lysis buffer is capable of lysing EC and ST in presence of salt required for hybridization (FIG. 24B).

Figures 25A, 25B:
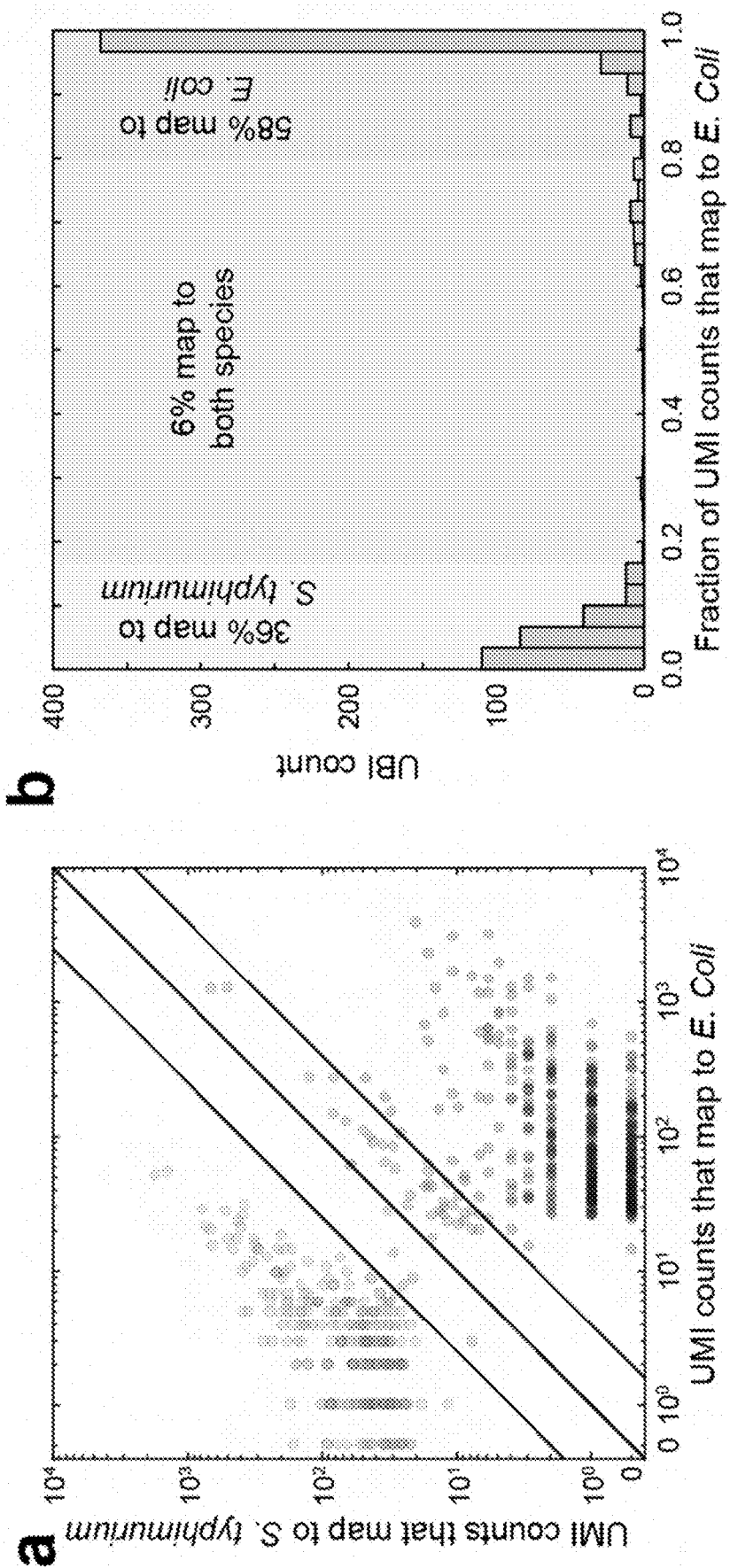
FIGS. 25A and 25B. Cross-hybridization control in the full sequencing workflow using separately encapsulated EC and ST populations.

We performed the sequencing workflow by merging droplets containing lysis buffer and barcoded beads with a mixture of droplets containing either ST or EC cells. Implementing the complete workflow with separately encapsulated ST and EC cells shows a low level of cross-talk (FIGS. 25A and 25B).

In this variation on sequencing workflow, we used 2M NaCl syringe tubes that were manually operated to fill the moat in the microfluidic merging device as shown in FIG. 17. Following that, the set up for tubes inserted into the merging microfluidic device were performed as described previously. The positive electrode was connected to the syringe of the bead suspension to charge the lysis buffer channel for merging. For this variation of merging experiments, typical flow rates were:
1. Beads in lysis buffer—800 µl/hr
2. Oil for beads—800 µL/hr
3. Cell droplets—20 µL/hr
4. Oil for cell droplets—100 µL/hr Following collection of merged droplets, perfluoroctanol was used to coalesce the droplets in 30× dilution buffer as described previously. Beads (containing hybridized 16S rRNA) were then collected, and washed a second time with another 30× dilution buffer before RT reaction. Next, the beads were spun down and washed thrice with 100 uL of $H_2O$, before ExoI exonuclease enzyme (NEB) treatment. Similarly, the thrice wash with 100 uL of $H_2O$ is repeated after ExoI treatment.

REFERENCES

Alain K, Querellou J (2009) Cultivating the uncultured: limits, advances and future challenges. Extremophiles 13: 583-594.

Bairey, E., Kelsic, E. D., and Kishony, R. "High-Order Species Interactions Shape Ecosystem Diversity" Nature Publishing Group 7, (2016): 1-7. doi:10.1038/ncomms12285

Baret J C, Miller O J, Taly V, Ryckelynck M, El-Harrak A, et al. (2009) Fluorescence-activated droplet sorting (FADS): efficient microfluidic cell sorting based on enzymatic activity. Lab on a Chip 9: 1850-1858.

Bartram A K, Lynch M D, Stearns J C, Moreno-Hagelsieb G, Neufeld J D (June 2011). "Generation of multimillion-sequence 16S rRNA gene libraries from complex microbial communities by assembling paired-end illumina reads". Applied and Environmental Microbiology. 77 (11): 3846-52.

Boedicker J Q, Vincent M E, Ismagilov R F (2009) Microfluidic Confinement of Single Cells of Bacteria in Small Volumes Initiates High-Density Behavior of Quorum Sensing and Growth and Reveals Its Variability. Angewandte Chemie-International Edition 48: 5908-5911.

Burke C M, Darling A E (2016-09-20). "A method for high precision sequencing of near full-length 16S rRNA genes on an Illumina MiSeq". PeerJ: e2492.

Chakravorty S, Helb D, Burday M, Connell N, Alland D (May 2007). "A detailed analysis of 16S ribosomal RNA gene segments for the diagnosis of pathogenic bacteria". Journal of Microbiological Methods. 69 (2): 330-9.

Clausell-Tormos J, Lieber D, Baret J C, El-Harrak A, Miller O J, et al. (2008) Droplet-based microfluidic platforms for the encapsulation and screening of mammalian cells and multicellular organisms. Chemistry & Biology 15:427-437.

Clauset, A., Newman, M. E. J., and Moore, C. "Finding Community Structure in Very Large Networks" Physical Review 70, no. 6 (2004): 66111.

Coenye T, Vandamme P (November 2003). "Intragenomic heterogeneity between multiple 16S ribosomal RNA operons in sequenced bacterial genomes". FEMS Microbiology Letters. 228 (1): 45-9.

Coyte, K. Z., Schluter, J., and Foster, K. R. "The Ecology of the Microbiome: Networks, Competition, and Stability" Science 350, no. 6261 (2015): 663-666.

Faith, J. J., Ahern, P. P., Ridaura, V. K., Cheng, J., and Gordon, J. I. "Identifying Gut Microbe-Host Phenotype Relationships Using Combinatorial Communities in Gnotobiotic Mice." Science translational medicine 6, no. 220 (2014): 220ra11. doi:10.1126/scitranslmed.3008051

Faith, J. J., McNulty, N. P., Rey, F. E., and Gordon, J. I. "Predicting a Human Gut Microbiota's Response to Diet in Gnotobiotic Mice." Science 333, no. 6038 (2011): 101-4. doi:10.1126/science.1206025

Faust, K. and Raes, J. "Microbial Interactions: From Networks to Models." Nature reviews. Microbiology 10, no. 8 (2012): 538-50. doi:10.1038/nrmicro2832

Ferrari B C, Binnerup S J, Gillings M (2005) Microcolony cultivation on a soil substrate membrane system selects for previously uncultured soil bacteria. Applied and Environmental Microbiology 71: 8714-8720.

Ferrari B C, Winsley T, Gillings M, Binnerup S (2008) Cultivating previously uncultured soil bacteria using a soil substrate membrane system. Nature Protocols 3: 1261-1269.

Foster, K. R., Bell, T., 2012. Competition, not cooperation, dominates interactions among culturable microbial species. Curr. Biol. 22, 1845-1850. https://doi.org/10.1016/j.cub.0.2012.08.005

Friedman, J. and Alm, E. J. "Inferring Correlation Networks from Genomic Survey Data." PLoS computational biology 8, no. 9 (2012): e1002687. doi:10.1371/journal.pcbi.1002687

Fuchs, M., Wallner, G., Beisker, W., Schwippl, I., Ludwig, W., and Amann, R. (1998). Flow Cytometric Analysis of the In Situ Accessibility of *Escherichia coli* 16S rRNA for Fluorescently Labeled Oligonucleotide Probes. Appl. Environ. Microbiol. 64 (12), 4973-4982.

Fujimoto, T., Imaeda, H., Takahashi, K., Kasumi, E., Bamba, S., Fujiyama, Y., and Andoh, A. "Decreased Abundance of *Faecalibacterium Prausnitzii* in the Gut Microbiota of Crohn's Disease." Journal of gastroenterology and hepatology 28, no. 4 (2013): 613-9. doi:10.1111/jgh.12073

Geris, L. and Gomez-Cabrero, D. "Uncertainty in Biology: A Computational Modeling Approach" 17, (2016): doi: 10.1007/978-3-319-21296-8

Gray M W, Sankoff D, Cedergren R J (1984). "On the evolutionary descent of organisms and organelles: a global phylogeny based on a highly conserved structural core in small subunit ribosomal RNA". Nucleic Acids Research. 12 (14): 5837-52.

Guo, M. T., Rotem, A., Heyman, J. A., and D. A. Weitz. "Droplet Microfluidics for High-Throughput Biological Assays." Lab on a Chip 12, no. 12 (2012): 2146-55. doi:10.1039/c21c21147e Grodrian A, Metze J, Henkel T, Martin K, Roth M, et al. (2004) Segmented flow generation by chip reactors for highly parallelized cell cultivation. Biosensors & Bioelectronics 19: 1421-1428.

Hammarlund, S. P., Chacón, J. M., Harcombe, W. R., 2018. A shared limiting resource leads to competitive exclusion in a cross-feeding system 1-20.

Hatori M N, Kim S C, Abate A R. Particle-Templated Emulsification for Microfluidics-Free Digital Biology. Anal Chem. 2018 August 21; 90(16):9813-9820.

Holtze, C., Rowat, A. C., Agresti, J. J., Hutchison, J. B., Angile, F. E., Schmitz, C. H. J., Koster, S., Duan, H., Humphry, K. J., Scanga, R. A., Johnson, J. S., Pisignano, D., Weitz, D. A., 2008. Biocompatible surfactants for water-in-fluorocarbon emulsions. Lab Chip 8, 1632. https://doi.org/10.1039/b806706f Ingham C J, Sprenkels A, Bomer J, Molenaar D, van den Berg A, et al. (2007) The micro-Petri dish, a million-well growth chip for the culture and hightthroughput screening of microorganisms. Proceedings of the National Academy of Sciences of the United States of America 104: 18217-18222.

Inoue I, Wakamoto Y, Moriguchi H, Okano K, Yasuda K (2001) On-chip culture system for observation of isolated individual cells. Lab on a Chip 1: 50-55.

Jia, G., Stephanopoulos, G., and Gunawan, R. "Ensemble Kinetic Modeling of Metabolic Networks from Dynamic Metabolic Profiles" Metabolites 2, (2012): 891-912. doi: 10.3390/metabo2040891

Jovel J, Patterson J, Wang W, Hotte N, O'Keefe S, Mitchel T, Perry T, Kao D, Mason A L, Madsen K L, Wong G K (2016-01-01). "Characterization of the Gut Microbiome Using 16S or Shotgun Metagenomics". Frontiers in Microbiology. 7: 459.

Kaeberlein T, Lewis K, Epstein S S (2002) Isolating "uncultivable" microorganisms in pure culture in a simulated natural environment. Science 296:1127-1129.

Karbaschi, M., Shahi, P., Abate, A. R., 2017. Rapid, chemical-free breaking of microfluidic emulsions with a handheld antistatic gun. Biomicrofluidics. https://doi.org/10.1063/1.4995479

Koster S, Angile F E, Duan H, Agresti J J, Wintner A, et al. (2008) Drop-based microfluidic devices for encapsulation of single cells. Lab on a Chip 8:1110-1115.

Klein, A. M., Mazutis, L., Akartuna, I., Tallapragada, N., Veres, A., Li, V., Peshkin, L., Weitz, D. A., and Kirschner, M. W. "Droplet Barcoding for Single-Cell Transcriptomics Applied to Embryonic Stem Cells" Cell 161, no. 5 (2015): 1187-1201. doi:10.1016/j.cell.2015.04.044

Krautkramer K A, Kreznar J H, Romano K A, Vivas E I, Barrett-Wilt G A, Rabaglia M E, Keller M P, Attie A D, Rey F E, Denu J M. Diet-Microbiota Interactions Mediate Global Epigenetic Programming in Multiple Host Tissues. Mol Cell. 2016 Dec. 1; 64(5):982-992. doi: 10.1016/j.molcel.2016.10.025.

Kuepfer, L., Peter, M., Sauer, U., and Stelling, J. "Ensemble Modeling for Analysis of Cell Signaling Dynamics" Nature biotechnology 25, no. 9 (2007): 1001-1006. doi: 10.1038/nbt1330

Liu W S, Kim H J, Lucchetta E M, Du W B, Ismagilov R F (2009) Isolation, incubation, and parallel functional testing and identification by FISH of rare microbial single-copy cells from multi-species mixtures using the combination of chemistrode and stochastic confinement. Lab on a Chip 9: 2153-2162.

Lovell, D., Pawlowsky-glahn, V., Egozcue, J. J., and Marguerat, S. "Proportionality: A Valid Alternative to Correlation for Relative Data" PLOS Computational biology 11, no. 3 (2015): 1-12. doi:10.1371/journal.pcbi.1004075

'Macosko, E. Z., Basu, A., Satija, R., Nemesh, J., Shekhar, K., Goldman, M., Tirosh, I., Bialas, A. R., Kamitaki, N., Martersteck, E. M., Trombetta, J. J., Weitz, D. A., Sanes, J. R., Shalek, A. K., Regev, A., McCarroll, S. A., 2015. Highly parallel genome-wide expression profiling of individual cells using nanoliter droplets. Cell 161, 1202-1214. https://doi.org/10.1016/j.cell.2015.05.002

Martin K, Henkel T, Baier V, Grodrian A, Schon T, et al. (2003) Generation of larger numbers of separated microbial populations by cultivation in segmented-flow microdevices. Lab on a Chip 3: 202-207.

Maurice, C. F. and Turnbaugh, P. J. "Quantifying the Metabolic Activities of Human-Associated Microbial Communities across Multiple Ecological Scales" FEMS Microbiology Reviews 37, (2013): 830-848. doi:10.1111/1574-6976.12022

Mounier, J., Monnet, C., Vallaeys, T., Arditi, R., Sarthou, A.-S., Hélias, A., and Irlinger, F. "Microbial Interactions within a Cheese Microbial Community." Applied and environmental microbiology 74, no. 1 (2008): 172-81. doi:10.1128/AEM.01338-07

Park, J., Kerner, A., Burns, M. A., and Lin, X. N. "Microdroplet-Enabled Highly Parallel Co-Cultivation of Microbial Communities" PLoS ONE 6, no. 2 (2011): doi: 10.1371/journal.pone.0017019

Qin, J., Li, Y., Cai, Z., Li, S., Zhu, J., Zhang, F., Liang, S., Zhang, W., Hansen, T., Sanchez, G., Raes, J., Falony, G., Okuda, S., and Almeida, M. "A Metagenome-Wide Association Study of Gut Microbiota in Type 2 Diabetes" Nature 490, no. 7418 (2012): 55-60. doi:10.1038/nature11450

Qin, J., Li, R., Raes, J., Arumugam, M., Burgdorf, K. S., Manichanh, C., Nielsen, T., Pons, N., Levenez, F., Yamada, T., Mende, D. R., Li, J., Xu, J., Li, S., Li, D., Cao, J., Wang, B., Liang, H., Zheng, H., Xie, Y., Tap, J., Lepage, P., Bertalan, M., Batto, J.-M., Hansen, T., Paslier, D. Le, Linneberg, A., Nielsen, H. B., Pelletier, E., Renault, P., Sicheritz-Ponten, T., Turner, K., Zhu, H., Yu, C., Li, S., Jian, M., Zhou, Y., Li, Y., Zhang, X., Li, S., Qin, N., Yang, H., Wang, J., Brunak, S., Dore, J., Guarner, F., Kristiansen, K., Pedersen, O., Parkhill, J., Weissenbach, J., Bork, P., Ehrlich, S. D., and Wang, J. "A Human Gut Microbial Gene Catalogue Established by Metagenomic Sequencing." Nature 464, no. 7285 (2010): 59-65. doi: 10.1038/nature08821

Romero, P. A. and Abate, A. R. "Flow Focusing Geometry Generates Droplets through a Plug and Squeeze Mechanism" Lab on a Chip 12, no. 24 (2012): 5130-5132. doi:10.1039/c21c40938k Romero, P. A., Tran, T. M., and Abate, A. R. "Dissecting Enzyme Function with Microfluidic-Based Deep Mutational Scanning" Proceedings of the National Academy of Sciences 112, no. 23 (2015): 7159-7164. doi:10.1073/pnas.1422285112

Rotem, A., Ram, O., Shoresh, N., Sperling, R. A., Schnall-Levin, M., Zhang, H., Basu, A., Bernstein, B. E., and Weitz, D. A. "High-Throughput Single-Cell Labeling (Hi-SCL) for RNA-Seq Using Drop-Based Microfluidics" PLoS ONE 10, no. 5 (2015): 1-14. doi:10.1371/journal.pone.0116328

Scher, J. U., Sczesnak, A., Longman, R. S., Segata, N., Ubeda, C., Bielski, C., Rostron, T., Cerundolo, V., Pamer, E. G., Abramson, S. B., Huttenhower, C., and Littman, D. R. "Expansion of Intestinal *Prevotella Copri* Correlates with Enhanced Susceptibility to Arthritis." eLife 2, (2013): e01202. doi:10.7554/eLife.01202

Smith, T., Heger, A., Sudbery, I., 2017. UMI-tools: modeling sequencing errors in Unique Molecular Identifiers to improve quantification accuracy. Genome Res. 27, 491-499. https://doi.org/10.1101/gr.209601.116

Spencer, S. J., Tamminen, M. V, Preheim, S. P., Guo, M. T., Briggs, A. W., Brito, I. L., Weitz, D. A., Pitkanen, L. K., Vigneault, F., Virta, M. P. J., and Alm, E. J. "Massively Parallel Sequencing of Single Cells by epicPCR Links Functional Genes with Phylogenetic Markers" ISME 10, (2016): 427-436. doi:10.1038/ismej.2015.124

Stein, R. R., Bucci, V., Toussaint, N. C., Buffie, C. G., Ratsch, G., Pamer, E. G., Sander, C., and Xavier, J. B. "Ecological Modeling from Time-Series Inference: Insight into Dynamics and Stability of Intestinal Microbiota." PLoS computational biology 9, no. 12 (2013): e1003388. doi:10.1371/journal.pcbi.1003388

Thota, V. R., Dacha, S., and Natarajan, A. "*Eggerthella Lenta* Bacteremia in a Crohn's Disease Patient after Ileocecal Resection" Future Microbiology 6, (2011): 595-597.

Tsukuda, Miyuki; Kitahara, Kei; Miyazaki, Kentaro (2017-08-30). "Comparative RNA function analysis reveals high functional similarity between distantly related bacterial 16 S rRNAs". Scientific Reports. 7 (1).

Van de Peer Y, Chapelle S, De Wachter R (1996). "A quantitative map of nucleotide substitution rates in bacterial rRNA". Nucleic Acids Research. 24 (17): 3381-91.

Venturelli, O. S., El-Samad, H., and Murray, R. M. "Synergistic Dual Positive FeedbackLoops Established by Molecular Sequestration Generate Robust Bimodal Response" Proceedings of the National Academy of Sciences 109, no. 48 (2012): doi:10.1073/pnas.1211902109

Venturelli O S, Carr A C, Fisher G, Hsu R H, Lau R, Bowen B P, Hromada S, Northen T, Arkin A P. Deciphering microbial interactions in synthetic human gut microbiome communities. Mol Syst Biol. 2018 Jun. 21; 14(6):e8157.

Venturelli, O. S., Tei, M., Bauer, S., Chan, L. J. G., Petzold, C. J., Arkin, A. P., 2017. Programming mRNA decay to modulate synthetic circuit resource allocation. Nat. Commun. 8,15128. https://doi.org/10.1038/ncomms15128

Venturelli, O. S., Zuleta, I., Murray, R. M., and El-Samad, H. "Population Diversification in a Yeast Metabolic Program Promotes Anticipation of Environmental Shifts" PLoS Biology 109, no. 48 (2015): E3324-E3333. doi:10.1371/journal.pbio.1002042

Větrovský T, Baldrian P (2013-02-27). "The variability of the 16S rRNA gene in bacterial genomes and its consequences for bacterial community analyses". PLoS One. 8 (2): e57923.

Weisburg W G, Barns S M, Pelletier D A, Lane D J (January 1991). "16S ribosomal DNA amplification for phylogenetic study". Journal of Bacteriology. 173 (2): 697-703.

Woese C R, Fox G E (November 1977). "Phylogenetic structure of the prokaryotic domain: the primary kingdoms". Proceedings of the National Academy of Sciences of the United States of America. 74 (11): 5088-90.

Yang B, Wang Y, Qian P Y (March 2016). "Sensitivity and correlation of hypervariable regions in 16S rRNA genes in phylogenetic analysis". BMC Bioinformatics. 17 (1): 135.

Zeitoun, R. I., Garst, A. D., Degen, G. D., Pines, G., Mansell, T. J., Glebes, T. Y., Boyle, N. R., and Gill, R. T. "Multiplexed Tracking of Combinatorial Genomic Mutations in Engineered Cell Populations." Nature Biotechnology 33, no. 6 (2015): 631-637.

Zengler K, Toledo G, Rappe M, Elkins J, Mathur E J, et al. (2002) Cultivating the uncultured. Proceedings of the National Academy of Sciences of the United States of America 99: 15681-15686.

Versions of the Invention

Some versions of the invention comprise providing cell-containing liquid droplets. Each cell-containing liquid droplet in some versions contain a separate set of cells. Each cell in each set of cells in some versions comprise a target nucleic acid comprising a target sequence and a cell identifier sequence that identifies a type of cell.

Some versions further comprise providing oligonucleotide-containing liquid droplets. Each oligonucleotide-containing liquid droplet in some versions contains a separate set of oligonucleotides. Each oligonucleotide in each set of oligonucleotides in some versions comprises a set identifier sequence that identifies a single set of oligonucleotides among the sets of oligonucleotides and a capture sequence that is structured to hybridize to the target sequences.

Some versions further comprise merging the cell-containing liquid droplets with the oligonucleotide-containing liquid droplets to form merged droplets.

Some versions further comprise hybridizing the oligonucleotides to the target nucleic acids within the merged droplets by hybridizing the capture sequences to the target sequences to thereby generate hybridized oligonucleotides.

Some versions further comprise extending the hybridized oligonucleotides beyond the cell identifier sequences on the target nucleic acids serving as templates to thereby generate extended oligonucleotides comprising the cell identifier sequences.

Some versions further comprise determining the cell identifier sequence and the set identifier sequence on each extended oligonucleotide to thereby identify each type of cell present in each set of cells.

The determining step in some versions comprise sequencing the extended oligonucleotides to thereby generate sequence reads of the extended oligonucleotides. Each sequence read in some versions comprise a set identifier sequence read and a cell identifier sequence read. Each set identifier sequence read in some versions is a sequence read of one of the set identifier sequences. Each cell identifier sequence read in some versions is a sequence read of one of the cell identifier sequences. The determining step in some versions further comprise associating the cell identifier sequence read and the set identifier sequence read on each sequence read. The determining step in some versions further comprise grouping the sequence reads into groups comprising statistically identical set identifier sequence reads. The determining step in some versions further comprise grouping, within each group of sequence reads, the cell identifier reads into groups of statistically identical cell identifier reads.

In some versions, the merged droplets resulting from merging the cell-containing liquid droplets with the oligonucleotide-containing liquid droplets are not diluted or merged with additional liquid droplets prior to the hybridizing.

In some versions, the merged droplets containing the hybridized oligonucleotides are coalesced prior to the extending.

In some versions, each oligonucleotide further comprises a molecule identifier sequence. Each molecule identifier sequence in some versions identifies a single oligonucleotide within the set of oligonucleotides in which the single oligonucleotide is comprised. The determining step in some versions comprises determining the cell identifier sequence, the set identifier sequence, and the molecule identifier sequence on each extended oligonucleotide to thereby identify and quantitate the number of each type of cell present in each set of cells. The determining step in some versions further comprises sequencing the extended oligonucleotides to thereby generate sequence reads of the extended oligonucleotides. Each sequence read in some versions comprises a molecule identifier sequence read, a set identifier sequence read, and a cell identifier sequence read. Each molecule identifier sequence read in some versions is a sequence read of one of the molecule identifier sequences. Each set identifier sequence read in some versions is a sequence read of one of the set identifier sequences. Each cell identifier sequence read in some versions is a sequence read of one of the cell identifier sequences. Some versions further comprise associating the cell identifier sequence read, the set identifier sequence read, and the molecule identifier sequence read on each sequence read. Some versions further comprise grouping the sequence reads into groups comprising statistically identical set identifier sequence reads. Some versions further comprise grouping, within each group of sequence reads, the cell identifier reads into groups of statistically identical cell identifier reads. Some versions further comprise determining, within each group of sequence reads, a number of unique molecule identifier sequence reads associated with each group of statistically identical cell identifier reads.

Some versions further comprise, after the merging and prior to the hybridizing, lysing the cells. Each oligonucleotide-containing liquid droplet in some versions further comprises a lysis reagent. The lysing in some versions comprises incubating the cells in the merged droplet in the presence of the lysis reagent.

In some versions, the oligonucleotides and the lysis reagent are contained within the oligonucleotide-containing liquid droplets in a salt-containing buffer.

In some versions, the cell-containing liquid droplets, the oligonucleotide-containing liquid droplets, and the merged liquid droplets are aqueous liquid droplets encapsulated by an immiscible medium.

Some versions further comprise isolating the sets of cells or precursor sets of cells from a single mixture of cells to thereby provide the cell-containing liquid droplets or cell-containing liquid droplet precursors, respectively.

Some versions further comprise isolating precursor sets of cells from a single mixture of cells to thereby provide cell-containing liquid droplet precursors. Some versions further comprise after the isolating and before the merging, incubating cell-containing liquid droplet precursors at a growth temperature for a period of time to thereby provide the cell-containing liquid droplets. In some versions, at least one of the cells in at least one of the precursor sets affects growth of at least one other of the cells in the at least one of the precursor sets during the incubating. In some versions, the number of total cells isolated in each precursor set comprises no more than 10 cells.

In some versions, the molecule identifier sequences among the oligonucleotides within each merged droplet are all different from each other.

In some versions, the set identifier sequences among the oligonucleotides within each merged droplet are identical to each other.

In some versions, the set identifier sequences among the oligonucleotides within each merged droplet is different from the set identifier sequences among the oligonucleotides of each of the other merged droplets.

In some versions, each capture sequence is capable of hybridizing to the target sequence in the target nucleic acid of at least one of the cells under solution conditions of the merged droplets. In some versions, each capture sequence is capable of hybridizing to the target sequence in the target nucleic acid of each of the cells under solution conditions of the merged droplets.

In some versions, the target sequence in the target nucleic acid of each of the cells in each set is capable of hybridizing to at least one of the capture sequences under solution conditions of the merged droplets. In some versions, the target sequence in the target nucleic acid of each of the cells in each set is capable of hybridizing to each of the capture sequences under solution conditions of the merged droplets.

In some versions, the cell identifier sequence of at least one of the cells in at least one of the sets is different from the cell identifier sequence of at least one other of the cells in the at least one of the sets.

In some versions, the cell identifier sequence of at least one of the cells in the at least one of the sets is not present among the cells in at least one other of the sets.

In some versions, the molecule identifier sequences among oligonucleotides in each set of oligonucleotides are different from each other.

In some versions, the set identifier sequences of the oligonucleotides in each set of oligonucleotides are different from the set identifier sequences of the oligonucleotides in each other set of oligonucleotides.

The merging in some versions merges each cell-containing liquid droplet with no more than one oligonucleotide-containing liquid droplet.

The oligonucleotides in each set of oligonucleotides in some versions are attached to a single solid substrate.

Some versions further comprise, after the extending and before the determining, amplifying the extended oligonucleotide.

Some versions comprise isolating a cell in a liquid droplet encapsulated by an immiscible medium to thereby generate a cell droplet, wherein the cell droplet is a cell-containing liquid droplet or a precursor thereof, and wherein the cell comprises a target nucleic acid comprising a target sequence and a cell identifier sequence. Some versions further comprise merging the cell droplet within the immiscible medium with an oligonucleotide-containing droplet to thereby generate a merged droplet comprising the cell, a cell-lysis reagent, and an oligonucleotide, wherein the oligonucleotide comprises a molecule identifier sequence and a capture sequence, and wherein the capture sequence is capable of hybridizing to the target sequence in the target nucleic acid of the cell under solution conditions of the merged droplet. Some versions further comprise incubating the merged droplet within the immiscible medium to permit lysis of the cell and hybridization of the capture sequence to the target sequence to thereby generate a hybridized oligonucleotide. Some versions further comprise extending the hybridized oligonucleotide along the target nucleic acid serving as a template to thereby generate an extended oligonucleotide, the extended oligonucleotide comprising the molecule identifier sequence, the capture sequence, and the cell identifier sequence. Some versions further comprise sequencing the extended oligonucleotide to thereby generate a sequence read of the extended oligonucleotide, the sequence read comprising a molecule identifier sequence read and a cell identifier sequence read, wherein the molecule identifier sequence read is a sequence read of the molecule identifier sequence and the cell identifier sequence read is a sequence read of the cell identifier sequence. Some versions, further comprise associating the cell identifier sequence read with the molecule identifier sequence read to thereby identify the isolated cell by its cell identifier sequence. In some versions, the cell is isolated from a population of cells. Some versions further comprise, between the isolating and the merging, incubating the cell droplet within the immiscible medium at a growth temperature for a period of time. Some versions further comprise, between the extending and the sequencing, amplifying the extended oligonucleotide.

Some versions comprise isolating a set of cells in a liquid droplet encapsulated by an immiscible medium to thereby generate a cell droplet, wherein the cell droplet is a cell-containing liquid droplet or a precursor thereof. In some versions, each of the cells in the set comprises a target nucleic acid comprising a target sequence and a cell identifier sequence. In some versions, the cell identifier sequence of at least one of the cells in the set is different from the cell identifier sequence of at least one other of the cells in the set. Some versions further comprise merging the cell droplet within the immiscible medium with a oligonucleotide-containing liquid droplet to thereby generate a merged droplet comprising the set of cells, the cell-lysis reagent, and oligonucleotides. In some versions, each of the oligonucleotides comprises a molecule identifier sequence and a capture sequence. In some versions, the molecule identifier sequences within the merged droplet are all different from each other. In some versions, each capture sequence is capable of hybridizing to the target sequence in the target nucleic acid of at least one of the cells in the set under solution conditions of the merged droplet. In some versions, the target sequence in the target nucleic acid of each of the cells in the set is capable of hybridizing to at least one of the capture sequences under solution conditions of the merged droplet. In some versions, the incubating the merged droplet within the immiscible medium permits lysis of each of the cells in the set and hybridization of the target sequence in the target nucleic acid of each of the cells in the set to at least one of the capture sequences to thereby generate hybridized oligonucleotides. Some versions further comprise extending the hybridized oligonucleotides along the target nucleic acids serving as templates to thereby generate extended oligonucleotides, each extended oligonucleotide comprising the molecule identifier sequence, the capture sequence, and the cell identifier sequence. Some versions further comprise sequencing the extended oligonucleotides to thereby generate sequence reads of the extended oligonucleotides, each sequence read comprising a molecule identifier sequence read and a cell identifier sequence read, wherein each molecule identifier sequence read is a sequence read of one of the molecule identifier sequences and each cell identifier sequence read is a sequence read of one of the cell identifier sequences. Some versions further comprise associating each cell identifier sequence read with the molecule identifier sequence read within each sequence read. Some versions further comprise grouping the cell identifier reads into groups of statistically identical cell identifier reads. Some versions further comprise determining a number of unique molecule identifier sequence reads associated with each group of statistically identical cell identifier reads. In some versions, the set of cells is isolated from a larger population of cells. In some versions, the number of total cells isolated in the set comprises no more than 10 cells. In some versions, the merging comprises merging the cell droplet within the immiscible medium with one and only one aqueous liquid droplet comprising the cell-lysis reagent and the oligonucleotides. Some versions further comprise between the isolating and the merging, incubating the cell droplet within the immiscible medium at a growth temperature for a period of time. In some versions, at least one of the cells in the set affects growth of at least one other of the cells in the set. Some versions, further comprise, between the extending and the sequencing, amplifying the extended oligonucleotide.

Some versions comprise isolating sets of cells in aqueous liquid droplets encapsulated by the immiscible medium to thereby generate cell droplets, wherein the cell droplets are a cell-containing liquid droplet or a precursor thereof. In some versions, each set of cells is isolated in a separate aqueous liquid droplet. In some versions, each of the cells in each of the sets comprises a target nucleic acid comprising a target sequence and a cell identifier sequence. In some versions, the cell identifier sequence of at least one of the cells in at least one of the sets is different from the cell identifier sequence of at least one other of the cells in the at least one of the sets. In some versions, the cell identifier sequence of the at least one of the cells in the at least one of the sets is not present among the cells in at least one other of the sets. Some versions further comprise merging the cell droplets within the immiscible medium with oligonucleotide-containing liquid droplets to thereby generate merged droplets, each merged droplet comprising one of the sets of cells, the cell-lysis reagent, and oligonucleotides. In some versions, each of the oligonucleotides comprises a molecule identifier sequence, a set identifier sequence, and a capture sequence. In some versions, the molecule identifier sequences within each merged droplet are all different from each other. In some versions, the set identifier sequences among the oligonucleotides within each merged droplet are identical to each other and are different from the set identifier sequences among the oligonucleotides within each of the other merged droplets. In some versions, each capture sequence is capable of hybridizing to the target sequence in the target nucleic acid of at least one of the cells of the sets under solution conditions of the merged droplets. In some versions, the target sequence in the target nucleic acid of each of the cells in each set is capable of hybridizing to at least one of the capture sequences under solution conditions of the merged droplets. In some versions, the incubating the merged droplet within the immiscible medium permits lysis of each of the cells in the sets and hybridization of the target sequence in the target nucleic acid of each of the cells in the sets to at least one of the capture sequences to thereby generate hybridized oligonucleotides. Some versions further comprise extending the hybridized oligonucleotides along the target nucleic acids serving as templates to thereby generate extended oligonucleotides, each extended oligonucleotide comprising the molecule identifier sequence, the capture sequence, the set identifier sequence, and the cell identifier sequence. Some versions further comprise sequencing the extended oligonucleotides to thereby generate sequence reads of the extended oligonucleotides, each sequence read comprising a molecule identifier sequence read, a set identifier sequence read, and a cell identifier sequence read, wherein each molecule identifier sequence read is a sequence read of one of the molecule identifier sequences, each set identifier sequence read is a sequence read of one of the set identifier sequences, and each cell identifier sequence read is a sequence read of one of the cell identifier sequences. Some versions further comprise associating each cell identifier sequence read with the molecule identifier sequence read within each sequence read. Some versions further comprise grouping the sequence reads into groups comprising statistically identical set identifier sequence reads. Some versions further comprise grouping, within each group of sequence reads, the cell identifier reads into groups of statistically identical cell identifier reads. Some versions further comprise determining, within each group of sequence reads, a number of unique molecule identifier sequence reads associated with each group of statistically identical cell identifier reads. In some versions, each set of cells is isolated from a larger population of cells. In some versions, the number of total cells isolated in each set comprises no more than 10 cells. In some versions, the capture sequence on each oligonucleotide in each merged droplet is capable of hybridizing to the target sequence in the target nucleic acid of each of the cells in the set in the merged droplet under solution conditions of the merged droplet. In some versions, the capture sequence on each oligonucleotide is capable of hybridizing to the target sequence in the target nucleic acid of each of the cells in each of the sets in the merged droplet under solution conditions of the merged droplets. In some versions, the merging comprises merging each cell droplet within the immiscible medium with no more than one aqueous liquid droplet comprising the cell-lysis reagent and the oligonucleotides. In some versions, the oligonucleotides in each merged droplet are attached to a single solid substrate. Some versions further comprise, between the isolating and the merging, incubating the cell droplet within the immiscible medium at a growth temperature for a period of time. In some versions, at least one of the cells in at least one of the sets affects growth of at least one other of the cells in the at least one of the sets. Some versions further comprise, between the extending and the sequencing, amplifying the extended oligonucleotide.

In some versions, each molecule identifier sequence comprises from 2 to 16 bases.

In some versions, the capture sequence on each oligonucleotide comprises from 5 to 30 bases.

The capture sequences on the oligonucleotides in some versions are substantially identical to each other.

The target sequences on the target nucleic acids in some versions are substantially identical to each other.

In some versions, the target sequence in each of the cells comprises a conserved region of a 16S rRNA gene.

In some versions, the cell identifier sequence in each of the cells comprises a variable region of a 16S rRNA gene.

Some versions of the invention comprise providing target nucleic acid-containing liquid droplets. In some versions, each target nucleic acid-containing liquid droplet contains a separate set of target nucleic acids. In some versions, each target nucleic acid comprises a target sequence and a cell identifier sequence that identifies a type of cell in which the target nucleic acid is contained or from which the target nucleic acid is derived. Some versions further comprise providing oligonucleotide-containing liquid droplets. In some versions, each oligonucleotide-containing liquid droplet contains a separate set of oligonucleotides. In some versions, each oligonucleotide in each set of oligonucleotides comprises a set identifier sequence that identifies a single set of oligonucleotides among the sets of oligonucleotides and a capture sequence that is structured to hybridize to the target sequences. Some versions further comprise merging the target nucleic acid-containing liquid droplets with the oligonucleotide-containing liquid droplets to form merged droplets. Some versions further comprise hybridizing the oligonucleotides to the target nucleic acids within the merged droplets by hybridizing the capture sequences to the target sequences to thereby generate hybridized oligonucleotides. Some versions further comprise extending the hybridized oligonucleotides beyond the cell identifier sequences on the target nucleic acids serving as templates to thereby generate extended oligonucleotides comprising the cell identifier sequences. Some versions further comprise determining the cell identifier sequence and the set identifier sequence on each extended oligonucleotide. The determining can identify each type of cell(s) from which the target nucleic acids in each set of target nucleic acids was contained within or was derived therefrom. The target nucleic acid-containing liquid droplet can be cell-containing liquid droplets (wherein the target nucleic acids are still contained within unlysed cells) or can comprise droplets derived from cell-containing liquid droplets in which the cells are lysed prior to merging with the oligonucleotide-containing liquid droplets. The cells can be lysed by merging the cell-containing liquid droplet with a liquid droplet containing lysis buffer prior to merging with the oligonucleotide-containing liquid droplet, or by other methods.

Any of the above-mentioned versions can be combined in any combination unless the context clearly dictates otherwise.

We claim:

1. A method of analysis comprising:
providing cell-containing liquid droplets, wherein:
each cell-containing liquid droplet contains a separate set of cells; and
each cell in each set of cells comprises a target nucleic acid comprising a target sequence and a cell identifier sequence that identifies a type of cell;
providing oligonucleotide-containing liquid droplets, wherein:
each oligonucleotide-containing liquid droplet contains a separate set of oligonucleotides; and
each oligonucleotide in each set of oligonucleotides comprises a set identifier sequence that identifies a single set of oligonucleotides among the sets of oligonucleotides, a capture sequence that is structured to hybridize to the target sequences, and a molecule identifier sequence, wherein each molecule identifier sequence identifies a single oligonucleotide within the set of oligonucleotides in which the single oligonucleotide is comprised;
merging the cell-containing liquid droplets with the oligonucleotide-containing liquid droplets to form merged droplets;
hybridizing the oligonucleotides to the target nucleic acids within the merged droplets by hybridizing the capture sequences to the target sequences to thereby generate hybridized oligonucleotides;
extending the hybridized oligonucleotides beyond the cell identifier sequences on the target nucleic acids serving as templates to thereby generate extended oligonucleotides comprising the cell identifier sequences; and
determining the cell identifier sequence and the set identifier sequence on each extended oligonucleotide to thereby identify each type of cell present in each set of cells, wherein the determining comprises:
sequencing the extended oligonucleotides to thereby generate sequence reads of the extended oligonucleotides, each sequence read comprising a molecule identifier sequence read, a set identifier sequence read, and a cell identifier sequence read, wherein each molecule identifier sequence read is a sequence read of one of the molecule identifier sequences, each set identifier sequence read is a sequence read of one of the set identifier sequences and each cell identifier sequence read is a sequence read of one of the cell identifier sequences;
associating the cell identifier sequence read, the set identifier sequence read, and the molecule identifier sequence read on each sequence read;
grouping the sequence reads into groups comprising statistically identical set identifier sequence reads;
grouping, within each group of sequence reads, the cell identifier reads into groups of statistically identical cell identifier reads; and
determining, within each group of sequence reads, a number of unique molecule identifier sequence reads associated with each group of statistically identical cell identifier reads.

2. The method of claim 1, further comprising, after the merging and prior to the hybridizing, lysing the cells.

3. The method of claim 2, wherein:
each oligonucleotide-containing liquid droplet further comprises a lysis reagent; and
the lysing comprises incubating the cells in the merged droplet in the presence of the lysis reagent.

4. The method of claim 3, wherein the oligonucleotides and the lysis reagent are contained within the oligonucleotide-containing liquid droplets in a salt-containing buffer.

5. The method of claim 1, wherein the cell-containing liquid droplets, the oligonucleotide-containing liquid droplets, and the merged liquid droplets are aqueous liquid droplets encapsulated by an immiscible medium.

6. The method of claim 1, further comprising isolating the sets of cells or precursor sets of cells from a single mixture of cells to thereby provide the cell-containing liquid droplets or cell-containing liquid droplet precursors, respectively.

7. The method of claim 1, further comprising:
isolating precursor sets of cells from a single mixture of cells to thereby provide cell-containing liquid droplet precursors; and
after the isolating and before the merging, incubating the cell-containing liquid droplet precursors at a growth temperature for a period of time to thereby provide the cell-containing liquid droplets.

8. The method of claim 7, wherein at least one of the cells in at least one of the precursor sets affects growth of at least one other of the cells in the at least one of the precursor sets during the incubating.

9. The method of claim 7, wherein the number of total cells isolated in each precursor set comprises no more than 10 cells.

10. The method of claim 1, wherein the merging merges each cell-containing liquid droplet with no more than one oligonucleotide-containing liquid droplet.

11. The method of claim 1, wherein the capture sequences on the oligonucleotides are substantially identical to each other.

12. The method of claim 1, wherein the target sequences on the target nucleic acids are substantially identical to each other.

13. The method of claim 1, wherein the oligonucleotides in each set of oligonucleotides are attached to a single solid substrate.

14. The method of claim 1, further comprising, after the extending and before the determining, amplifying the extended oligonucleotide.

15. The method of claim 1, wherein the target sequence in each of the cells comprises a conserved region of a 16S rRNA gene and the cell identifier sequence in each of the cells comprises a variable region of a 16S rRNA gene.

16. A method of analysis comprising:
providing cell-containing liquid droplets, wherein:
each cell-containing liquid droplet contains a separate set of cells; and
each cell in each set of cells comprises a target nucleic acid comprising a target sequence and a cell identifier sequence that identifies a type of cell, wherein the target sequences on the target nucleic acids are substantially identical to each other, the target sequence in each of the cells comprises a conserved region of a 16S rRNA gene, and the cell identifier sequence in each of the cells comprises a variable region of a 16S rRNA gene;
providing oligonucleotide-containing liquid droplets, wherein:
each oligonucleotide-containing liquid droplet contains a separate set of oligonucleotides; and
each oligonucleotide in each set of oligonucleotides comprises a set identifier sequence that identifies a single set of oligonucleotides among the sets of oligonucleotides, a capture sequence that is structured to hybridize to the target sequences, and a molecule identifier sequence that identifies a single oligonucleotide within the set of oligonucleotides in which the single oligonucleotide is comprised, wherein the capture sequences on the oligonucleotides are substantially identical to each other;
merging the cell-containing liquid droplets with the oligonucleotide-containing liquid droplets to form merged droplets;
hybridizing the oligonucleotides to the target nucleic acids within the merged droplets by hybridizing the capture sequences to the target sequences to thereby generate hybridized oligonucleotides;
extending the hybridized oligonucleotides beyond the cell identifier sequences on the target nucleic acids serving as templates to thereby generate extended oligonucleotides comprising the cell identifier sequences; and
determining the cell identifier sequence, the set identifier sequence, and the molecule identifier sequence on each extended oligonucleotide to thereby identify each type of cell present in each set of cells, wherein the determining comprises:
sequencing the extended oligonucleotides to thereby generate sequence reads of the extended oligonucleotides, each sequence read comprising a molecule identifier sequence read, a set identifier sequence read, and a cell identifier sequence read, wherein each molecule identifier sequence read is a sequence read of one of the molecule identifier sequences, each set identifier sequence read is a sequence read of one of the set identifier sequences, and each cell identifier sequence read is a sequence read of one of the cell identifier sequences;
associating the cell identifier sequence read, the set identifier sequence read, and the molecule identifier sequence read on each sequence read;
grouping the sequence reads into groups comprising statistically identical set identifier sequence reads;
grouping, within each group of sequence reads, the cell identifier reads into groups of statistically identical cell identifier reads; and
determining, within each group of sequence reads, a number of unique molecule identifier sequence reads associated with each group of statistically identical cell identifier reads.

17. The method of claim 16, further comprising:
isolating precursor sets of cells from a single mixture of cells to thereby provide cell-containing liquid droplet precursors; and
after the isolating and before the merging, incubating the cell-containing liquid droplet precursors at a growth temperature for a period of time to thereby provide the cell-containing liquid droplets, wherein at least one of the cells in at least one of the precursor sets affects growth of at least one other of the cells in the at least one of the precursor sets during the incubating.

* * * * *

SEQUENCE LISTING

```
<160> NUMBER OF SEQ ID NOS: 5

<210> SEQ ID NO 1
<211> LENGTH: 66
<212> TYPE: DNA
<213> ORGANISM: Artificial Sequence
<220> FEATURE:
<223> OTHER INFORMATION: Bead oligonucleotide
<220> FEATURE:
<221> NAME/KEY: misc_feature
<222> LOCATION: (31)..(46)
<223> OTHER INFORMATION: n is a, c, g, or t

<400> SEQUENCE: 1
tttttttcct acacgacgct cttccgatct nnnnnnnnnn nnnnnnggac tachvgggtw      60
tctaat                                                                66

<210> SEQ ID NO 2
<211> LENGTH: 68
<212> TYPE: DNA
<213> ORGANISM: Artificial Sequence
<220> FEATURE:
<223> OTHER INFORMATION: oOSV377  primer

<400> SEQUENCE: 2
aatgatacgg cgaccaccga gatctacact ggcgcacact ctttccctac acgacgctct      60
tccgatct                                                              68
```

```
<210> SEQ ID NO 3
<211> LENGTH: 86
<212> TYPE: DNA
<213> ORGANISM: Artificial Sequence
<220> FEATURE:
<223> OTHER INFORMATION: oOSV381 primer

<400> SEQUENCE: 3
caagcagaag acggcatacg agatacgaca ctgtgactgg agttcagacg tgtgctcttc      60
cgatctcgtg ccagcagccg cggtaa                                          86

<210> SEQ ID NO 4
<211> LENGTH: 33
<212> TYPE: DNA
<213> ORGANISM: Artificial Sequence
<220> FEATURE:
<223> OTHER INFORMATION: oOSV570 primer

<400> SEQUENCE: 4
acactctttc cctacacgac gctcttccga tct                                  33

<210> SEQ ID NO 5
<211> LENGTH: 52
<212> TYPE: DNA
<213> ORGANISM: Artificial Sequence
<220> FEATURE:
<223> OTHER INFORMATION: oOSV571  primer

<400> SEQUENCE: 5
gactggagtt cagacgtgtg ctcttccgat ctcgtgccag cagccgcggt aa             52
```